(12) United States Patent
Pugin et al.

(10) Patent No.: US 6,169,192 B1
(45) Date of Patent: Jan. 2, 2001

(54) FUNCTIONALIZED FERROCENYLDIPHOSPHINES, A PROCESS FOR THEIR PREPARATION AND THEIR USE

(75) Inventors: Benoît Pugin, Münchenstein; Heidi Landert, Bourrignon, both of (CH)

(73) Assignee: Novartis AG, Basel (CH)

( * ) Notice: Under 35 U.S.C. 154(b), the term of this patent shall be extended for 0 days.

(21) Appl. No.: 09/214,667

(22) PCT Filed: Jul. 9, 1997

(86) PCT No.: PCT/EP97/03626

§ 371 Date: Jan. 8, 1999

§ 102(e) Date: Jan. 8, 1999

(87) PCT Pub. No.: WO98/01457

PCT Pub. Date: Jan. 15, 1998

(30) Foreign Application Priority Data

Jul. 10, 1996 (CH) .................................................. 1746/96
Aug. 23, 1996 (CH) .................................................. 2069/96

(51) Int. Cl.[7] ............................ C07F 17/02; C07F 19/00; B01J 31/00
(52) U.S. Cl. ................................ 556/11; 556/12; 556/18; 556/22; 556/28; 556/143; 556/144; 502/154; 502/155; 502/158
(58) Field of Search ................................. 556/11, 12, 18, 556/22, 28, 143, 144; 502/154, 155, 158

(56) References Cited

U.S. PATENT DOCUMENTS

| | | | |
|---|---|---|---|
| 5,371,256 | 12/1994 | Togni et al. | 556/14 |
| 5,466,844 | 11/1995 | Spindler et al. | 556/11 |
| 5,583,241 | 12/1996 | Spindler | 556/143 |
| 5,627,293 | 5/1997 | Pugin | 556/11 |
| 5,783,715 | 7/1998 | Pugin | 556/11 |
| 5,925,778 | * 7/1999 | Pugin | 556/144 |

FOREIGN PATENT DOCUMENTS

| | | |
|---|---|---|
| 0496699 | 7/1992 | (EP) . |
| 0496700 | 7/1992 | (EP) . |
| 0564406 | 10/1993 | (EP) . |
| 0729969 | 9/1996 | (EP) . |
| 9632400 | 10/1996 | (WO) . |
| 9702232 | 1/1997 | (WO) . |

OTHER PUBLICATIONS

Achiwa, K., "Catalytic Asymmetric Hydrogenations with Polymer Supported Chiral Pyrrolidinephosphine–Rhodium Complexes", Chemistry Letters, 1978, pp. 905–908.

Cullen et al., "Polymer Supported Ferrocene Derivatives. Catalytic Hydrosilylation of Olefins by Supported Palladium and Platinum Complexes", J. of Organom. Chem., vol. 333, 1987, pp. 269–280.

Togni, A., "Developing New Chiral Ferrocenyl Ligands for Asymmetric Catalysis: A Personal Account", Chimia, vol. 50, 1996, pp. 86–93.

Kim et al., "Functionalized Organometallic Ligand (1) Synthesis of Some Ferrocene Derivatives of Cyclohexyl–and Cyclopentadienyl–phosphines," Bull. Korean Chem. Soc., vol. 13, No. 6, 1992, pp. 588–592.

* cited by examiner

Primary Examiner—Porfirio Nazario-Gonzalez
(74) Attorney, Agent, or Firm—Wenderoth, Lind & Ponack, L.L.P.

(57) ABSTRACT

The invention relates to 1,2-ferrocenyldiphosphines which contain a functional group in the 1' position either directly or via a bridging group, and also a process for their preparation. The compounds are important for transition metal complexes containing d-8 metals such as Rh, Ru, Pd or Ir. These transition metal complexes are widely used in the hydrogenation of organic double or triple bonds, in particular olefinic double bonds and carbon-heteroatom double bonds. The complexes are particularly suitable for enantioselective hydrogenation using chiral ferrocenyldiphosphines and corresponding prochiral unsaturated compounds. Ferrocenyldiphosphines having a functional group in the 1' position are also important intermediates for ferrocenyldiphosphine ligands and their metal complexes of d-8 metals such as rhodium, ruthenium, palladium or iridium which are bound to inorganic polymeric supports via this functional group. These metal complexes bound to an inorganic or organic support material are likewise very suitable for the hydrogenation of organic double or triple bonds.

26 Claims, No Drawings

FUNCTIONALIZED FERROCENYLDIPHOSPHINES, A PROCESS FOR THEIR PREPARATION AND THEIR USE

The invention relates to 1,2-ferrocenyldiphosphines which contain a functional group in the 1' position either directly or via a bridging group, and also a process for their preparation. The compounds are important ligands for transition metal complexes containing d-8 metals such as Rh, Ru, Pd or Ir. These transition metal complexes are widely used in the hydrogenation of organic double or triple bonds, in particular olefinic double bonds and carbon-heteroatom double bonds. The complexes are particularly suitable for enantioselective hydrogenation using chiral ferrocenyldiphosphines and corresponding prochiral unsaturated compounds.

Ferrocenyldiphosphines having a functional group in the 1' position are also important intermediates for ferrocenyldiphosphine ligands and their metal complexes of d-8 metals such as rhodium, ruthenium, palladium or iridium which are bound to inorganic or organic polymeric supports via this functional group. These metal complexes bound to an inorganic or organic support material are likewise very suitable for the hydrogenation of organic double or triple bonds.

The invention further provides extractable or adsorbable ferrocenyldiphosphines and ferrocenyldiphosphines having an adjusted solubility and catalysts comprising these ferrocenyldiphosphines, and also a process for preparing the compounds mentioned. These are either ferrocenyldiphosphines containing a functional group in the 1' position or ferrocenyldiphosphines derived therefrom.

EP-A-0-496 699 and EP-A-0 496 700 describe dioxolane- and pyrrolidine-diphosphines containing silane groups and also their rhodium or iridium complexes which are fixed to an inorganic support material, for example a silicate. In a hydrogenation, these give a heterogeneous reaction mixture from which the inorganically fixed catalyst can easily be separated after the reaction is complete.

Monophosphines or diphosphines bound to polymers have likewise become known. They can be fixed in two fundamentally different ways:
a) by copolymerization of diphosphines bound to appropriate monomers and
b) by reaction of functionalized diphosphines with previously formed, functional polymers, either directly or via an additional bridging group.

Thus, for example, K. Achiwa in J. Chem. Japan Soc., Chemistry Letters, pages 905 to 908 (1978) describes polystyrene copolymers whose benzene rings contain rhodium-complexed pyrrolidine-diphosphine-N-carbonyl groups. The synthesis of the monomers is difficult and the hydrogenation of prochiral olefins using these heterogeneous catalysts is, compared with catalysts not bound to polymer, associated with a lowering of the activity, the productivity and the enantioselectivity. The pyrrolidine-diphosphine ligands are fixed via a para-amide bond directly to the benzene ring of the styrene which forms part of the copolymer while the other part of the copolymer framework is formed by hydroxyethyl methacrylate.

In J. of Organometallic Chemistry, 333 (1987), 269–280, W. R. Cullen et. al. describe ferrocene derivatives such as N,N-dimethyl-1-(2-diphenylphosphinoferrocenyl) ethylamine which is bound directly to an oxidized polystyrene group. In the procedure proposed there, a maximum of 20% of the ferrocene derivative used is bound to the polymeric support and the ferrocenyl ligand is unspecifically and unselectively, partly via one or the other cyclopentadienyl ring to the polymer.

Ferrocenes which are substituted by 2 phosphine groups only on one cyclopentadienyl ring have been known for a relatively long time. Their preparation and use as ligands in metal complexes for stereoselective hydrogenations is described, for example, in EP-A-564 406.

Recently, A. Togni in Chimia 50, (1996), 86–93 published the compound (A1)

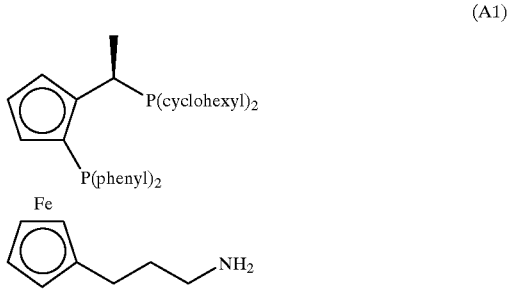

(A1)

which appears to be able to be prepared in a complicated synthesis which builds up the cyclopentadienyl rings. The method of preparation is analogous to the process described in Organometallics 1994, 13, 4481–4493.

It has now been found that ferrocenyldiphosphines which contain a functional group bound either directly or via a bridging group to only one cyclopentadienyl ring can be prepared in a simple way and can be immobilized on both inorganic and organic polymeric support materials, and can also be used as extractable and/or adsorbable ligands/catalysts. They can be bound to a previously prepared polymer either directly or via a bridging group or they can be immobilized after introduction of a polymerizable group by copolymerization of the monomers thus obtained. With $d^8$ metals such as rhodium, ruthenium, palladium and iridium, the immobilized ferrocenyldiphosphine ligands form complexes which can be used as highly active catalysts in enantioselective hydrogenations of carbon—carbon, carbon-nitrogen, or carbon-oxygen double bonds. The selectivity and the total yield are surprisingly high for immobilized systems. In particular for imine hydrogenation, the iridium catalysts are particularly well suited since they have the clearly highest activity and the highest catalyst productivity in comparison with other immobilized systems. Their selectivity is likewise very good. The catalysts can easily be separated from the reaction solution and be reused. Virtually no metal and ligand losses occur. These immobilized catalysts therefore allow, in particular, industrial-scale hydrogenations to be carried out economically.

The reaction to be catalysed can, for example in the case of ferrocenyldiphosphine ligands bound to a polymer, even be carried out heterogeneously or homogeneously depending on the choice of the polymer. The polymer can be prepared or even subsequently specifically modified such that the catalyst bound to the polymer dissolves in the reaction medium, can easily be separated off after the reaction by filtration, ultrafiltration, extraction or adsorbtion to support materials and can then be reused. The catalysts can be reused a number of times. Selection of the polymer enables the catalyst to be matched optimally to the reaction medium during the hydrogenation step and then be completely separated off, which is particularly important for hydrogenations carried out on an industrial scale.

In all cases, the recovery of the noble metals present when the catalyst has to be replaced after frequent recycling is made easier. It is frequently also possible to omit further purification of the hydrogenated product since the catalyst can be removed virtually quantitatively.

The preparation of these immobilized or extractable and/or adsorbable ferrocenyldiphosphines has been made possible for the first time by the provision of appropriately functionalized ferrocenyldiphosphines. These intermediates and their preparation are therefore of great importance.

The invention provides compounds of the formula VI

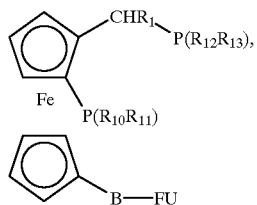

(VI)

$R_1$ is $C_1$–$C_8$alkyl, phenyl or phenyl substituted by from 1 to 3 $C_1$–$C_4$alkyl or $C_1$–$C_4$alkoxy;

$R_{10}$, $R_{11}$, $R_{12}$ and $R_{13}$ are, independently of one another, $C_1$–$C_{12}$alkyl, $C_5$–$C_{12}$cycloalkyl, phenyl, $C_5$–$C_{12}$cycloalkyl substituted by $C_1$–$C_4$alkyl or $C_1$–$C_4$alkoxy or phenyl substituted by from one to three $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —[$^+NR_7R_8R_9$]$X^-$ or $C_1$–$C_5$fluoroalkyl; or the groups —$PR_{10}R_{11}$ and —$PR_{12}R_{13}$ are each, independently of one another, a radical of the formula IV, IVa, IVb or IVc

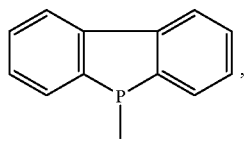

(IV)

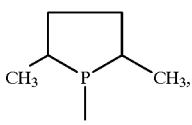

(IVa)

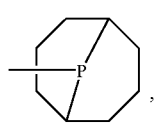

(IVb)

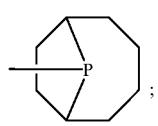

(IVc)

$R_4$, $R_5$ and $R_6$ are, independently of one another, $C_1$–$C_{12}$alkyl or phenyl;

$R_7$ and $R_8$ are, independently of one another, H, $C_1$–$C_{12}$alkyl or phenyl or $R_7$ and $R_8$ together are tetramethylene, pentamethylene or 3-oxa-1,5-pentylene;

$R_9$ is H or $C_1$–$C_4$alkyl;

M is H or an alkali metal;

$X^-$ is the anion of a monobasic acid;

halogen is fluorine, chlorine, bromine or iodine; and a) B is a direct bond and FU is a functional group bound via a carbon atom to the cyclopentadienyl; or b) B is a bridging group bound via a carbon atom or a silicon atom to the cyclopentadienyl and FU is a functional group;

with the exception of the compound of the formula (VI) in which $R_1$ is methyl, $R_{10}$ and $R_{11}$ are phenyl, $R_{12}$ and $R_{13}$ are cyclohexyl, B is 1,3-propylene and FU is $NH_2$; and with the exception of compounds of the formula (VI) in which B is $Si(R_{12'})_2$—$R_{13'}$ and FU is Z, where $R_{12'}$ are, independently of one another, $C_1$–$C_{12}$alkyl, $C_3$–$C_7$cycloalkyl, benzyl or phenyl or the two radicals $R_{12'}$ together are $C_5$–$C_{12}$alkylene;

$R_{13'}$ is $C_1$–$C_{12}$alkylene or phenylene;

Z is Cl, $NH_2$, NH—$C_1$–$C_{12}$alkyl or a group —A—CO—NH—$R_{14}$—$Si(R_a)_n(OR_{15})_{3-n}$;

A is NH or N($C_1$–$C_{12}$alkyl);

$R_{14}$ is $C_1$–$C_{12}$alkylene;

$R_{15}$ is $C_1$–$C_{12}$alkyl;

$R_a$ is $C_1$–$C_4$alkyl or $OR_{15}$; and n is 0, 1 or 2.

In the context of the present invention, the term functional group means that this group forms a chemical bond with other functional groups by addition or substitution.

For example, it is also possible to carry out a chain extension of the functional group and/or bind a polymerizable group to it by known methods. Known methods are, for example, etherification, esterification, amidation and formation of urea or urethane groups.

Methods of derivatizing functional groups are known from textbooks on organic chemistry (E. Breitmaier, Günther Jung; Organische Chemie II (1983); Georg Thieme Verlag Stuttgart, New York pp. 342, 409ff).

Examples of directly C-bonded functional groups are the carboxylic acid, carboxylate, carboxylic ester, carboxamide, cyano, imino, aldehyde or ketone group.

Preference is given to the aldehyde or ketone group.

Examples of functional groups bound to a carbon atoms of a bridging group are the abovementioned groups plus the amine, alcohol, isocyanate, halogen or glycidyl group.

The functional group can also be a polymerizable group and in this case is preferably a vinyl group which is unsubstituted or substituted by $C_1$–$C_4$alkyl. It can, for example, be bonded to the bridging group via an amide or ester group.

The polymerizable group can be derived from ethylenically unsaturated alcohols, amines and isocyanates such as allyl alcohol, allylamine, allyl isocyanate, crotyl alcohol; monoesters or monoamides of dicarboxylic acids and unsaturated alcohols and amines; functional styrenes such as chloromethylstyrene, hydroxystyrene, hydroxyethoxystyrene, styrylamine, styryl(hydroxyethyl)amine, styrenecarboxylic acid, styrenesulfonic acid, vinyl hydroxyethyl ether, acrylic acid, methacrylic acid, acrylamide and methacrylamide, acryl- and methacryl-($C_2$–$C_6$hydroxyalkyl)amide, $C_2$–$C_6$hydroxyalkyl acrylate and methacrylate.

The functional group bound via a carbon atom of a bridging group B is preferably an amine group, alcohol group or a polymerizable group.

Linkages via these functional groups can be carried out by generally known methods. It is in principle also possible to convert existing functional groups into other functional groups, for example —$CH_2OH$-groups into carboxylic acids by oxidation, carboxylic acids into amides or halides, amine groups into isocyanate groups, alcohols or amines into carbonates or urethanes. It is also possible to react alcohols or amines first with halogenated carboxylic acids (for example chloroacetic acid). It is also possible to use chain extenders such as epoxides, aziridines, dioles, diamines, dicarboxylic acids or esters and diisocyanates, either singly or a plurality thereof in succession, and thus determine the length of the extension group in a defined manner. These methods and processes for linkage are known and described in the specialist literature.

When the functional group FU is (O)C—H, (O)C—($C_1$–$C_{12}$)alkyl, COOH or COO($C_1$–$C_6$)alkyl, this group can also be converted into another functional group by reduction, transesterification or other known standard reactions or organic chemistry. Thus, for example, the aldehyde group can easily be converted into an amine group by reaction with an amine and subsequent hydrogenation. It is likewise possible to reduce it to the alcohol using, for example, $LiAlH_4$.

An OH, $NH_2$ or NH($C_1$–$C_{12}$alkyl) functional group can also be converted into an oxyalkylsilyl group by reaction with a compound of the formula IX $(R_{16})_n(R_{15}O)_{3-n}Si$—$R_{14}$—NCO (IX) where $R_{14}$ is $C_1$–$C_{12}$alkylene, $R_{15}$ is $C_1$–$C_{12}$alkyl, $R_{16}$ is $C_1$–$C_4$alkyl and n is 0, 1 or 2.

The statements below regarding the bridging group B bound via a carbon atom to the cyclopentadienyl also apply analogously to bridging groups bound via a silicon atom, with the bridging group preferably being bound to the cyclopentadienyl via the group —Si($R_{12'}$)$_2$—.

The bridging group B can contain from 1 to 30 atoms, preferably from 1 to 20 atoms and particularly preferably from 1 to 12 atoms, selected from the group consisting of C, O, S and N in the chain. The bridging group is preferably a hydrocarbon radical which can be interrupted by one or more heteroatoms selected from the group consisting of O, S and N and/or the group C(O).

A chain-extended bridging group B can have the formula (XIV)

$$-X_1-(R_{104})-X_2- \qquad (XIV)$$

in which $X_1$ and $X_2$ are each, independently of one another, a direct bond, or $X_1$ and $X_2$ are, independently of one another, selected from the group consisting of —O—, —S—, —$NR_{105}$—, —C(O)—O—, —O—C(O)—, —O—C(O)—O—, —$SO_2$—O—, —O—$SO_2$—, —O—$SO_2$—O, —$NR_{105}$—C(O)—, —C(O)—$NR_{105}$—, —$NR_{105}$—C(O)—O—, —O—C(O)—$NR_{105}$—, —$NR_{105}$—C(O)—$NR_{105}$—, —$NR_{105}SO_2$—, —$SO_2$—$NR_{105}$—, —$NR_{105}$—$SO_2$—O—, —O—$SO_2NR_{105}$— or —$NR_5SO_2$—$NR_{105}$—, in which $R_{105}$ is H or $C_1$–$C_{30}$alkyl, $C_5$cycloalkyl or $C_6$cycloalkyl, $C_5$cycloalkylmethyl, $C_6$cycloalkylmethyl, $C_5$cycloalkylethyl or $C_6$cycloalkylethyl, phenyl, benzyl or 1-phenyleth-2-yl, and $R_{104}$ is a bivalent bridging group.

Alkyl radicals $R_{105}$ preferably contain from 1 to 6 carbon atoms and particularly preferably from 1 to 4 carbon atoms. Some examples are methyl, ethyl, n- or i-propyl, butyl, hexyl and octyl. The preferred cycloalkyl radical $R_5$ is cyclohexyl, and the preferred cycloalkylmethyl radical $R_5$ is cyclohexylmethyl. In a preferred embodiment, $R_5$ is H or $C_1$–$C_4$alkyl.

The bivalent bridging group $R_{104}$ is preferably a hydrocarbon radical which contains preferably from 1 to 30, more preferably from 1 to 18, particularly preferably from 1 to 12 and in particular from 1 to 8 carbon atoms and is unsubstituted or monosubstituted or polysubstituted by $C_1$–$C_4$alkyl, $C_1$–$C_4$alkoxy or =O. The hydrocarbon radical can also be interrupted by one or more heteroatoms selected from the group —O—, —S— and —$NR_5$—, where $R_5$ is preferably H or $C_1$–$C_4$alkyl.

The bivalent bridging group $R_{104}$ can be, for example, $C_1$–$C_{20}$alkylene, preferably $C_2$–$C_{12}$alkylene, which can be linear or branched. Some examples are methylene, ethylene, 1,2- or 1,3-propylene, 1,2-, 1,3- or 1,4-butylene, pentylene, hexylene, octylene, dodecylene, tetradecylene, hexadecylene and octadecylene.

The bivalent bridging group $R_{104}$ can be, for example, polyoxyalkylene having from 2 to 12, preferably 2–6 and particularly preferably from 2 to 4 oxyalkylene units and from 2 to 4, preferably 2 or 3, carbon atoms in the alkylene. The bivalent bridging group $R_{104}$ is particularly preferably polyoxyethylene or polyoxypropylene having from 2 to 6 oxyalkylene units.

The bivalent bridging group $R_{104}$ can be, for example, $C_5$–$C_{12}$cycloalkyl, preferably $C_5$–$C_8$cycloalkyl and particularly preferably $C_5$cycloalkyl or $C_6$cycloalkyl, for example cyclopentylene, cyclohexylene, cyclooctylene or cyclododecylene.

The bivalent bridging group $R_{104}$ can be, for example, $C_5$–$C_{12}$cycloalkyl, preferably $C_5$–$C_8$cycloalkyl- and particularly preferably $C_5$cycloalkyl- or $C_6$cycloalkyl-$C_1$–$C_{12}$alkyl and preferably —$C_1$–$C_4$alkyl. Some examples are cyclopentyl-$C_nH_{2n}$— and cyclohexyl-$C_nH_{2n}$—, in which n is a number from 1 to 4. Particular preference is given to -cyclohexyl-$CH_2$—.

The bivalent bridging group $R_{104}$ can be, for example, $C_5$–$C_{12}$cycloalkyl-, preferably $C_5$–$C_8$cycloalkyl- and particularly preferably $C_5$cycloalkyl- or $C_6$cycloalkyl-($C_1$–$C_{12}$alkyl)$_2$- and preferably —($C_1$–$C_4$alkyl)$_2$. Some examples are cyclopentyl-($C_nH_{2n}$—)$_2$ and cyclohexyl-($C_nH_{2n}$—)$_2$, in which n is a number from 1 to 4. Particular preference is given to —$CH_2$-cyclohexyl-$CH_2$—.

The bivalent bridging group $R_{104}$ can be, for example, $C_6$–$C_{14}$arylene or preferably $C_6$–$C_{10}$arylene, for example naphtylene or more preferably phenylene.

The bivalent bridging group $R_{104}$ can be, for example, $C_7$–$C_{20}$aralkylene or preferably $C_7$–$C_{12}$aralkylene. More preferable is arylene-$C_nH_{2n}$—, in which arylene is naphthylene and particularly phenylene and n is a number from 1 to 4. Examples are benzylene and phenylethylene.

The bivalent bridging group $R_{104}$ can be, for example, arylene-($C_nH_{2n}$—)$_2$, in which arylene is preferably naphthylene and particularly phenylene and n is a number from 1 to 4. Examples are xylylene and phenylene ($C_2H_2$)$_2$—.

A preferred group of compounds is formed when B is a direct bond and FU is (O)C—H, (O)C—($C_1$–$C_{12}$)-alkyl, COOH, CN, or COO($C_1$–$C_{12}$)alkyl.

Another preferred group of compounds is formed when B is unsubstituted linear or branched $C_1$–$C_{12}$alkylene, $C_2$–$C_{12}$alkenylene, $C_2$–$C_{12}$alkynylene, $C_5$–$C_{12}$cycloalkylene, $C_5$–$C_{12}$cycloalkenylene, phenylene, phenylene-($C_1$–$C_{12}$)alkylene or linear or branched ($C_1$–$C_{12}$) alkylene, $C_2$–$C_{12}$alkenylene, $C_2$–$C_{12}$alkynylene, $C_5$–$C_{12}$cycloalkylene, $C_5$–$C_{12}$cycloalkenylene, phenylene or phenylene-($C_1$–$C_{12}$)alkylene substituted by ($C_1$–$C_4$)alkyl, ($C_1$–$C_4$)alkoxy, halogen or hydroxy, and FU is halogen, OH, $NH_2$,NH($C_1$–$C_{12}$)alkyl, (O)C—H, (O)C—($C_1$–$C_{12}$alkyl, COOH, COCl, COO($C_1$–$C_6$)alkyl or a group OC(O)—$CR_c$=$CR_dR_e$ or OC($NR_i$)—$CR_c$=$CR_dR_e$, in which $R_c$, $R_d$, $R_e$ and $R_i$ are, independently of one another, hydrogen, $C_1$–$C_6$ alkyl or phenyl.

When the group B is halogen- or hydroxy-substituted linear or branched $C_1$–$C_{12}$alkylene, $C_2$–$C_{12}$alkenylene, $C_2$–$C_{12}$alkynylene, $C_5$–$C_{12}$cycloalkylene, $C_5$–$C_{12}$cycloalkenylene, phenylene or phenylene-($C_1$–$C_{12}$) alkylene, this group together with the functional group FU provide preferably at least two functional centres which can be utilized for further reactions or chain extensions.

A particularly preferred group of compounds is obtained when B is a direct bond and FU is (O)C—H, (O)C—(C$_1$–C$_{12}$)alkyl, COOH, COCl or COO(C$_1$–C$_6$)alkyl. FU is very particularly preferably (O)CH or (O)C—(C$_1$–C$_{12}$) alkyl.

The bridging group B can also be unsubstituted or C$_1$–C$_4$alkyl-, C$_1$–C$_4$alkoxy-, halogen- or hydroxy-substituted linear or branched or C$_1$–C$_{12}$alkylene, C$_2$–C$_{12}$alkenylene or C$_2$–C$_{12}$alkynylene.

B is particularly preferably unsubstituted or halogen- or OH-substituted C$_1$–C$_{12}$alkylene.

Examples of alkylene are methylene, ethylene and the various positional isomers of propylene, butylene, pentylene, hexylene, heptylene, octylene, nonylene, decylene, undecylene or dodecylene. Examples of substituted alkylenes are 1- or 2-hydroxypropylene, 1-, 2- or 3-hydroxybutylene, the various positional isomers of chloropropylene and chlorobutylene. Examples of alkenylene are propenylene, butenylene, pentenylene or hexenylene.

A cycloalkylene radical B preferably contains from 5 to 8, particularly preferably 5 or 6, ring carbon atoms.

Examples of cycloalkylene are cyclopentylene, cyclohexylene, cycloheptylene, cyclooctylene, cyclodecylene, cycloundecylene and cyclododecylene. Preference is given to cyclopentylene and cyclohexylene and particular preference is given to cyclohexylene.

The cycloalkylene can be substituted by C$_1$–C$_4$alkyl, C$_1$–C$_4$alkoxy, halogen or hydroxy. Examples of such substituents have been given above.

Preference is given to halogen, OH, methyl and ethyl and to methoxy and ethoxy. Examples of substituted cycloalkylene are hydroxycyclohexylene, methylcyclopentylene, methoxycyclopentylene, methylcyclohexylene and methoxycyclohexylene.

Examples of cycloalkenylene are cyclopentenylene, cyclohexenyien, cycloheptenylene, cyclooctenylen, cyclodecenylene, cycloundecenylene and cyclododecenylene. Preference is given to cyclopentenylene and cyclohexenylene and particular preference is given to cyclohexenylene.

C$_1$–C$_4$Alkyl-, C$_1$–C$_4$alkoxy-, halogen- or hydroxy-substituted phenylene or phenylene-(C$_1$–C$_{12}$)alkylene as B preferably contains 1 or 2 substituents. If the phenylene contains 2 or 3 substituents, these can be identical or different.

Examples of alkyl and alkoxy substituents have been given above; preferred alkyl and alkoxy substituents for phenylene are methyl, ethyl and also methoxy and ethoxy.

Halogen as phenylene substituent is preferably —F, —Cl and —Br.

Preferred phenylene-(C$_1$–C$_{12}$)alkylene is phenylenepropylene, phenyleneethylene or the benzylene group.

When B is a bridging group, FU is preferably OH, NH$_2$, NH(C$_1$–C$_{12}$)alkyl, HC(O). Examples of C$_1$–C$_{12}$alkyl have been given above.

An alkyl radical R$_1$ is preferably linear. It preferably contains from 1 to 4 carbon atoms. Examples of such alkyl are methyl, ethyl, n- and i-propyl, n-, i- and t-butyl, pentyl, hexyl, heptyl and octyl. Preference is given to methyl, ethyl and propyl and particular preference is given to methyl.

R$_1$ as substituted phenyl preferably has 1 to 2 substituents. Alkyl substituents can be, for example, methyl, ethyl, n- and i-propyl, n-, i- and t-butyl; preference is given to methyl and ethyl. Alkoxy substituents can be, for example, methoxy, ethoxy, n- and i-propoxy, n-, i- and t-butoxy; preference is given to methoxy and ethoxy. In one group of compounds of the formula I, R$_1$ is preferably phenyl or phenyl substituted by 1 or 2 C$_1$–C$_4$alkyl or C$_1$–C$_4$alkoxy.

Alkyl radicals R$_{10}$, R$_{11}$, R$_{12}$ and R$_{13}$ can be linear or branched and contain preferably from 1 to 8 and particularly preferably from 1 to 4 carbon atoms. Examples of such alkyl are methyl, ethyl, n- and i-propyl, n-, i- and t-butyl, pentyl, hexyl, heptyl, octyl, nonyl, decyl, undecyl and dodecyl. Preference is given to methyl, ethyl, n- and i-propyl, n-, i- and t-butyl. When R$_{10}$ and R$_{11}$ are identical alkyl radicals, they are particularly preferably i-propyl or t-butyl.

Cycloalkyl radicals R$_{10}$, R$_{11}$, R$_{12}$ and R$_{13}$ contain preferably from 5 to 8, particularly preferably 5 or 6, ring carbon atoms. Examples of cycloalkyl are cyclopentyl, cyclohexyl, cycloheptyl, cyclooctyl, cyclodecyl and cyclododecyl. Preference is given to cyclopentyl and cyclohexyl and particular preference is given to cyclohexyl.

The cycloalkyl can be substituted, for example by from 1 to 3 alkyl or alkoxy substituents; examples of such substituents have been given above. Preference is given to methyl and ethyl and to methoxy and ethoxy. Examples of substituted cycloalkyl are methylcyclopentyl, methoxycyclopentyl, methylcyclohexyl and methoxycyclohexyl.

Substituted phenyl radicals R$_{10}$, R$_{11}$, R$_{12}$ and R$_{13}$ preferably contain 1 or 2 substituents. If the phenyl has 2 or 3 substituents, these can be identical or different.

Examples of the alkyl and alkoxy substituents have been given above; preferred alkyl and alkoxy substituents for phenyl are methyl, ethyl and also methoxy and ethoxy.

Halogen substituents for phenyl are preferably —F, —Cl and —Br.

A C$_1$–C$_5$fluoroalkyl substituent on phenyl is perfluorinated or partially fluorinated C$_1$–C$_5$alkyl. Examples of such substituents are the positional isomers of mono- to decafluoropentyl, mono- to octafluorobutyl, mono- to hexafluoropropyl, mono- to tetrafluoroethyl and also mono- and difluoromethyl. Among the partially fluorinated alkyl radicals, those of the formulae —CF$_2$H and —CF$_2$(C$_1$–C$_4$alkyl) are particularly preferred. Particular preference is given to a perfluorinated alkyl. Examples are perfluoropentyl, perfluorobutyl, perfluoropropyl, perfluoroethyl and in particular trifluoromethyl. The fluorine-substituted alkyl groups are preferably bound in the 3, 4 or 5 position.

R$_4$, R$_5$ and R$_6$ can be linear or branched alkyl which contains preferably from 1 to 8 and particularly preferably from 1 to 4 carbon atoms. Examples of alkyl have been given above. Alkyl is preferably methyl, ethyl, n-propyl, n-butyl or t-butyl. The substituent —SiR$_4$R$_5$R$_6$ is particularly preferably trimethylsilyl.

Among the acid phenyl substituents —SO$_3$M, —CO$_2$M and —PO$_3$M, the group —SO$_3$M and —CO$_2$M is preferred. M is preferably H, Li, Na or K.

Alkyl radicals R$_7$ and R$_8$ contain preferably from 1 to 6, particularly preferably from 1 to 4, carbon atoms. The alkyl radical is preferably linear. Preferred examples are methyl, ethyl, n-propyl and n-butyl. An alkyl radical R$_9$ is preferably methyl.

An anion X$^-$ of a monobasic acid is preferably Cl$^-$, Br$^-$ or the anion of a carboxylic acid, for example formate, acetate, trichloroacetate or trifluoroacetate.

Preferred examples of R$_{10}$, R$_{11}$, R$_{12}$ and R$_{13}$ as substituted phenyl are 2-methyl-, 3-methyl-, 4-methyl-, 2- or 4-ethyl-, 2- or 4i-propyl-, 2- or 4-t-butyl-, 2-methoxy-, 3-methoxy-, 4-methoxy-, 2- or 3-ethoxy-, 4trimethylsilyl-, 2- or 4-fluoro-, 2,4-difluoro-, 2- or 4-chloro-, 2,4-dichloro-, 2,4-dimethyl-, 3,5-dimethyl-, 2-methoxy-4-methyl-, 3,5- dimethyl-4-methoxy-, 3,5-dimethyl-4-(dimethylamino)-, 2- or 4-amino-, 2- or 4-methylamino-, 2- or 4-(dimethylamino)-, 2- or 4-SO$_3$H-, 2- or 4-SO$_3$Na-, 2- or 4-[$^+$NH$_3$Cl$^-$]-, 3,4,5-trimethyl-, 2,4,6-trimethyl-, 4trifluoromethyl- or 3,5-di(trifluoromethyl)phen-1-yl.

R$_{10}$ and R$_{11}$ are particularly preferably cyclohexyl, t-butyl, phenyl, 2- or, 4-methylphen-1-yl, 2- or 4-methoxyphen-1-yl, 2- or 4-(dimethylamino)phen-1-yl, 3,5-dimethyl-4 -(dimethylamino)phen-1-yl and 3,5-dimethyl-4-methoxyphen-1-yl, but are particularly preferably cyclohexyl, phenyl, 4-methylphen-1-yl and t-butyl.

R$_{12}$ and R$_{13}$ are preferably C$_1$–C$_8$alkyl. Examples of C$_1$–C$_8$alkyl have already been mentioned.

Particularly preferably, R$_{12}$ and R$_{13}$ are identical and are i-propyl or t-butyl.

Cycloalkyl radicals R$_{12}$ and R$_{13}$ preferably have from 5 to 8 carbon atoms.

Another preferred group of compounds is obtained when R$_{12}$ and R$_{13}$ are unsubstituted phenyl or phenyl substituted by 1 or 2 substituents.

A further group of particularly preferred compounds is obtained when R$_{12}$ and R$_{13}$ are identical and are t-butyl, phenyl, cyclohexyl, 2- or 4-methylphen-1-yl, 2- or 4-methoxyphen-1-yl, 2- or 4-(dimethylamino)phen-1-yl, 3,5-dimethylphen-1-yl or and 3,5-dimethyl-4-methoxyphen-1-yl; very particularly preferably, R$_{12}$ and R$_{13}$ are identical and are t-butyl, cyclohexyl, phenyl or 3,5-dimethylphen-1-yl.

Specifically preferred compounds are those in which R$_1$ is methyl, R$_{12}$ and R$_{13}$ are each t-butyl, cyclohexyl, phenyl or 3,5-dimethylphen-1-yl and R$_{10}$ and R$_{11}$ are phenyl, cyclohexyl or t-butyl.

There has hitherto not been any known process which allows, for example, a phosphorus group as electrophile to be introduced, in a first step, with high selectivity and stereoselectively into the already substituted cyclopentadienyl ring of (R)- or (S)-N,N-dimethyl-1-ferrocenylethylamine and, in a second step, a C—C- or C—Si-bond to be selectively produced on the other cyclopentadienyl ring. However, only this method enables a series of valuable intermediates for ferrocenyldiphosphines and their metal complexes to be prepared. In this way it is also possible to obtain, in very good yields, ferrocenyldiphosphines which are functionalized on only one cyclopentadienyl radical and which can be bound selectively via these functional groups to inorganic or organic support materials.

The invention further provides compounds of the formula I

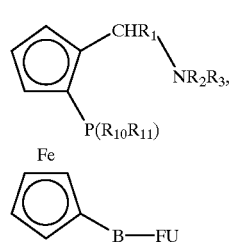

(I)

R$_1$ is C$_1$–C$_8$alkyl, phenyl or phenyl substituted by from 1 to 3 C$_1$–C$_4$alkyl or C$_1$–C$_4$alkoxy;

R$_2$ and R$_3$ are, independently of one another, hydrogen, C$_1$–C$_{12}$alkyl or C$_5$–C$_{12}$cycloalkyl, OH- or NH$_2$-substituted C$_1$–C$_{12}$alkyl or together a cyclic C$_2$–C$_8$alkylene group; and R$_{10}$, R$_{11}$, B and FU are as defined and preferred above.

Alkyl radicals R$_2$ and R$_3$ can be linear or branched; examples of C$_1$–C$_8$alkyl are mentioned above and to these may be added the various isomers of nonyl, decyl, undecyl and dodecyl. R$_2$ and R$_3$ can also be bound to one another and form a cyclic alkyl group. Examples are pyrrolidine and piperidine.

R$_2$ and R$_3$ are preferably, independently of one another, hydrogen, methyl, ethyl or propyl, hydroxypropyl, aminopropyl or together pentylene, particularly preferably simultaneously methyl.

The compounds of the formula I are prepared starting from compounds of the formula II

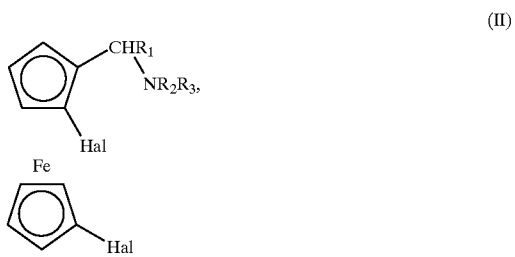

(II)

in which the radicals R$_1$, R$_2$ and R$_3$ are as defined and preferred above and Hal is halogen, preferably F, Cl, Br or I. The compounds of the formula II can here be prepared by analogous methods in a manner known per se, as is described, for example, by R. F. Kovar et al., Organometal. Chem. Syn., 1 (1970/1971) 173–181 for the reaction of dilithiated compounds with halogenating agents or by T. Hayashi et al. Bull Chem. Soc. Jpn., 53 (1980) 1138–1151 for stereoselective lithiation.

In this preparation, the ferrocene compound in an inert organic solvent is first allowed to react with one equivalent of alkyllithium and subsequently in the presence of an amine complexing agent for Li with a second equivalent of alkyllithium and is subsequently reacted with a halogenating agent.

An example of an amine complexing agent for Li is N,N,N,N-tetramethylethylenediamine. In the context of the present invention, alkyllithium is preferably t-butyllithium, sec-butyllithium or n-butyllithium.

Halogenating agents are known from the general prior art for many reactions. By way of example, some are also mentioned in Gmelin, Handbuch der Anorganischen Chemie, Eisen-Organische Verbindungen, Part A, Ferrocene 7, eighth edition, Springer Verlag 1980, pages 128–136.

The halogenating agent is preferably selected from the group consisting of Cl$_2$, hexachloroethane, 1,2-dichlorotetrafluoroethane, toluene-4-sulfonyl chloride, Br$_2$, 1,2-dibromotetrachloroethane, 1,2-dibromotetrafluoroethane, toluene-4-sulfonyl bromide, 2,3-dimethyl-2,3-dibromobutane, I$_2$, 1,2-diiodotetrafluoroethane, perfluoropropyl iodide, perfluoroethyl iodide, toluene-4-sulfonyl iodide or perfluoromethyl iodide.

The compounds of the formula II can, in a next step in an inert organic solvent, be treated with alkyllithium and activated for the next reaction. Subsequently, an organic solution of a compound of the formula III ClP(R$_{10}$R$_{11}$) (III) can be added and the mixture allowed to react further to give a compound of the formula V

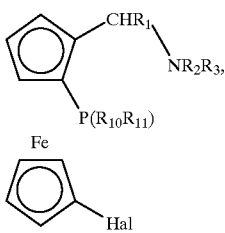

(V)

$R_1$, $R_2$, $R_{10}$, $R_{11}$ and Hal are as defined and preferred above.

The replacement of the halogen atom surprisingly proceeds virtually exclusively on the cyclopentadienyl ring which bears the second substituent (alkylamine). This process therefore enables unsymmetric ferrocenes to be obtained regioselectively in good yield, which is of great importance from the point of view of industrial production.

The compound of the formula III is preferably added at a temperature of from −90 to +20° C.

The invention further provides a process for preparing a compound of the formula I,

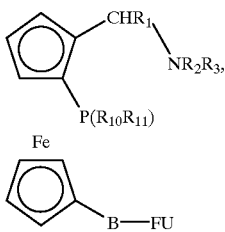

(I)

which comprises
a) reacting a compound of the formula V with alkyllithium,

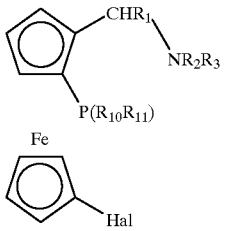

(V)

b) subsequently either
b1) allowing the product to react with a C-electrophilic compound which forms a functional group FU or
b2) allowing the product to react with an electrophilic compound which forms a C- or Si-bonded bridge B and a functional group FU and
c) if desired, converting the functional group FU into another functional group, where the radicals $R_1$, $R_2$, $R_3$, $R_{10}$ and $R_{11}$ are as defined and preferred above; and
aa) B is a direct bond and FU is a functional group bound via a carbon atom to the cyclopentadienyl; or
bb) B is a bridging group bound via a carbon atom or a silicon atom to the cyclopentadienyl and FU is a functional group.

The reaction steps a) and b) are preferably carried out in an inert aprotic solvent at a temperature of from −90° to +30° C.

Examples of aprotic solvents are given above.

The reaction step a) is particularly preferably carried out at a temperature of from −30° to 0° C.

In reaction step b), the electrophilic compound is particularly preferably added at a temperature of from −30° to 0° C. and the reaction mixture is then warmed to room temperature.

Examples of compounds having an electrophilic carbon atom are aliphatic, cycloaliphatic, aromatic or mixed aliphatic, cycloaliphatic and aromatic ketones, aliphatic, cycloaliphatic or aromatic aldehydes, aliphatic, cycloaliphatic or aromatic carboxylic acids, $CO_2$, carboxamides, carboxylic esters, nitriles or acid chlorides.

Examples of such compounds are: $R_aR_b$—C(O), $R_a$—CN, $R_a$—C(O)N(($C_1$–$C_{12}$)alkyl)$_2$, $R_a$—C(O)—O—($C_1$–$C_{12}$)alkyl groups, $CO_2$, dimethylformamide, formaldehyde, cyclic ethers such as oxacyclobutane, oxacyclopropane, $C_2$–$C_{12}$alkyl-oxacyclopropane or cyclic amines such as aziridine. $R_a$ and $R_b$ are, independently of one another, unsubstituted linear or branched $C_1$–$C_{12}$alkyl, $C_2$–$C_{12}$alkenyl, $C_2$–$C_{12}$alkynyl, $C_5$–$C_{12}$cycloalkyl, $C_5$–$C_{12}$cycloalkenyl, phenyl, phenyl-($C_1$–$C_{12}$)alkyl;

or $C_1$–$C_4$alkyl-, $C_1$–$C_4$alkoxy-, halogen- or hydroxy-substituted $C_1$–$C_{12}$alkyl, $C_2$–$C_{12}$alkenyl, $C_2$–$C_{12}$alkynyl, $C_5$–$C_{12}$cycloalkyl, $C_5$–$C_{12}$cycloalkenyl, phenyl, phenyl-($C_1$–$C_{12}$)alkyl.

Use of halogen- or hydroxy-substituted $C_1$–$C_{12}$alkyl, $C_2$–$C_{12}$alkenyl, $C_2$–$C_{12}$alkynyl, $C_5$–$C_{12}$cycloalkyl, $C_5$–$C_{12}$cycloalkenyl, phenyl, phenyl-($C_1$–$C_{12}$)alkyl or, for example, of epichlorohydrin, glycidol, glycidyl ethers such as biphenol-A diglycidyl ether gives compounds which contain, in addition to the functional group FU, a further functional group in the bridging group B.

Preferred compounds having an electrophilic centre are: oxacyclobutane, dimethylformamide, paraformaldehyde, 4-chlorobutyraldehyde, $C_1$–$C_{12}$alkyl aldehydes such as acetaldehyde, propionaldehyde, butyraldehyde, valeraldehyde, caproaldehyde, heptanal, octanal, nonanal, decanal, undecanal, dodecanal, aromatic aldehydes such as benzaldehyde, 4-(2-chloroethyl)benzaldehyde, tolualdehyde, anisaldehyde, salicylaldehyde, vanillin, aliphatic ketones such as acetone, methyl ethyl ketone, cyclohexanone, cyclohexanedione, aromatic or mixed aromatic-aliphatic ketones such as acetophenone or benzophenone, alkyl 4-(2-chloroethyl)benzoates, 4-(2-chloroethyl)benzamides, 4-(2-chloroethyl)benzonitrile.

The compounds of the formula I are precursors for ferrocenyldiphosphines of the formula VI

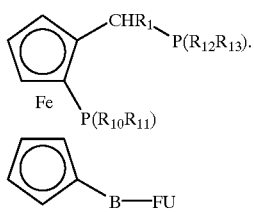

(VI)

For this conversion, a compound of the formula I is reacted with a compound of the formula H—P($R_{12}R_{13}$) in acetic acid, where $R_{12}$ and $R_{13}$ are as defined and preferred above. An analogous process is known and described, for example, in EP-A-612 758.

It is also possible to carry out the individual process steps in another order.

The invention therefore further provides a process for preparing a compound of the formula VI

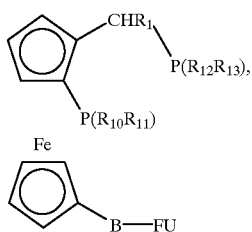

(VI)

which comprises a) reacting a compound of the formula V with a compound of the formula H—P(R$_{12}$R$_{13}$) in acetic acid to give a compound of the formula VII

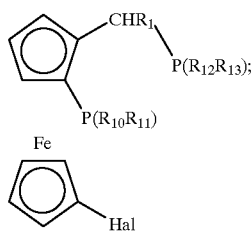

(VII)

b) then further reacting the compound of the formula VII with alkyllithium;

c) subsequently either c1) allowing the product to react with a C-electrophilic compound forming a functional group FU or c2) allowing the product to react with an electrophilic compound which forms a C- or Si-bonded bridge B and a functional group FU and d) if desired, converting the functional group FU into another functional group, where the radicals R$_1$, R$_{10}$, R$_{11}$, R$_{12}$ and R$_{13}$ are as defined and preferred above and aa) B is a direct bond and FU is a functional group bound via a carbon atom to the cyclopentadienyl; or bb) B is a bridging group bound via a carbon atom or a silicon atom to the cyclopentadienyl and FU is a functional group.

The reaction steps b) and c) are preferably carried out in an inert aprotic solvent at a temperature of from −90° to +30° C.

Examples of aprotic solvents are ethers such as diethyl ether or tetrahydrofuran, hydrocarbons such as hexane, heptane or pentane, aromatics such as toluene, benzene, xylene, amides such as dimethylacetamide, ketones such as acetone or methyl ethyl ketone.

The reaction step b) is particularly preferably carried out at a temperature of from −30° to 0° C.

In reaction step c), the electrophilic compound is particularly preferably added at a temperature of from −30° to 0° C. and the reaction mixture is then warmed to room temperature.

The compounds of the formula I or VI can be obtained as racemates, pure enantiomers or mixtures of enantiomers. Carrying out the synthesis starting from enantiomerically pure compounds of the formula II or V results in the highly preferential formation of only one of the two possible diastereomers of compounds of the formula I or VI.

If the starting materials are racemates or optically active mixtures, these can be separated into the stereoisomers by known methods, with chromatographic methods being generally preferred. In particular, the optical isomers of the compounds of the formula VI are valuable starting materials for preparing immobilized, extractable and adsorbable hydrogenation catalysts.

The isolation and purification of the compounds is carried out by methods known per se, for example distillation, extraction, crystallization and/or chromatographic methods.

The invention further provides metal complexes of the formulae VIIIa and VIIIb of d-8 metals with the compounds of the formula VI

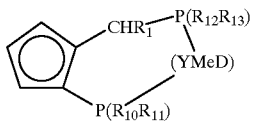

(VIIIa)

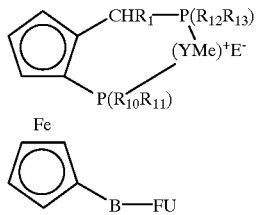

(VIIIb)

where R$_1$, R$_{10}$, R$_{11}$, R$_{12}$, R$_{13}$, B and FU are as defined and preferred above;

Y is two monoolefin ligands or one diene ligand;

Me is a d-8 metal;

D is —Cl, —Br, —I;

E$^-$ is the anion of an oxyacid or complex acid.

Me is preferably Rh, Ir or Pd and particularly preferably Rh or Ir.

Preference is given to metal complexes in which Y is 1,5-hexadiene, 1,5-cyclooctadiene or norbornadiene.

In the preferred metal complexes, E$^-$ is ClO$_4^-$, CF$_3$SO$_3^-$, HSO$_4^-$, BF$_4^-$, B(phenyl)$_4^-$, PF$_6^-$, SbCl$_6^-$, AsF$_6^-$ or SbF$_6^-$.

The invention further provides a process for preparing the metal complexes of the formula VIIIa or VIIIb, which comprises reacting a compound of the formula VI with a metal compound of the formula [Me(Y)D]$_2$ or Me(Y)$_2^+$E$^-$, in which Me is a d-8 metal, preferably rhodium or iridium, and Y, D and E$^-$ are as defined and preferred above.

The reaction is advantageously carried out in an inert gas atmosphere, for example argon, and advantageously at temperatures of from 0 to 40° C., preferably at room temperature. Use is advantageously also made of a solvent or mixture of solvents, for example hydrocarbons (benzene, toluene xylene), halogenated hydrocarbons (methylene chloride, chloroform, carbon tetrachloride, chlorobenzene), alkanols (methanol, ethanol, ethylene glycol monomethyl ether) and ethers (diethyl ether, dibutyl ether, ethylene glycol dimethyl ether) or mixtures thereof.

The compounds of the formulae VIIIa and VIIIb are themselves homogeneous catalysts which can be used for hydrogenations of unsaturated organic compounds.

Methods of preparing such metal complexes and metal complexes with other phosphine ligands are described, for example, in EP-A-612 758.

The metal complexes are preferably used for the asymmetric hydrogenation of prochiral compounds having carbon—carbon or carbon-hetero atom multiple bonds, in particular double bonds, especially the Ir complexes for hydrogenation of unsymmetric ketimines.

Such hydrogenations using soluble homogeneous ferrocenyldiphosphine metal complexes are likewise described, for example, in EP-A-612 758.

The invention further provides inorganic or organic polymeric support materials to which are bound the ferrocenyldiphosphines of the formula VI

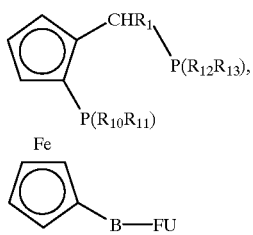

(VI)

wherein the ferrocenyldiphosphines are bound via the functional group FU to the organic or polymeric organic support material, where the radicals B, FU, $R_1$, $R_{10}$, $R_{11}$, $R_{12}$ and $R_{13}$ are as defined and preferred above.

The ferrocenyldiphosphines of the formula VI are preferably bound to the surface of these support materials. This has the advantage that all catalytically active groups are accessible and no inclusions occur. As a result, less catalyst-containing support material has to be used in the hydrogenation.

If the compounds of the formula VI are bound to inorganic support materials, the functional group FU is advantageously first reacted with a compound of the formula (IX)

in which $R_{14}$ $C_1$–$C_{12}$alkylene, $R_{15}$ is $C_1$–$C_{12}$alkyl or $OR_{15}$ and n is 0, 1 or 2; in this case, FU is OH, $NH_2$ or NH—($C_1$–$C_{12}$)alkyl. This results in compounds of the formula (Ia), (Ib) or (Ic)

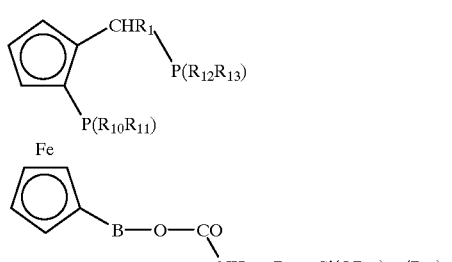

(Ia)

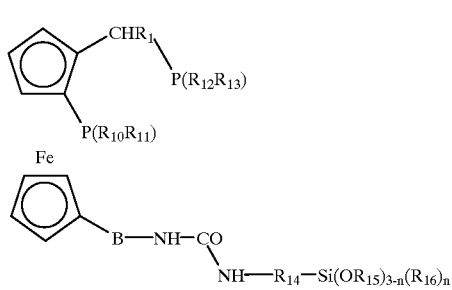

(Ib)

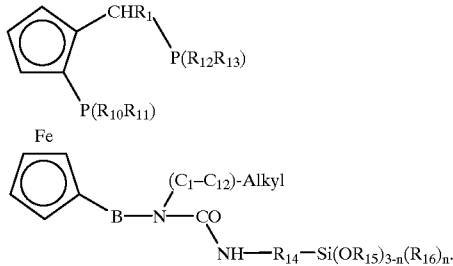

(Ic)

The compounds of the formulae Ia, Ib and Ic are intermediates for preparing ferrocenyldiphosphines bound to inorganic support materials.

The invention further provides a solid organic material of the formula (Xa), (Xb) or (Xc) which has a ferrocenyldiphosphine ligand

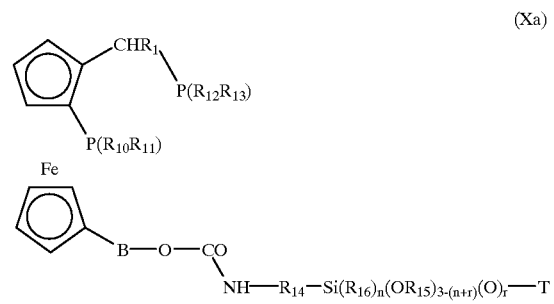

(Xa)

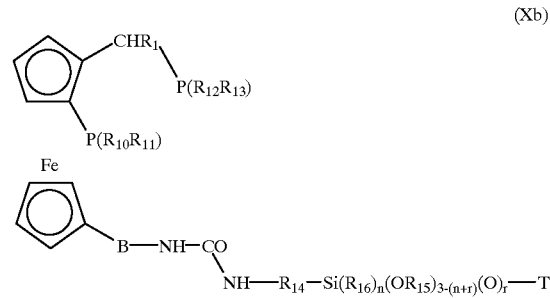

(Xb)

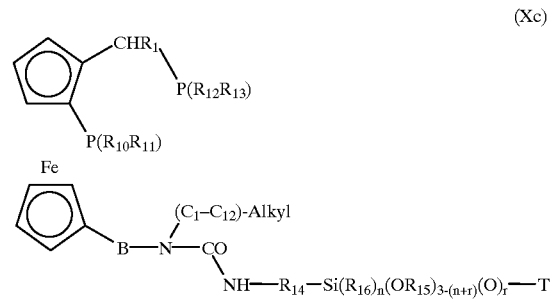

(Xc)

bound to its surface, where $R_1$, $R_{10}$, $R_{11}$, $R_{12}$, $R_{13}$, $R_{14}$, $R_{15}$, $R_{16}$, B and n are as defined above and T is a solid organic support material; where when n is 0, r is 1, 2 or 3,
when n is 1, r is 1 or 2, and
when n is 2, r is 1.

The solid support material T can be a silicate or a semimetal or metal oxide or a glass and is preferably in the form of a powder having a mean particle diameter of from 10 nm to 2000 μm, preferably from 10 nm to 1000 μm and particularly preferably from 10 nm to 500 μm. The particles can be either compact or porous. Porous particles preferably have high internal surface areas, for example from 1 to 1200 m², preferably from 30 to 600 m². Examples of oxides and silicates are $SiO_2$, $TiO_2$, $ZrO_2$, MgO, NiO, $WO_3$, $Al_2O_3$, $La_2O_3O$, silica gels, clays and zeolites. Preferred support materials are silica gels, aluminium oxide, titanium oxide or glass and mixtures thereof. An example of a glass as support material is "controlled pore glass" which is commercially available.

The material of the formula Xa, Xb or Xc can be prepared by a method analogous to that described in EP-A-0 496 699 by allowing a compound of the formula Ia, Ib or Ic in an inert organic solvent to react with a solid inorganic support material T, advantageously under inert gas, for example argon, and at a temperature of from 40 to 180° C. The solid material is advantageously placed in a reaction vessel, a solution of the compound of the formula Ia, Ib or Ic is added and the mixture is stirred at elevated temperature, for example from 50 to 110° C. Suitable solvents have been mentioned above, particularly preferred solvents are toluene and xylene. The product can be isolated either by decantation, centrifugation or filtration. The residue can be purified by washing with an alkanol and can then be dried in a high vacuum.

the trialkoxysilane compounds of the formulae Ia, Ib and Ic can also be converted directly into polysiloxanes by a sol-gel process. Such reactions have been described, for example, by U. Deschler et al. in *Angew. Chem.* 98, (1986), 237–253.

The present invention further provides organic polymeric support materials to which ferrocenyldiphosphines of the formula VI

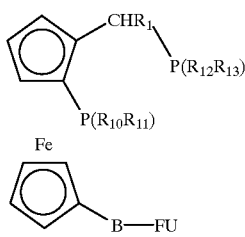

(VI)

are bound via the functional group FU, where the radicals $R_1$, $R_{10}$, $R_{11}$, $R_{12}$, $R_{13}$, B and FU are as defined and preferred above.

The organic polymeric support materials can be uncrosslinked thermoplastic, crosslinked or structurally crosslinked polymers.

The polymers can be either polymers of olefinically unsaturated monomers such as polyolefins, polyacrylates, polyisoprenes, polybutadiene, polystyrene, polyphenylene, polyvinyl chloride, polyvinylidene chloride or polyallyl compounds. However, they can also by polyaddition compounds such as polyurethanes or polyethers. Examples of polycondensed products are polyesters and polyamides.

The monomers forming the polymer are preferably selected from the group consisting of styrene, p-methylstyrene or α-methylstyrene. Another preferred group of polymers is formed by monomers which are derived from α,β-unsaturated acids, their esters or amides.

Particular preference is given to the monomers from the group consisting of acrylates and their $C_1$–$C_4$alkyl esters, methacrylates and their $C_1$–$C_4$alkyl esters, acrylamide and acrylonitrile.

A likewise preferred group is derived from monomers selected from the group consisting of acrylates and their $C_1$–$C_4$alkyl esters, methacrylates and their $C_1$–$C_4$alkyl esters, which contain as structural element a bonded hydroxyl group or a bonded primary or secondary amino group as functional group in the ester group.

The bonding of the ferrocenyldiphosphines of the formula VI to the polymeric support materials can be carried out in various ways.

In a preferred group of polymer-bonded compounds of the formula VI, FU is an olefinically unsaturated radical which is bound to the bridging group B via an ester group OC(O)—$CR_c$=$CR_dR_e$ or an amide group $OC(NR_f)$—$CR_c$=$CR_dR_e$, in which $R_c$, $R_d$, $R_e$ and $R_f$ are, independently of one another, hydrogen or $C_1$–$C_6$alkyl, and these are used as comonomers in the free-radical polymerization of further olefinically unsaturated monomers. Examples and preferences for further monomers are mentioned above.

For the remaining radicals of the compounds of the formula VI, the abovementioned meanings and preferences apply.

The free-radical polymerization is carried out in a known manner and gives a copolymer in which the ferrocenyldiphosphine ligands are present in bound form.

Another possibility is a polymer-analogous reaction as has been described by R. Cullen et. al. in *J. of Organometallic Chemistry*, 333 (1987), 269–280.

In a first step, a compound of the formula VII

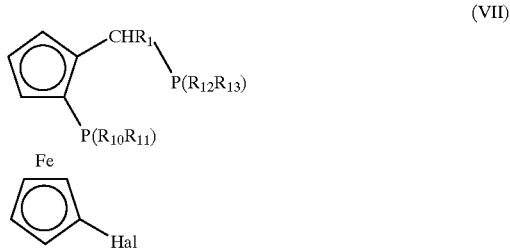

(VII)

is allowed to react with one equivalent of alkyllithium, as described above, and the reaction product is reacted in a next step with a polystyrene whose styrene groups have been partially oxidized to the aldehyde. This gives a polystyrene modified with ferrocenyldiphosphine ligands.

A further preferred polymer-analogous reaction with polystyrene is first allowing the polystyrene to react with alkyllithium and, in a second step, reacting the reaction product with a compound of the formula (VI) in which the functional group FU is (O)C—H or (O)C—($C_1$–$C_{12}$)alkyl. This likewise gives a polystryene modified with ferrocenyldiphosphine ligands.

Polymer-analogous reactions are also possible with polycondensates such as polyesters and polyamides which contain, either in a side chain or directly in the polymer chain, a further functional group capable of condensation. Examples are hydroxyl-containing polyester or polyethers which can be reacted with compounds of the formula VI in which the functional group FU is in this case preferably COO($C_1$–$C_{12}$)alkyl or COCl.

A further group of preferred polymers which are suitable for polymer-analogous reactions consists of monomers which comprise vinyl alcohol as homopolymer or vinyl alcohol as copolymer with vinyl acetate, stearate, benzoate, maleate, vinyl butyral, allyl phthalate, allylmelamine.

The compounds of the formula VI in which FU is (O)CH and B is as defined and preferred above can be reacted in a known manner with polyvinyl alcohols, with the bonding occurring by means of acetal or ketal formation.

Likewise preferred polymers are formed from phenol and a $C_1$–$C_4$aldehyde, particularly preferably from phenol and formaldehyde. The polymers are known as phenol-formaldehyde resins, in particular as novolaks, and are commercially available.

Another preferred group of polymers which are suitable form polymer-analogous reactions in derived from bisglycidyl ethers and diols. These polymers are hydroxyl-functional polyethers which are prepared, for example, from bisglycidyl ethers and bisphenol A.

These polyepoxides can be built up of diepoxide comonomers having preferably from 6 to 40 and particularly preferably from 8 to 30 carbon atoms and dioles are comonomers having preferably from 2 to 200 and particularly preferably from 2 to 50 carbon atoms. A preferred group derived therefrom is made up of monomers which build up a polymer from cyclic $C_3$–$C_6$ethers or $C_2$–$C_6$alkylene glycols with bisglycidyl ethers. The bisglycidyl ethers can be aromatic, aliphatic or cycloaliphatic.

Further preferred polymers having hydroxyl groups as functional groups are polysaccharides.

Particular preference is given to partial cellulose acetates, propionates or butyrates, partial cellulose ethers, starch, chitin and chitosan.

Further polymers are derived from polymers containing reducible groups such as nitrile groups, ketone groups, carboxylic esters and carboxamides.

It is also possible to use polymers which are insoluble in the reaction medium and have been functionalized on the surface with hydroxyl or amine groups by means of a chemical or physical process. For example, partly unsaturated polymers can be provided on the surface with hydroxyl groups by oxidation, e.g. using hydrogen peroxide. Another possibility is plasma treatment in, for example, an oxygen, nitrogen or ammonia atmosphere. The polymers are preferably in the form of powder. Among these support materials, particular preference is given to polystyrene which has been subsequently functionalized with hydroxyl, amino or hydroxymethyl groups using known methods.

A particularly preferred group is formed by a polymeric organic material comprising structural repeating units of the formula XIa or XIb

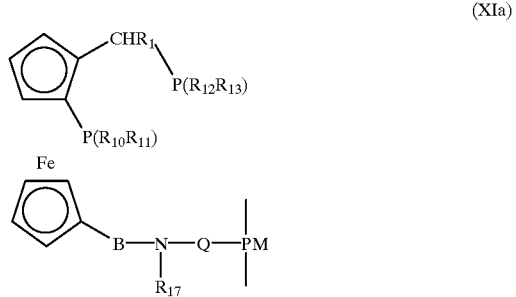

(XIa)

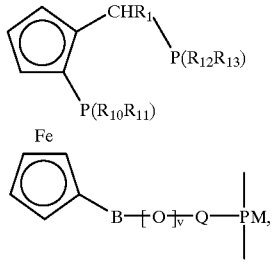

(XIb)

B, $R_1$, $R_{10}$, $R_{11}$, $R_{12}$ and $R_{13}$ are as defined and preferred above;

$R_{17}$ is H or $C_1$–$C_{12}$alkyl;

v is 0 or 1;

Q is a bridging group formed from a monoisocyanate or diisocyanate; and

PM is the radical of a polymer-forming monomer which contains, directly or in a side chain, a bonded hydroxyl group or a bonded primary or secondary amino group as functional group which is bound to the diphosphine via a bridging group Q formed from mono- or diisocyanate.

The diphosphine radicals of the formula (XIa) or (XIb) can be in the form of enantiomer mixtures; preference is given to polymers containing radicals of the formula VI in the form of the optically active R,R—, S,S—, R,S— or S,R isomers, based on the position of the phosphine groups.

The choice of the mono- or diisocyanate for forming the bridging group Q is not critical per se. In particular, the bridging group Q can be formed by at least 2 carbon atoms. Suitable and individually available diisocyanates are described, for example, in Houben Weyl, Makromolekulare Stoffe, Volume E 20, pages 1587 to 1987 edition.

Preference is given to diisocyanates whose bridging group Q is formed by a linear or branched aliphatic $C_2$–$C_{20}$alkyl which may be unsubtituted or monosubstituted or polysubstituted by $C_1$–$C_6$alkyl or/and $C_1$–$C_6$alkoxy, a $C_3$–$C_8$cycloalkyl or heterocycloalkyl which may be unsubstituted or monosubstituted or polysubstituted by $C_1$–$C_6$alkyl or/and $C_1$–$C_6$alkoxy, a linear or branched aliphatic $C_2$–$C_{20}$alkyl which may be unsubstituted or substituted by $C_1$–$C_6$alkyl or/and $C_1$–$C_6$alkoxy and is interrupted by unsubstituted or $C_1$–$C_6$alkyl- or/and $C_1$–$C_6$alkoxy-substituted $C_3$–$C_8$cycloalkyl or heterocycloalkyl, a phenyl, naphthyl, biphenyl or $C_3$–$C_{10}$heteroaryl radical which may be unsubsituted or monosubstituted or polysubstituted by $C_1$–$C_6$alkyl or/and $C_1$–$C_6$alkoxy, or a linear or branched aliphatic $C_2$–$C_{20}$alkyl which may be unsubstituted or subsituted by $C_1$–$C_6$alkyl or/and $C_1$–$C_6$alkoxy and is interrupted by phenyl, naphthyl or $C_3$–$C_{10}$heteroaryl.

Heterocycloalkyl is, for example, pyrrolidine, piperidine, morpholine, oxazolidine, dioxolane or an isocyanuric triester group.

Heteroaryl is, for example, pyridine, pyrimidine, pyrrole, furan, imidazole, pyrazole or triazine.

Particularly preferred are diisocyanates such as 1,6-bis[isocyanato]hexane, 5-isocyanato-3-(isocyanatomethyl)-1,1,3-trimethylcyclohexane, 1,3-bis[5-isocyanato-1,3,3-trimethylphenyl]-2,4-dixoo-1,3-diazetidine, 3,6-bis-[9-isocyanatononyl]-4,5-di-(1-heptenyl)cyclohexene, bis[4-isocyanatocyclohexyl]methane, trans-1,4-bis[isocyanato]cyclohexane, 1,3-bis[isocyanatomethyl]benzene, 1,3-bis[1-isocyanato-1-methylethyl]benzene, 1,4-bis[2- isocyanatoethyl]cyclohexane, 1,3-bis-[isocyanatomethyl] cyclohexane, 1,4-bis[1-isocyanato-1-methylethyl]benzene, bis[isocyanato]isododecylbenzene, 1,4-bis[isocyanato] benzene, 2,4-bis[isocyanato]toluene, 2,6-bis[isocyanato] toluene, 2,4-/2,6-bis[isocyanato]toluene, 2-ethyl-1,2,3-tris [3-isocyanato-4-methylanilinocarbonyloxy]propane, N,N'-bis[3-isocyanato-4-methylphenyl]urea, 1,4-bis[3-isocyanato-4-methylphenyl]-2,4-dioxo-1,3-diazetidine, 1,3, 5-tris[3-isocyanato-4-methylphenyl]-2,4,6-trioxohexahydro-1,3,5-triazine, 1,3-bis[3-isocyanato-4-methylphenyl]-2,4,5-trioxoimidazolidine, bis[2-isocyanatophenyl]methane, (2-isocyanatophenyl)(4-isocyanatophenyl)methane, bis[4-isocyanatophenyl] methane, 2,4-bis[4-isocyanatobenzyl]-1-isocyanatobenzene, [4-isocyanato-3-(4-isocyanatobenzyl)phenyl][2-isocyanato-5-(4-isocyanatobenzyl)phenyl]methane, tris-[4-isocyanatophenyl]methane, 1,5-bis[isocyanato]naphthalene and 4,4'-bis[isocyanato]-3,3'-dimethylbiphenyl and also 1,1'-carbonyldiimidazole.

Very particularly preferred are diisocyanates such as 1,6-bis[isocyanato]hexane, 5-isocyanato-3-(isocyanatomethyl)-1,1,3-trimethylcyclohexane, 2,4-bis [isocyanato]toluene, 2,6-bis[isocyanato]toluene, 2,4-/2,6-bis[isocyanato]toluene and bis [4-isocyanatophenyl] methane and also 1,1'-carbonyldiimidazole.

The hydroxyl-containing polymers of the invention can be uncrosslinked thermoplastic, crosslinked or structurally crosslinked polymers. Examples of hydroxyl-containing polymers have been mentioned above.

The polymers to be used according to the invention are known per se, some are commercially available or they can be prepared by known polymerization methods or by subsequent modification of polymers.

The polymeric organic materials preferably have a molecular weight of from 5000 to 5 000 000 Dalton, particularly preferably from 50 000 to 1 000 000 Dalton.

A preferred subgroup of polymeric organic materials consists of highly crosslinked macroporous polystyrene or polyacrylate.

Another preferred group of polymers consists of weakly crosslinked polystyrene. An example is polystyrene crosslinked by 1–5% of divinylbenzene.

The particle size of the polymeric organic materials is preferably from 10 μm to 2000 μm. The highly crosslinked polymeric organic materials preferably have a specific surface area of from 20 m²/g to 1000 m²/g, particularly preferably from 50 m²/g to 500 m²/g, determined by the BET method.

The polymeric support material of formula XIa or XIb can be prepared by A) in a first step, completely or partially reacting a polymer comprising structural repeating units of at least one monomer which contains, either directly in the polymer backbone or in a side chain, a bonded hydroxyl group or a bonded primary or secondary amino group as functional group with a diiosocyanate forming a bridging group Q in an inert organic solvent and, in a second step, reacting the product with the diphosphine of the formula VI; or B) in a first step, completely or partially reacting a diphosphine of the formula VI with a diisocyanate forming a bridging group Q in an inert organic solvent and, in a second step, completely or partially reacting the product with a polymer comprising structural repeating units of at least one monomer which contains a bonded hydroxyl group or a bonded primary or secondary amino group as functional group and C) if desired, crosslinking remaining free isocyanate groups with a $C_2$–$C_{24}$diol or $C_2$–$C_{24}$diamine or reacting them with a $C_2$–$C_{12}$alcohol or $C_2$–$C_{12}$amine.

If crosslinked polymers are prepared, preference is given to crosslinking from 0.01 to 10 mol % of the total isocyanate groups present.

The process is preferably carried out in a polar or non-polar aprotic solvent; the solvent is particularly preferably a halogenated hydrocarbon, an ester, a ketone, an acid amide, an ether, dimethyl sulfoxide or an unsubstituted or substituted hydrocarbon such as xylene, toluene, benzene or chlorobenzene.

The reaction of the diisocyanate forming a bridging group Q with the amine or hydroxyl groups of the polymer and the diphosphine can be carried out at room temperature or elevated temperature, for example from 30° to 100° C., by methods known in the literature. The subsequent introduction, for example, of a hydroxy group into highly crosslinked polystyrene can be carried out by known methods. The polymer is first chloromethylated as described in *J. Mol. Catal.* 51 (1989), 13–27 subsequently saporified by the method given by J. M. Frechet et al. in *Polymer,* 20 (1979) 675–680.

The subsequent modification can also be carried out in bulk, for example using a plasma method. Chemical methods in solution or in emulsion are also possible.

Insoluble polymers are milled beforehand by known methods and brought to the desired particle size.

The invention further provides d-8 metal complexes, preferably rhodium or iridium metal complexes, of inorganic or organic polymeric support materials to which ferrocenyldiphosphines of the formula VI

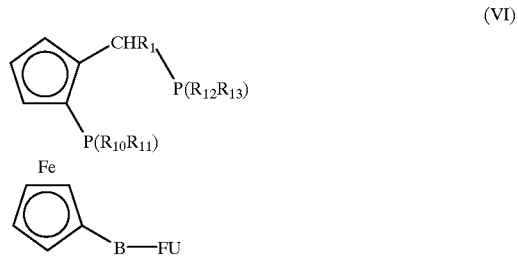

(VI)

are bound via the functional group FU, where the radicals B, FU, $R_1$, $R_{10}$, $R_{11}$, $R_{12}$ and $R_{13}$ are as defined and preferred above.

Preference is given to the d-8 metal complexes of the formula XIIa, XIIb, XIIc, XIId, XIIe or XIIf

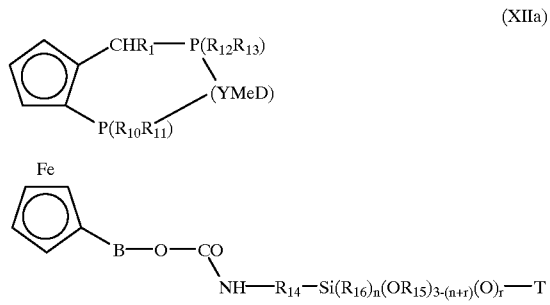

(XIIa)

-continued

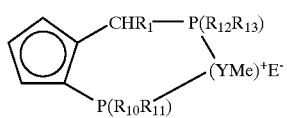

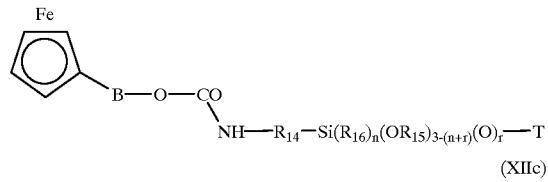

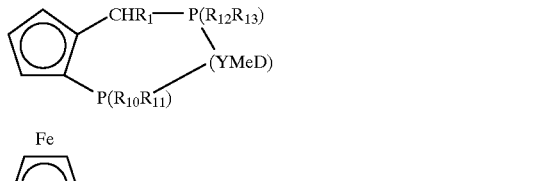

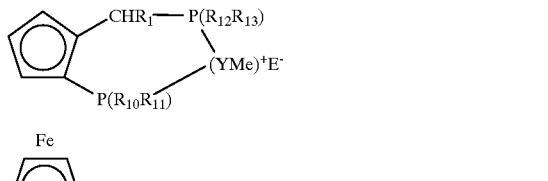

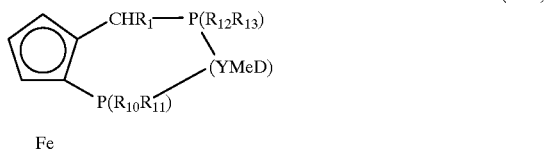

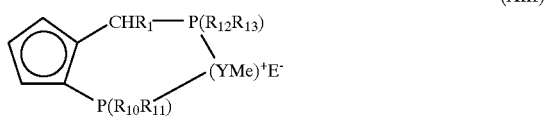

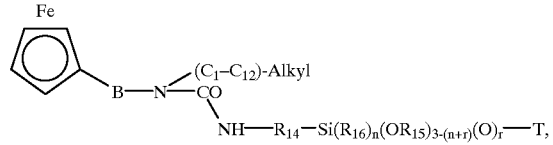

in which $R_1$, $R_{10}$, $R_{11}$, $R_{12}$, $R_{13}$, $R_{14}$, $R_{15}$, $R_{16}$, T, B, FU, n and r are as defined and preferred above;

Y is either two monoolefin ligands or one diene ligand;

Me is a d-8 metal, preferably Ir or Rh;

D is —Cl, —Br, —I;

$E^-$ is the anion of an oxyacid or complex acid.

For Y, D and E, the above preferences apply.

The metal complexes of the formulae XIIa, XIIb, XIIc, XIId, XIIe and XIIf can be prepared by an analogous method, as described in EP-A-0 496 699, and be used for a hydrogenation.

A further preferred group of metal complexes comprising polymeric organic support materials consists of those of the formulae XIIIa, XIIIb, XIIIc and XIIId.

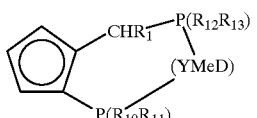

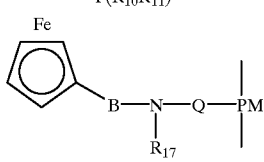

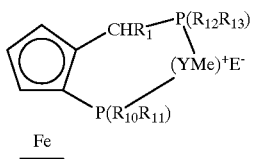

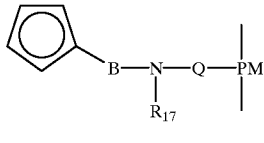

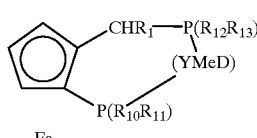

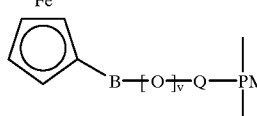

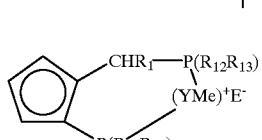

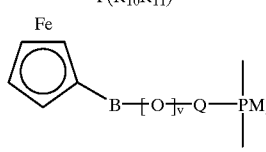

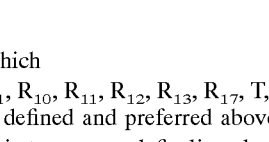

in which $R_1$, $R_{10}$, $R_{11}$, $R_{12}$, $R_{13}$, $R_{17}$, T, B, FU, PM, Q and v are as defined and preferred above;

Y is two monoolefin ligands or one diene ligand;

Me is a d-8 metal, preferably Ir or Rh;

D is —Cl, —Br, —I;

$E^-$ is the anion of an oxyacid or complex acid.

For Y, D and E, the above preferences apply.

The invention further provides a process for preparing a metal complex with the polymeric support material, which comprises reacting a compound of the formula XIa or XIb with a metal compound of the formula $[M(Y)D]_2$ or M(Y)$_2$$^+$E$^-$, in which M is a d-8 metal, preferably rhodium or iridium, and Y, D and E$^-$ are as defined above.

The reaction is advantageously carried out under an inert gas atmosphere, for example argon, and advantageously at temperatures of from 0 to 40° C., preferably at room temperature, if the polymer-bonded diphosphines are soluble. Use is advantageously made of a solvent or mixture of solvents, for example hydrocarbons (benzene, toluene, xylene), halogenated hydrocarbons (methylene chloride, chloroform, carbon tetrachloride, chlorobenzene), alkanols (methanol, ethanol, ethylene glycol monomethyl ether) and ethers (diethyl ether, dibutyl ether, ethylene glycol dimethyl ether) or mixtures thereof.

A precalculated amount of this catalyst solution can be used directly for a hydrogenation reaction. Evaporation of the solvent or addition of a solvent in which the polymer is insoluble also makes it possible to isolate and use the polymer-bonded catalyst in solid form.

In the case of insoluble, partially or highly crosslinked polymer-bonded diphosphines, the metal compound of the formula [M(Y)D]$_2$ or M(Y)$_2$$^+$E$^-$ is first dissolved in a solvent and this solution is added to the dissolved or slurried material. Here, the reaction conditions described above can be employed. The polymer of the invention can either be used directly or be isolated by filtration, purified by washing with the abovementioned solvents and dried under reduced pressure.

The inorganic metal complexes of the invention can also be prepared in situ before a hydrogenation and then used directly as hydrogenation catalysts.

The invention further provides ferrocenyldiphosphine ligands having a molecular weight of preferably less than 5000 Dalton which can be separated off by extraction with mutually immiscible liquids or by adsorption on a support material. In the extraction, preference is given to using two mutually immiscible liquids. When such ligands are used, virtually no metal and ligand losses occur. These extractable or adsorbable catalysts therefore allow, in particular, industrial-scale hydrogenations to be carried out economically.

Suitable mutually immiscible liquids which may be mentioned are, for example, water and water-immiscible organic solvents such as alkanes (for example hexane), chlorinated alkanes (for example methylene chloride, chloroform), aryls (for example toluene, benzene, xylene) or esters (for example ethyl acetate) or organic solvent systems such as fluorinated hydrocarbons and hydrocarbons.

Suitable support materials which may be mentioned are, for example, silica gel, in particular reversed-phase silica gel, polar and nonpolar polymers and ion exchangers (preferably for ligands having charged radicals).

Preference is given those adsorbable or extractable ferrocenyldiphosphine ligands which on one cyclopentadienyl ring have a tertiary phosphine group bound via a methylene group in the 1 position and a directly bound tertiary phosphine group in the 2 position and on the second cyclopentadienyl ring in the 1' position have an extractable or adsorbable radical bound via a silicon or carbon atom.

Suitable extractable or adsorbable radicals are also given in I. T. Horváth et al. in *Science*, Vol. 266, pages 72–75 (1994).

Preferred extractable radicals are, for example, lipophilic radicals derived from alkanes having a molecular weight of from 100 to 2000 Dalton or hydrophilic radicals derived from sugars, polyvinyl alcohols, polyarcylic acids, polyethylene glycols, polyvinyltoluene and polar dendrimers. Fluorinated alkanes are also preferred.

Preferred adsorbable radicals are, for example, lipophilic radicals which are derived from alkanes having a molecular weight of from 100 to 2000 Dalton and fluoroalkanes.

Further examples of extractable or adsorbable radicals are:

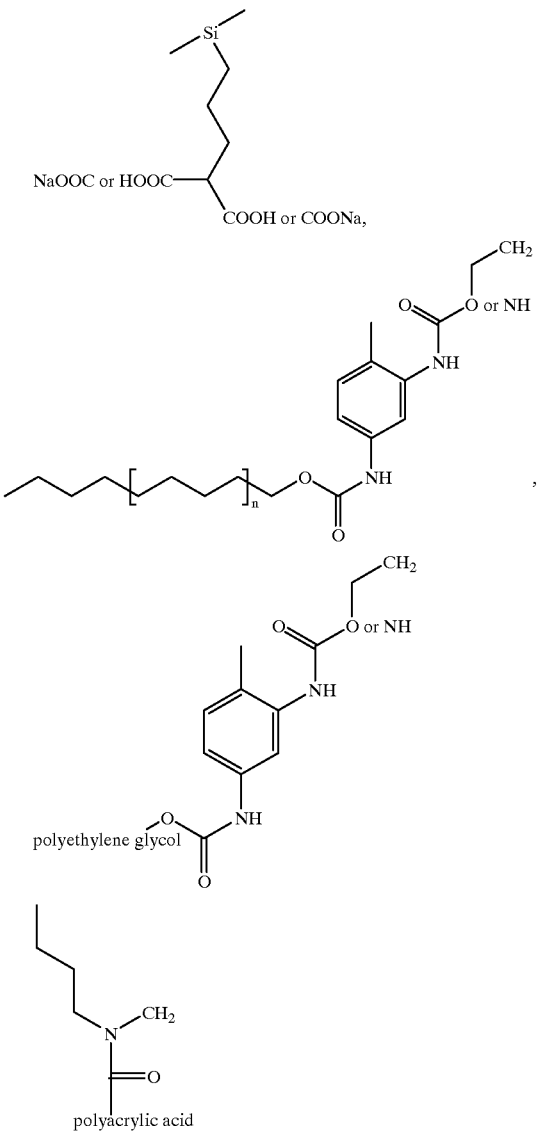

Particularly preferred ferrocenyldiphosphine ligands are compounds of the formulae

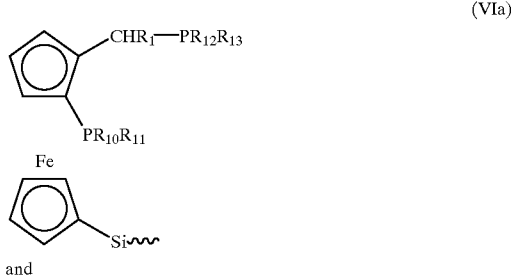

(VIa)

and (VIb)

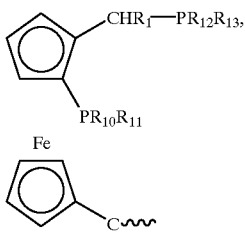

in which

R₁, R₁₀, R₁₁, R₁₂ and R₁₃ are as defined and preferred above;

Si⌇⌇ is a radical which is bound via a silicon atom and makes the compound (VIa) extractable or adsorbable; and

C⌇⌇ is a radical which is bound via a carbon atom and makes the compound (VIb) extractable or adsorbable.

The compounds of the formulae (VIa) and (VIb) include, as in the case of the compounds of the formula (VI), the racemates, pure diastereomers or mixtures of diastereomers.

The radical

Si⌇⌇ bound via a silicon atom preferably corresponds to a radical of the formula

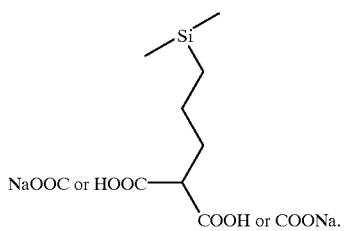

The radical

C⌇⌇ bound via a carbon atom preferably corresponds to a radical of the formula —B—FU, where a) B is a direct bond and FU is a functional group bound via a carbon atom to the cyclopentadienyl, or b) B is a bridging group bound via a carbon atom to the cyclopentadienyl and FU is a functional group Preferred metal complex catalysts containing the ferrocenyldiphosphine (VIa) or (VIb) are compounds of the formulae Xaa, Xbb, Xcc and Xdd

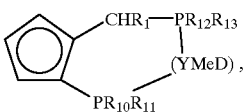
(Xaa)

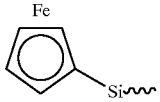

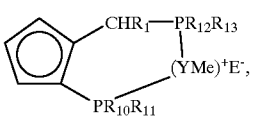
(Xbb)

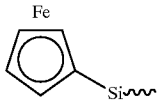

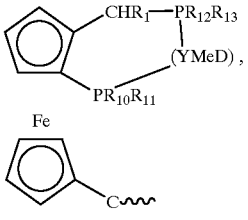
(Xcc)

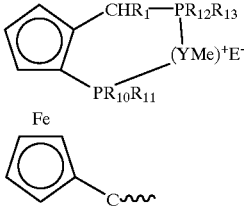
(Xdd)

where R₁, R₁₀, R₁₁, R₁₂, R₁₃,

Si⌇⌇ and C⌇⌇ are as defined and preferred in the description of the ferrocenyl ligands;

Y is either two monoolefin ligands or one diene ligand;

ME is a d-8 metal, preferably Ir or Rh;

D is —Cl, —Br or —I;

E⁻ is the anion of an oxyacid or a complex acid.

Preference is given to metal complexes in which Y is 1,5-hexadiene, 1,5-cyclooctadiene (COD) or norbonradiene.

In the preferred metal complexes, E⁻ is $ClO_4^-$, $CF_3SO_3^-$, $CH_3SO_3^-$, $HSO_4^-$, $BF_4^-$, $B(phenyl)_4^-$, $PF_6^-$, $SbCl_6^-$, $AsF_6^-$ or $SbF_6^-$.

The metal complexes of the invention are vey suitable as catalysts for the hydrogenation of organic double and triple bonds. Examples are compounds containing the groups C=C, C=N, C=O, C=C—n or C=C—O (see example, K. E. König, The Applicability of Asymmetric Homogeneous Catalysis, in James D. Morrison (ed.), *Asymmetric Synthesis*, Vol. 5, Academic Press, 1985). In particular, the metal complexes of the invention are suitable for the enantioselective hydrogenation of compounds containing prochiral carbon—carbon and carbon-heteroatom double bonds. Examples of such compounds are prochiral alkenes, imines and ketones.

After the reaction, the catalysts of the invention can be separated virtually completely from the reaction mixture in a simple manner, for example by decantation, centrifugation, filtration, ultrafiltration, extraction or adsorption, and can be reused. A particular advantage is that they can be reused a plurality of times without significant activity or selectivity losses occurring.

The invention therefore further provides for the use of the novel metal complexes of d-8 metals, preferably rhodium or iridium, as heterogeneous or homogeneous catalysts for the asymmetric hydrogenation of prochiral compounds containing carbon—carbon or carbon-heteroatom double bonds.

The metal complexes are preferably used for the asymmetric hydrogenation of prochiral compounds containing carbon—carbon or carbon-heteroatom double bonds, in particular the Ir complexes for hydrogenating asymmetric ketimines.

The invention further provides a process for the asymmetric hydrogenation of compounds containing carbon—carbon or carbon-heteroatom double bonds, which comprises reacting the compounds at a temperature of from $-20°$ to $80°$ C. and a hydrogen pressure of from $10^5$ to $2 \times 10^7$ Pa in the presence of catalytic amounts of one or more metal complexes of the invention.

Preference is given to hydrogenations of imines using iridium catalysts of the invention.

Iridium catalysts are preferably used in amounts of from 0.0001 to 10 mol %, particularly preferably from 0.001 to 10 mol % and in particular from 0.01 to 5 mol %, based on the imine to be hydrogenated.

A preferred embodiment of the hydrogenation process is obtained when additional use is made of an ammonium or metal chloride, bromide or iodide. The chlorides, bromides and iodides are preferably used in amounts of from 0.01 to 200 mol %, particularly preferably from 0.05 to 100 mol % and in particular from 0.5 to 50 mol %, based on the iridium catalyst. The iodides are particularly preferred. Ammonium is preferably tetraalkylammonium having from 1 to 6 carbon atoms in the alkyl groups and the metal is preferably sodium, lithium or potassium. Particular preference is given to tetrabutylammonium iodide and sodium iodide.

Very particular preference is given to the hydrogenation process in which additional use is made of an acid. This can be an inorganic or preferably organic acid. The acid is preferably used in a molar amount which is at least equal to that of the iridium catalyst (equal catalytic amounts) and can also be used in excess. The excess can even extend to the use of the acid as solvent. Preference is given to using from 0.001 to 50% by weight, in particular from 0.1 to 50% by weight, of acid, based on the amine. In some cases it can be advantageous to use anhydrous acids.

Examples of inorganic acids are $H_2SO_4$, highly concentrated sulfuric acid (oleum), $H_3PO_4$, HF, HCl, HBr, HI, $HClO_4$, $HBF_4$, $HPF_6$, $HAsF_6$, $HSbCl_6$, $HSbF_6$ and $HB(phenyl)_4$. Particular preference is given to $H_2SO_4$.

Examples of organic acids are aliphatic or aromatic, halogenated (fluorinated or chlorinated) or unhalogenated carboxylic acids, sulfonic acids, phosphorus(V) acids (for example phosphonic acids, phosphonous acids) having preferably from 1 to 20, particularly preferably from 1 to 12 and in particular from 1 to 6, carbon atoms. Examples are formic acid, acetic acid, propionic acid, butyric acid, benzoic acid, phenylacetic acid, cyclohexanecarboxylic acid, chloroacetic or fluoroacetic acid, dichloroacetic or difluoroacetic acid, trichloroacetic or trifluoroacetic acid, chlorobenzoic acid, methanesulfonic acid, ethanesulfonic acid, benzenesulfonic acid, p-toluenesulfonic acid, chlorobenzenesulfonic acid, trifluoromethanesulfonic acid, methylphosphnic acid and phenylphosphonic acid.

Preferred acids are acetic acid, propionic acid, trifluoroacetic acid, methanesulfonic acid and chloroacetic acid.

As acids, it is also possible to use acidic ion exchangers of an inorgnaic or organic nature of solid acids.

For the purposes of the invention, solid acids are those which are insoluble or only swellable in the reaction medium. For the purpose of the invention, a solid acid is a solid, finely divided and possibly porous material of which 1 g in 100 ml of water gives a pH of $\leq 5$, preferably $\leq 4$ and particularly preferably $\leq 3$.

In one embodiment, the solid acids can be metal oxide systems in gel form (sol/gel systems), for example $SiO_2$, $GeO_2$, $B_2O_3$, $Al_2O_3$, $TiO_2$, $ZrO_2$ and combinations thereof. If the desired effects are not as strong as expected, a significant improvment can be achieved by treating the sol/gel systems with an acid, preferably an at least dibasic acid such as $H_2SO_4$ or $H_3PO_4$. Other suitable acids are, for example, HCl, HBr, HI, $HClO_4$, $HBF_4$, $HPF_6$, $HAsF_6$, $HSbCl_6$, $HSbF_6$ and $HB(phenyl)_4$, aliphatic and aromatic, halogenated (fluorinated or chlorinated) or unhalogenated carboxylic acids, sulfonic acids, phosphorous(V) acids (for example phosphonic acids or phosphonous acids) having preferably from 1 bis 20, more preferably from 1 to 12 and particularly preferably from 1 to 8, carbon atoms, for example formic acid, acetic acid, propionic acid, butyric acid, benzoic acid, phenylacetic acid, cyclohexanecarboxylic acid, monochloroacetic, dichloroacetic and trichloroacetic acids, monofluoroacetic, difluoroacetic and trifluoroacetic acids, chlorobenzoic acid, methanesulfonic acid, ethanesulfonic acid, benzenesulfonic acid, p-toluenesulfonic acid, chlorobenzenesulfonic acid, trifluoromethanesuflonic acid, methylphosphonic acid and phenylphosphonic acid. Preference is given to $H_2SO_4$.

In a further embodiment, the solid acids can be inorganic or organic ion exchangers which have been treated with at least dibasic acids such as $H_2SO_4$, $H_2S_2O_7$ or $H_3PO_4$. Ion exchangers are known to those skilled in the art and are described, for example, in *Ullmann'Enzyklopädie der Chemischen Technik,* Volume 13, 4th edition, pages 281 to 284. Organic ion exchangers which may be mentioned are, in particular, polymers containing acid groups such as —C(O)OH, —$SO_3H$ or —$PO_3H$ (for example Nation) which are commercially available. Inorganic ion exchangers which may be mentioned are, in particular, the natural and synthetic aluminosilicates, for example zeolites, which are described in *Studies in Surface Science and Catalysis,* Elsevier 1991, Vol. 56, Chapter 2, pages 13 to 33. They are commercially available. Some examples are zeolite ZSM-5, zeolite Y and mordenite.

In another embodiment, the solid acids can be acidic natural or synthetic siliceous minerals which have no ion exchange capabilities or only a limited ion exchange capability. Examples are phyllosilicates and clay minerals, for example montmorillonite, hectorite, vermiculite, kaolinite and illite. The silicates and clay minerals can be additionally impregnated with an acid, preferably an at least dibasic acid such as $H_2SO_4$, $H_2S_2O_7$ and $H_3PO_4$, which may further increase the effect. Other suitable acid have been mentioned above.

In a further embodiment, the solid acids can be heteropolyacids which prferably consist of the elements Mo, V, W, O and H plus B, Si or P as secondary or trace constituents. Such heteropolyacids are known and described, for example, in *Chemtech,* pages 23ff (November 1993) or *Russian Chemicals Reviews, pages* 811ff (1987).

Some examples are $H_3PW_{12}O_{40}$, $H_9PV_6Mo_6O_{40}$, $H_4SiMo_{12}O_{40}$ and $H_5BW_{12}O_{40}$.

In another suitable embodiment, the solid acids are nonacidic, solid, finely divided and possibly porous support materials which are impregnated with an acid. Suitable support materials are, for example, organic polymers such as epoxy resins, urea-aldehyde resins, melamine-aldehyde resins, polystyrene, ABS and polyolefins. Suitable inorganic support materials are, for example, metal and semimetal oxides ($B_2O_3$, $Al_2O_3$, $SiO_2$, $TiO_2$, $ZrO_2$), metal nitrides, metal carbides, minerals such as silicates and ground rock. It is self-evident that the acids must not react with the support materials. Suitable acids have been mentioned above.

Specifically, the process of the invention can be carried out by first preparing the catalyst by, for example, dissolving $(IrDieneCl)_2$ in a solvent or an acid or both, adding a diphosphine and then an alkali metal or ammonium halide and stirring the mixture. $(IrDieneCl)_2$ can also be added as a solid. The solution of the imines is added to this catalyst solution (or vice versa) and, in an autoclave, hydrogen is injected and the protective gas which is advantageously used is thus removed. It is advantageous to avoid keeping the catalyst solution for any length of time and to carry out the hydrogenation of the imines as directly as possible after preparation of the catalyst solution. The reaction mixture is heated at desired and hydrogenated. After the reaction has ended, the mixture is cooled if appropriate and the autoclave is vented. The reaction mixture can be ejected from the autoclave using nitrogen and the hydrogenated organic compound can be isolated and purified in a manner known per se, for example by precipitation, extraction or distillation.

In the hydrogenation of aldimines and ketimines, these can also be formed in situ before or during the hydrogenation. In a preferred embodiment, an amine and an aldehyde or a ketone are mixed, added to the catalyst solution and the aldimine or ketimine formed in situ is hydrogenated. However, it is also possible to initially charge an amine, a ketone or an aldehyde together with the catalyst and to add the ketone or the aldehyde or the amine, either all at once or by metered addition.

The hydrogenation can be carried out continuously or batchwise in various types of reactor. Preference is given those reactors which allow comparatively faithful mixing and good heat removal, for example loop reactors. This type of reactor has been found to be useful particularly when small amount of catalyst are employed.

The process of the invention give the corresponding amines at high chemical conversions in short reaction times; surprisingly good optical yields (EE) of 70% and more are achieved even at relatively high temperatures of above 50° C. and even at high molar ratios of imine to catalyst.

The hydrogenated organic compounds which can be prepared according to the invention, for example the amines, are biologically active substances or intermediates for preparing such substances, in particular in the field of preparing pharmaceuticals and agrochemicals. Thus, for example, O,O-dialkylarylketamine derivatives, in particular those containing alkyl and/or alkoxyalkyl groups, act as fungicides, particularly as herbicides. The derivatives can be amine salts, acid amides, e.g. of chloroacetic acid, tertiary amines and ammonium salts. (see, for example, EP-A-0 077 755 and EP-A-0 115 470).

The present invention further provides metal complex catalysts of ruthernium containing a ferrocenyl ligand of the formula (VI), (VIa) or (VIb)

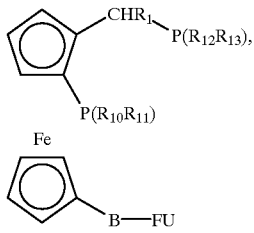

(VI)

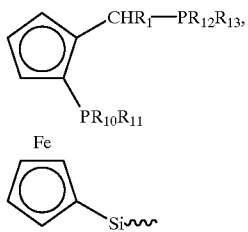

(VIa)

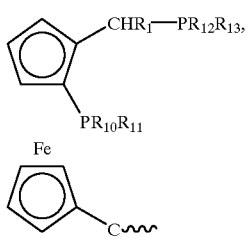

(VIb)

where $R_1$, $R_{10}$, $R_{11}$, $R_{12}$, $R_{13}$, B, FU,

Si∼∼ and C∼∼ have the meanings and preferences given in the description of the ferrocenyl ligands, additionally the ferrocenyl ligand of formula (VI) may be bound via the functional group FU to an inorganic or polymeric organic support material.

These ruthenium catalysts can be prepared by methods analogous to those known from the literature. Possible starting compounds for the reaction with the compounds of the formula (Ia) or (Ib) to give the catalyst complexes are, for example: $[Ru_2(CF_3CO_2)_4 (H_2O) (COD)_2]$, $[Ru_2Cl_4(p\text{-}cymene)_2]$ or $[RuCl_2COD]_n$. Further information may also be found in N. C. Zanetti et al., Organometallics 15, pages 860–866 (1996).

The following examples illustrate the invention.

General Procedures

All operations are carried out under an inert gas atmosphere (argon or nitrogen). All reactions with n-, sec- or tert-BuLi are carried out in dried and degased solvents.
Abbreviations used:
COD: cyclooctadiene
TMEDA: N,N,N,N-tetramethylethylenediamine
n-BuLi: n-butyl lithium is used as a 1.6 m hexane solution
cy: cyclohexane; Et: ethyl; Me: methyl; Ph: phenyl; xyl: 3,5-xylyl.
Synthesis of the precursors (further details are given in WO96/32400)
A1: (R)-N,N-dimethyl-1-[(S)-1',2-bis(bromo)ferrocenyl]ethylamine
A2: (R)-N,N-dimethyl-1-[1'-(bromo)-(S)-2-(diphenylphosphino)ferrocenyl]ethylamine A3: (R)-N,N-dimethyl-1-[(S)-1',2-bis(chloro)ferrocenyl]
    ethylamine
A4: (R)-N,N-dimethyl-1-[(S)-1',2-bis(iodo)ferrocenyl]
    ethylamine
A5: (R)-1-[1'-(bromo)-(S)-2-diphenylphosphinoferrocenyl]
    ethyldicyclohexylphosphine (105)
A6: (R)-1-[1'-(bromo)-(S)-2-diphenylphosphinoferrocenyl]
    ethyldiphenylphosphine (106)
A7: (R)-1-[1'-(bromo)-(S)-2-diphenylphosphinoferrocenyl]
    ethyldixylylphosphine (107)

EXAMPLES B

Preparation Of The Functionalized Compounds

Example B1

Preparation of (R)-1-[1'-(3-hydroxypropyl)-(S)-2-diphenylphosphinoferrocenyl]ethyldixylylphosphine

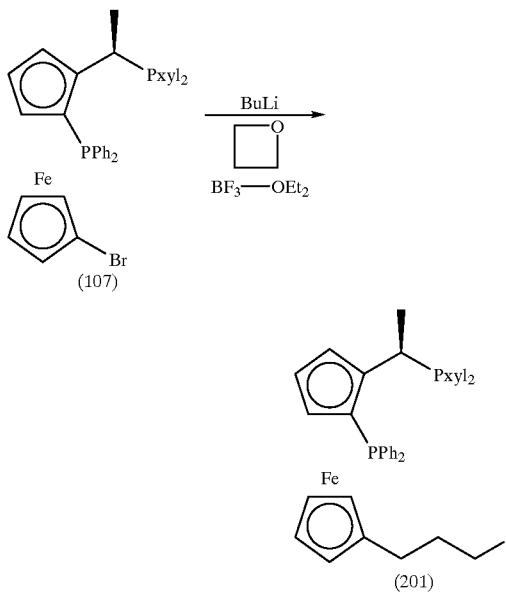

17 ml of a 1.6 molar BuLi/hexane solution are added dropwise at about −40° C. while stirring to a solution of 970 mg (1.35 mmol) of the compound (107) from Example A7 in 15 ml of diethyl ether. After stirring for 30 minutes at this temperature, 20 ml of THF, 0.34 ml (2.7 mmol) of $BF_3$ etherate and 0.35 ml (5.4 mmol) of trimethylene oxide are added one after the other at −70° C. and the mixture is stirred further for 40 minutes at about −70° C. At this temperature, the mixture is then treated with 4 ml of saturated aqueous $NaHCO_3$ solution, stirred further for one hour without cooling and finally extracted with ethyl acetate and water. The organic phases are collected, washed with water, dried over $Na_2SO_4$ and evaporated on a rotary evaporator. The orange crude product is purified by chromatography (silica gel: Merck 60; eluant: hexane/ethyl acetate 4/1). This gives 490 mg of product (yield: 52%, orange powder).

Analytical data: $^1$H-NMR ($CDCl_3$); δ 1.35–1.6 (m, 3H, C—$CH_3$ and 2H, $CH_2$—$CH_2$—$CH_2$), 1.75–2.2 (m, 2H, cyclopentadiene-$CH_2$—), 2.20 and 2.26 (each 1 s, 12H, Ph—$CH_3$), 3.45–4.2 (m, 7H, $C_5H_3FeC_5H_4$), 3.50 (t, 2H, $CH_2$—OH), 3.72 (m, 1H, CH—$CH_3$), 6.75–7.7 (m, 16H, P($C_6H_5$)$_2$ and P($C_6H_3Me_2$)). $^{31}$P-NMR (CDCl3): δ 6.75 (d, Pxylyl$_2$), −25.4 (d, PPh$_2$), JPP 20 Hz.

Example B2

Preparation of (R)-1-[1'-(1''-triethoxysilano-3''-carbamatopropylpropyl)-(S)-2-diphenylphosphinoferrocenyl]ethyldixylylphosphine

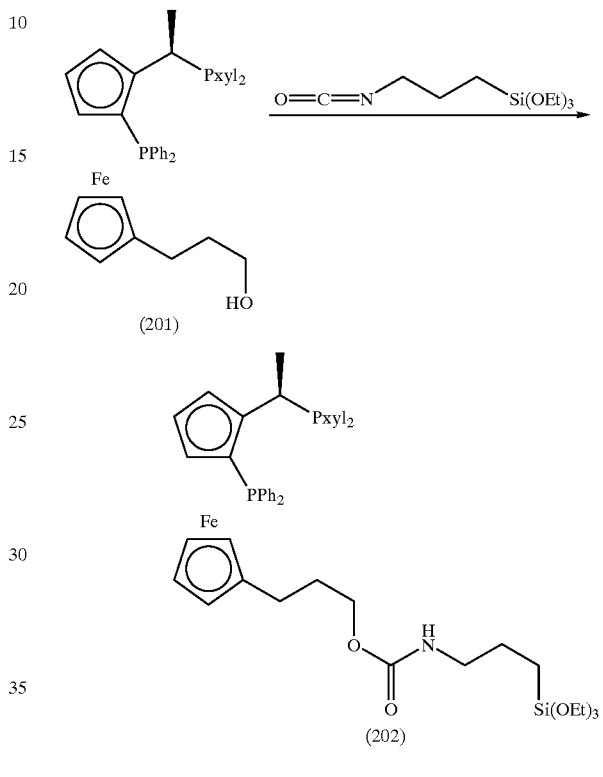

A solution of 460 mg (0.66 mmol) of the compound (201) from Example B1, 0.35 ml (1.3 mmol) of 3-isocyanatopropyltriethyoxysilane and 10 mg of dibutyltindilaurate (catalyst) in 8 ml of methylene chloride is stirred for 24 hours at room temperature. The product which is obtained by evaporation of the solvent can, if required, be immobilized without purification.

Purification is carried out by flash chromatography (silica gel: Merck 60; eluant: hexane/ethyl acetate 1/1). This gives 410 mg of product (yield: 75%, orange, virtually solid oil).

Analytical data: $^1$H-NMR ($CDCl_3$): δ 0.62 (t, 2H, $CH_2$—Si), 1,22 (t, 3×3H, $CH_3$—$CH_2$—O), 1.43 (t, 3H, C—$CH_3$), 1.5–1.7 (m, 4H, $CH_2$—$CH_2$—Si and $CH_2$—$CH_2$—O), 1.85–2,1 (m, 2H, cyclopentadiene $CH_2$—), 2.20 and 2.26 (each 1 s, 12H, Ph—$CH_3$), 3.17 (m, 2H, $CH_2$—N), 3.4–4.2 (m, 7H, $C_5H_3FeC_5H_4$, 1H, CH—$CH_3$, 2H, $CH_2$—O), 3.78 (q, 2×2H, $CH_2$—O—Si), 4.83 (unsharp t, 1H, NH) 6.75–7.7 (m, 16H, P($C_6H_5$)$_2$ and P($C_6H_3Me_2$)). $^{31}$P-NMR (CDCl3): δ 7.0 (d, Pxylyl$_2$), −25.4 (d, PPh$_2$), JPP 20 Hz.

Example B3

Preparation of (R)-1-[1'-(phthalimidopropyl)-(S)-2-diphenylphosphinoferrocenyl]ethyldixylylphosphine

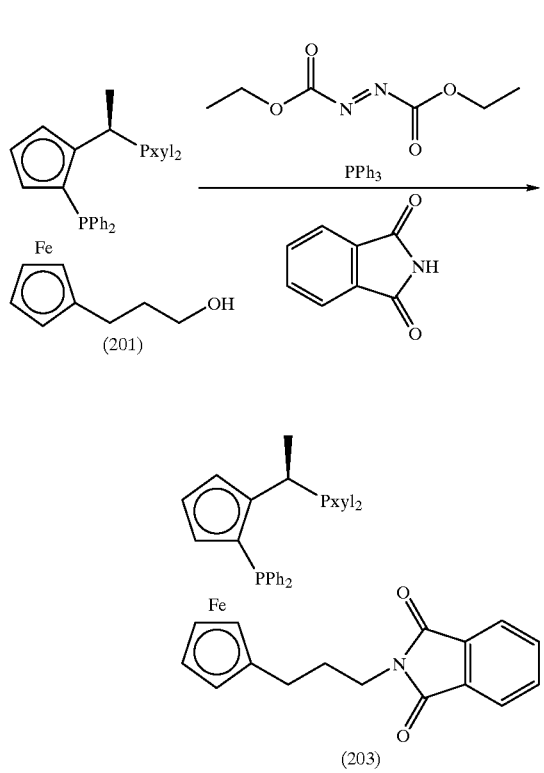

0.18 ml (1.05 mmol) of diethyl azodicarboxylate are added at room temperature to a mixture of 488 mg (0.7 mmol) of the compound (201) from Example B1, 370 mg (1.4 mmol) of triphenylphosphine and 135 mg (0.91 mmol) of phtalimide in 15 ml of THF and the reaction mixture is stirred overnight. It is then evaporated on a rotary evaporator and purified by chromatography (silica gel: Merck 60; eluant: hexane/ethyl acetate 4/1). This gives 350 mg of product (yield: 60%, reddish brown, virtually solid oil).

Analytical data: $^1$H-NMR (CDCl$_3$): δ 1.41 (m, 3H, C—CH$_3$) 1.63 (m, 2H, CH$_2$—CH$_2$—CH$_2$), 1.8–2,1 (m, 2H, cyclopentadiene-CH$_2$—), 2.20 and 2.26 (each 1 s, 12H, Ph—CH$_3$), 3.45–4.2 (m, 7H, C$_5$H$_3$FeC$_5$H$_4$), 3.45 (t, 2H, CH$_2$—N), 3.72 (m, 1H, CH—CH$_3$), 6.75–7.7 (m, 16H, P(C$_6$H$_5$)$_2$ and P(C$_6$H$_3$Me$_2$)), 7.7 and 8.1 (2m, each 2H, phthalimide) $^{31}$P-NMR (CDCl3): δ 7.1 d, Pxylyl$_2$), −25.3 (d, PPh$_2$), JPP 20 Hz.

Example B4

Preparation of (R)-1-[1'-(aminopropyl)-(S)-2-diphenylphosphinoferrocenyl]ethyldixylylphosphine

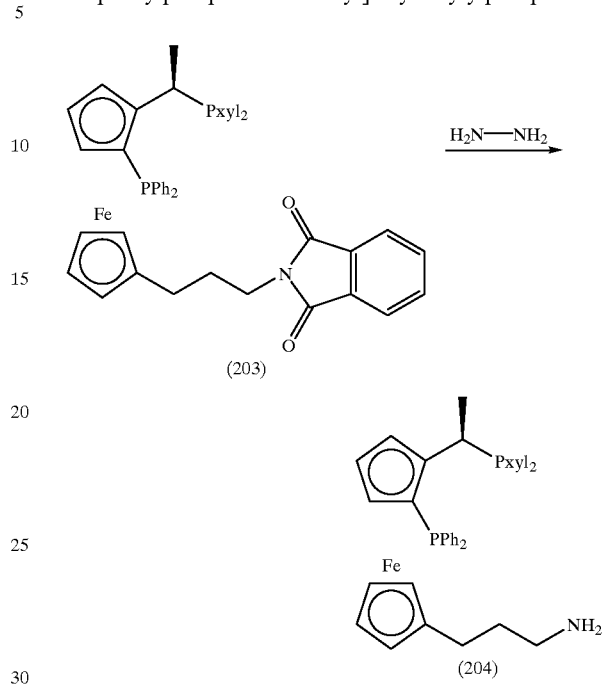

A mixture of 350 mg (0.42 mmol) of the compound (203) from Example B3 in 7 ml of ethanol is treated with 0.1 ml of hydrazine hydrate and subsequently refluxed for 2 hours. After cooling, 6 ml of diethyl ether are added to the orange suspension, the suspension is filtered and the residue is washed with diethyl ether. The resulting orange solution is concentrated on a rotary evaporator, during which procedure some further phthalic hydrazide precipitates, and this is again filtered off. The product is then evaporated to dryness on a rotary evaporator, subsequently redissolved in diethyl ether, the solution is filtered once more and again evaporated on a rotary evaporator. This gives 230 mg of product (yield: 78%, orange, solid foam).

Analytical data: $^1$H-NMR (CDCl$_3$): δ 1.2–2.0 (plurality of m, 3H, C—CH$_3$ and 4H, cyclopentadiene-CH$_2$—CH$_2$—CH$_2$), 2.20 and 2.26 (each 1 s, 12H, Ph—CH$_3$), 2.55 (t, 2H, CH$_2$—N), 3.45–4.2 (m, 7H, C$_5$H$_3$FeC$_5$H$_4$), 3.72 (m, 1H, CH—CH$_3$), 6.75–7.7 (m, 16H, P(C$_6$H$_5$)$_2$ and P(C$_6$H$_3$Me$_2$)). $^{31}$P-NMR (CDCl3): δ 6.8 (d, Pxylyl$_2$), −25.4 (d, PPh$_2$), JPP 20 Hz.

Example B5

Preparation of (R)-1-[1'-(aldehyde)-(S)-2-diphenylphosphinoferrocenyl]ethyldixylylphosphine

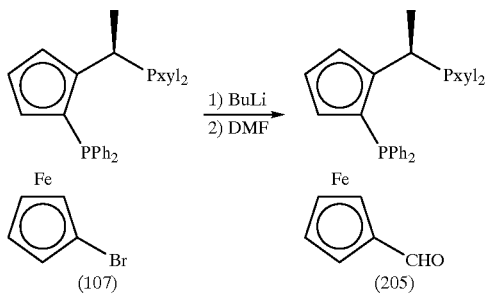

4 ml of a 1.6 molar BuLi/hexane solution are added dropwise at −30° C. while stirring to a solution of 4 g (5.57 mmol) of the compound (107) from Example A7 in 50 ml of diethyl ether. After stirring for 30 minutes at this temperature, the mixture is cooled to −70° C. and quickly treated with 40 ml of DMF, care being taken to ensure that the temperature does not rise above −20° C. After stirring for a few hours without cooling, the orange-brown solution is treated with 50 ml of water and extracted a number of times with toluene. The organic phases are collected, washed with water, dried over $Na_2SO_4$ and evaporated on a rotary evaporator. The orange crude product is purified by chromatography (silica gel: Merck 60; eluant: hexane/ethyl acetate 5/1). This gives 2.12 g of product (yield: 57%, orange powder).

Analytical data: $^1$H-NMR (CDCl$_3$): δ 1.48 (t, 3H, C—CH$_3$), 2.21 and 2.28 (each 1 s, 12H, Ph—CH$_3$), 3.69 (m, 1H, CH—CH$_3$), 4.0–4.65 (m, 7H, C$_5$H$_3$FeC$_5$H$_4$), 6.75–7.7 (m, 16H, P(C$_6$H$_5$)$_2$ and P(C$_6$H$_3$Me$_2$)$_2$, 9.4 (s, 1H, CHO). $^{31}$P-NMR (CDCl3): δ 8.1 (d, Pxylyl$_2$), −27.0 (d, PPh$_2$), JPP 23 Hz.

Example B6

Preparation of (R)-1-[1'-(hydroxymethyl)-(S)-2-diphenylphosphinoferrocenyl]ethyldixylylphosphine

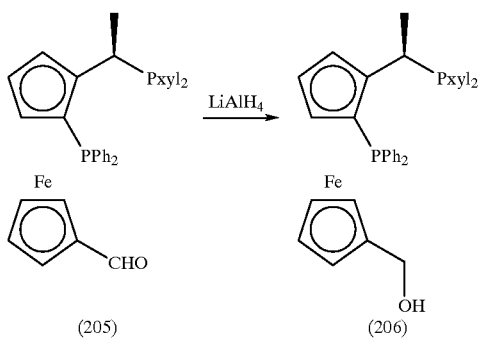

20 mg of lithium aluminium hydride are added to a solution of 617 mg (0.92 mmol) of the compound (205) from Example B5 and the mixture is stirred at room temperature for 3 hours. The excess hydride is then decomposed using a little water and the mixture is subsequently extracted in aqueous NaCl solution and ethyl acetate. The organic phases are collected, washed with water, dried over MgSO$_4$ and evaporated on a rotary evaporator. The orange crude product is purified by chromatography (silica gel: Merck 60; eluant: hexane/ethyl acetate 3/1). This gives 0.6 g of product (yield: 97%, orange powder).

Analytical data: $^1$H-NMR (CDCl$_3$): δ 1.44 (t, 3H, C—CH$_3$), 2.20 and 2.26 (each 1 s, 12H, Ph—CH$_3$), 3.6–4.25 (m, 7H, C$_5$H$_3$FeC$_5$H$_4$, 1H, CH—CH$_3$, 2H, CH$_2$—OH), 6.75–7.7 (m, 16H, P(C$_6$H$_5$)$_2$ and P(C$_6$H$_3$Me$_2$)). $^{31}$P-NMR (CDCl3); δ 6.5 (d, Pxylyl$_2$), −25.4 (d, PPh$_2$), JPP 20 Hz.

Example B7

Preparation of (R)-1-[1'-(N-butyliminomethyl)-(S)-2-diphenylphosphinoferrocenyl]ethyldixylylphosphine

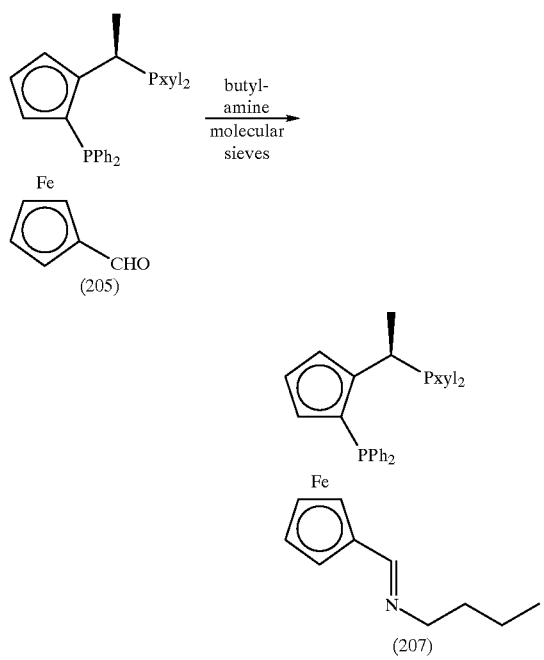

A solution of 500 mg (0.75 mmol) of the compound (205) from Example B5 and 0.75 ml of butylamine (7.5 mmol) in 10 ml of diethyl ether is stirred for 24 hours at room temperature in the presence of 2 g of molecular sieves (4 Å).

The imine of the formula (207) is, without purification, isolated virtually quantitatively, by filtering off the molecular sieves washing twice with 5 ml of diethyl ether, and evaporating the ether solution. According to proton NMR, the desired product is obtained in quantitative yield.

Analytical data: $^1$H-NMR (CDCl$_3$): δ 0.91 (t, 3H, CH$_3$ of butyl), 1.2–1.6 (m, 7H, C—CH$_3$, CH$_2$—CH$_2$), 2.20 and 2.26 (each 1 s, 12H, Ph—CH$_3$), 3.3 (q, 2H, CH$_2$—N), 3.73 (m, 1H, cyclopentadiene-CH—CH$_3$), 3.7–4.6 (m, 7H, C$_5$H$_3$FeC$_5$H$_4$), 6.75–7.7 (m, 16H, P(C$_6$H$_5$)$_2$ and P(C$_6$H$_3$Me$_2$)$_2$) 7.53 (s, 1H, CH=N).

Example B8

Preparation of (R)-1-[1'-(N-butylaminomethyl)-(S)-2-diphenylphosphinoferrocenyl]ethyldixylylphosphine

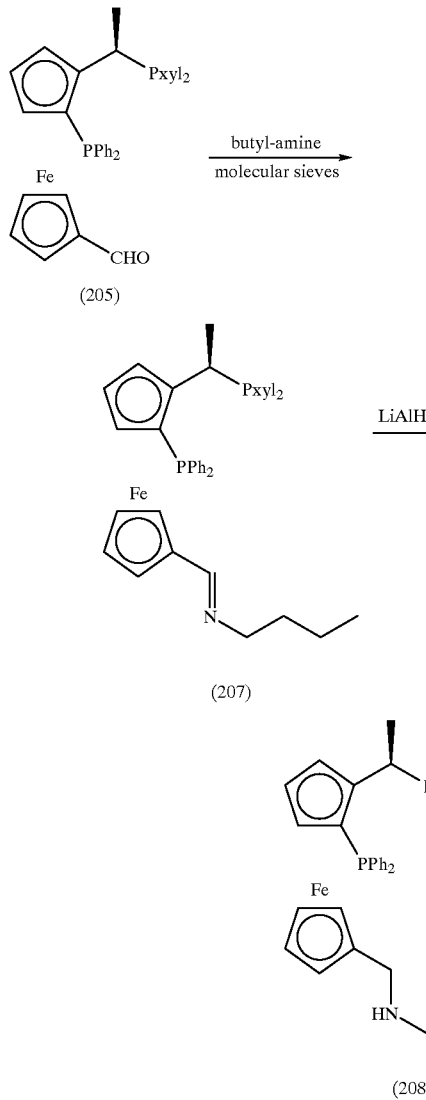

A solution of 500 mg (0.75 mmol) of the compound (205) and 0.75 ml of butylamine (7.5 mmol) in 10 ml of diethyl ether is stirred for 24 hours at room temperature in the presence of 2 g of molecular sieves (4 Å). The imine of the formula (207) can, without purification, be isolated virtually quantitatively by filtering off the molecular sieves, washing twice with 5 ml of diethyl ether and evaporating the ether solution. According to proton NMR, the desired product is obtained in quantitative yield.

Analytical data: $^1$H-NMR (CDCl$_3$): δ 0.91 (t, 3H, CH$_3$ of butyl), 1.2–1.6 (m, 7H, C—CH$_3$, CH$_2$—CH$_2$), 2.20 and 2.26 (each 1 s, 12H, Ph—CH$_3$), 3.3 (q, 2H, CH$_2$—N), 3.73 (m, 1H, cyclopentadiene-CH—CH$_3$), 3.7–4.6 (m, 7H, C$_5$H$_3$FeC$_5$H$_4$), 6.75–7.7 (m, 16H, P(C$_6$H$_5$)$_2$ and P(C$_6$H$_3$Me$_2$)$_2$) 7.53 (s, 1H, CH=N).

Without isolating the imine of the formula (207), the compound of the formula (208) is prepared directly by reduction with LiAlH$_4$. For this purpose, a total of 200 mg of LiAlH$_4$ are added in small portions at room temperature to the ether solution of the imine of the formula (207) obtained as described above and the mixture is stirred overnight. About 0.3 ml of water is then added slowly to the mixture, resulting in the precipitation of aluminium oxide which is filtered off through Hyflo and washed a number of times with diethyl ether. Evaporation of the ether on a rotary evaporator gives an almost solid, orange oil which is virtually pure and can be used further without purification.

$^1$H-NMR (CDCl$_3$): δ 0.87 (t, 3H, CH$_3$ of butyl), 1.2–1.5 (m, 7H, C—CH$_3$, CH$_2$—CH$_2$), 2.20 and 2,26 (each 1 s, 12H, Ph—CH$_3$), 2.43 (t, 2H, CH$_2$—N), 3.02 and 3,2 (2d, each 1H, cyclopentadiene-CH$_2$—N), 3.6–4.2 (m, 7H, C$_5$H$_3$FeC$_5$H$_4$) 3.72 (m, 1H, cyclopentadiene-CH—CH$_3$), 6.75–7.7 (m, 16H, P(C$_6$H$_5$)$_2$ and P(C$_6$H$_3$Me$_2$)$_2$). $^{31}$P-NMR (CDCl3): δ 6.9 (d, Pxylyl$_2$), −25.5 (d, PPh$_2$), JPP 20 Hz.

Example B9

Preparation of (R)-1-[1'-(1"-triethoxysilano-3"-carbamatopropylmethyl-(S)-2-diphenylphosphinoferrocenyl]ethyldixylylphosphine

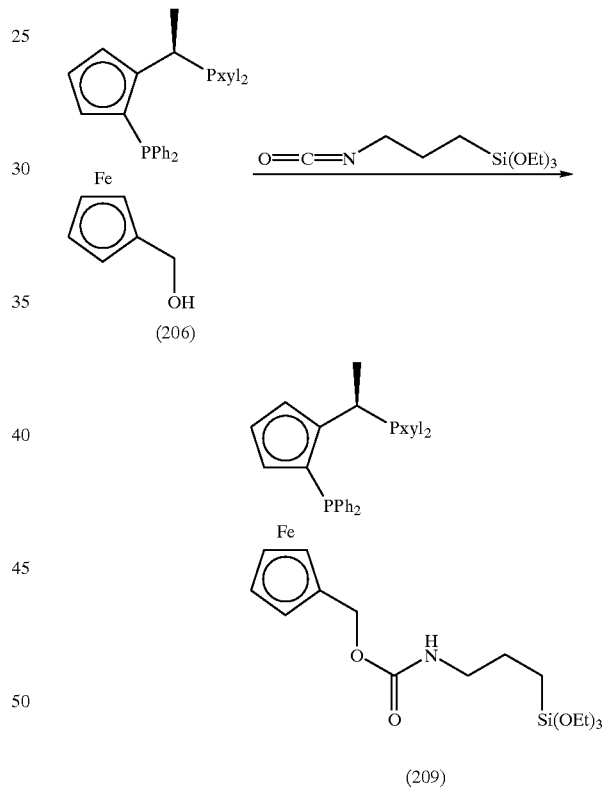

A solution of 570 mg (0.85 mmol) of the compound of the formula (206) from Example B6 in 5 ml of methylene chloride, 0.28 ml (1.1 mmol) of 3-isocyanatopropyltriethoxysilane and 10 mg of dibutyltin dilaurate (catalyst) are stirred for 24 hours at room temperature. The product which is obtained after evaporation of the solid can be immobilized without purification.

Purification is carried out by flash chromatography (silica gel: Merck 60; eluant: hexane/ethyl acetate 1/1). This gives 640 mg of product (yield: 82%, orange, virtually solid oil).

Analytical data: $^1$H-NMR (CDCl$_3$): δ 0.58 (t, 2H, CH$_2$—Si), 1.2 (t, 3×3H, CH$_3$—CH$_2$—O), 1.43 (t, 3H, C—CH$_3$), 1.56 (m, 2H, CH$_2$—CH2—Si), 2.20 and 2.26 (each 1 s, 12H, Ph—CH$_3$), 3.11 (m, 2H, CH$_2$—N), 3.6–4.8 (m, 7H, C$_5$H$_3$FeC$_5$H$_4$, 1H, CH—CH$_3$, 2H, CH$_2$—O, 1H, NH), 3.78 (q, 2×2H, CH$_2$—O—Si), 6.75–7.7 (m, 16H, P(C$_6$H$_5$)$_2$ and P(C$_6$H$_3$Me$_2$)). $^{31}$P-NMR (CDCl3): δ 7,1 (d, Pxylyl$_2$), −25.9 (d, PPh$_2$), JPP 20 Hz.

Example B10

Preparation of (R)-1-[1'-(hydroxymethyl)-(S)-2-diphenylphosphinoferrocenyl]ethyldixylylphosphine (modified preparation compared with Example B6)

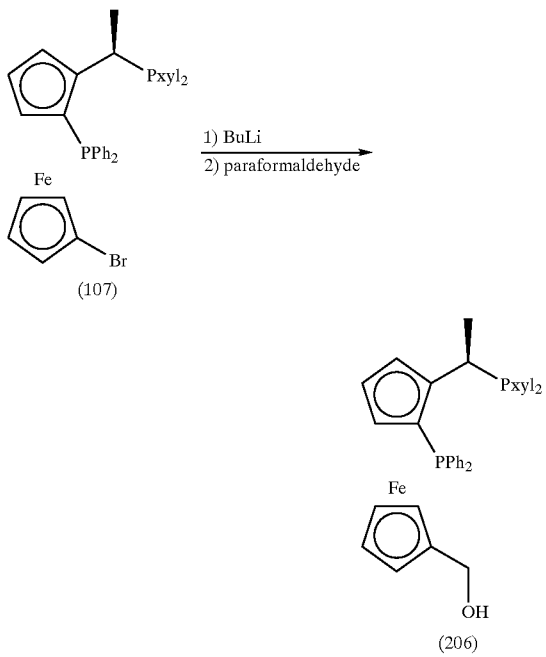

0.18 ml of a 1.6 molar BuLi/hexane solution is added dropwise at about −30° C. while stirring to a solution of 160 mg (0.228 mmol) of the compound of the formula (107) from Example A7 in 3 ml of diethyl ether. After stirring for 30 minutes at this temperature, the mixture is cooled to −70° C. and 13 mg of paraformaldehyde are added, but this hardly dissolves. The mixture is stirred overnight at room temperature. It is then extracted with water/ethyl acetate, the organic phases are collected, washed with water, dried over Na$_2$SO$_4$ and evaporated on a rotary evaporator. The orange crude product is purified by chromatography (silica gel: Merck 60: eluant: hexane/ethyl acetate 2/1). This gives 70 mg of product (yield: 45%, orange powder).

Analytical data: $^1$H-NMR (CDCl$_3$): δ 1.44 (t, 3H, C—CH$_3$), 2.20 and 2.26 (each 1 s, 12H, Ph—CH$_3$), 3.6–4.25 (m, 7H, C$_5$H$_3$FeC$_5$H$_4$, 1H, CH—CH$_3$, 2H, CH$_2$—OH), 6.75–7.7 (m, 16H, P(C$_6$H$_5$)$_2$ and P(C$_6$H$_3$Me$_2$)). $^{31}$P-NMR (CDCl3): δ 6.3 (d, Pxylyl$_2$), −25.5 (d, PPh$_2$), JPP 20 Hz.

Example B11

Preparation of (R)-1-[1'-(1"-triethoxysilano-3'''-carbamidopropylmethyl)-(S)-2-diphenylphosphinoferrocenyl]ethyldixylylphosphine

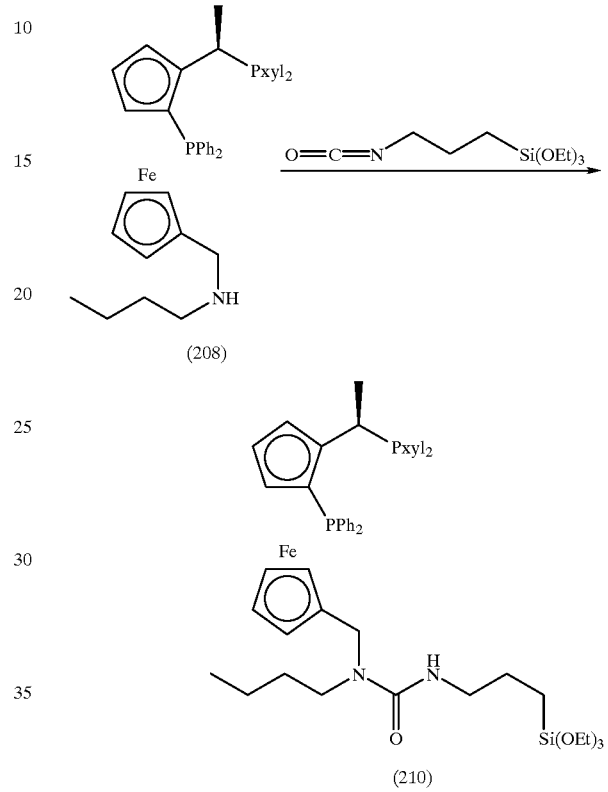

A solution of 490 mg (0.68 mmol) of the compound of the formula (208) in 5 ml of methylene chloride and 0.23 ml (0.9 mmol) of 3-isocyanatopropyltriethoxysilane is stirred for 24 hours at room temperature. The product which is obtained after evaporation of the solvent can, if required, by immobilized without purification.

Purification is carried out by flash chromatography (silica gel: Merck 60; eluant: hexane/ethyl acetate 1/1). This gives 545 mg of product (yield: 83%, orange, virtually solid oil).

Analytical data: $^1$H-NMR (CDCl$_3$): δ 0.58 (t, 2H, CH$_2$—Si), 0.99 (t, 3H, CH$_3$—CH$_2$—), 1.2 (t, 3×3H, CH$_3$—CH$_2$—O), 1.2–1.4 (m, 4H, 2 CH$_2$ of N-butyl), 1.43 (t, 3H, C—CH$_3$), 1.54 (m, 2H, CH$_2$—CH2—Si), 2.20 and 2.26 (each 1 s, 12H, Ph—CH$_3$), 2.85–3.2 (m, 4H, 2×CH$_2$—CH$_2$—N), 3.45–4.35 (m, 7H, C$_5$H$_3$FeC$_5$H$_4$, 1H, CH—CH$_3$, 2H, cyclopentadiene-CH$_2$—N, 1H, NH), 3.78 (q, 2×2H, CH$_2$—O—Si), 6.75–7.7 (m, 16H, P(C$_6$H$_5$)$_2$ and P(C$_6$H$_3$Me$_2$)). $^{13}$P-NMR (CDCl3): δ 7.1 (d, Pxylyl$_2$), −25.9 (d, PPh$_2$), JPP 20 Hz.

Example B12

Synthesis of (R)-N,N-dimethyl-1-[1'-(1"-dimethylsilyl-3"-chloropropyl)-(S)-2-diphenylphosphinoferrocenyl]ethylamine

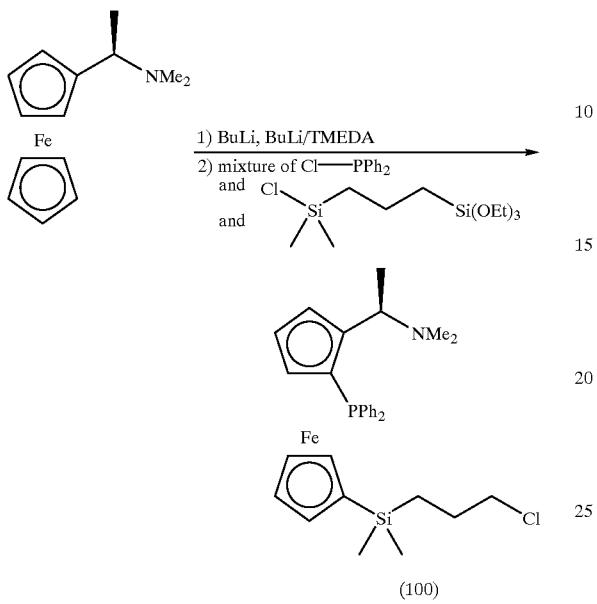

(100)

32.5 ml of a 1.6 molar butyllithium/hexane solution (52 mmol) are added dropwise at room temperature while stirring to a solution of 10.29 g (40 mmol) of (R)-N,N-dimethyl-1-ferrocenylethylamine 1 in 50 ml of diethyl ether. After stirring for one hour, a further solution consisting of 35.6 ml of a 1.6 molar butyllithium/hexane solution (57 mmol) and 7.5 ml of TMEDA (50 mmol) is added dropwise and the reddish brown reaction solution is stirred further for 5 hours. Subsequently, at about −20° C., a solution consisting of a mixture of 7.4 ml of chlorodiphenylphosphine (40 mmol) and 22.9 ml of 3-chloropropyldimethylchlorosilane (140 mmol) is added dropwise. The reaction mixture is subsequently stirred overnight at room temperature.

Work-up: The reaction mixture is, at 0° C., slowly treated with 10 ml of saturated NaHCO$_3$ solution and subsequently 100 ml of water and extracted 3 times with 50 ml each time of ethyl acetate. The organic phase is extracted with 50 ml of water, dried over Na$_2$SO$_4$ and evaporated under reduced pressure (10–20 torr) on a rotary evaporator. The excess, hydrolysed chlorosilane is then distilled off from the crude product under a high vacuum (about 0.01 torr, bath temperature up to 70° C.). Rough column chromatography (eluant=hexane/acetic acid) gives 15.4 g of a mixture of (R)-(S)-2and some BPPFA. The BPPFA can be removed by recrystallization from methanol/ethanol 1:1. This gives 13.5 g of product having a purity of 95% (yield: 55%, reddish brown viscous oil). Pure product can be obtained if required by a 2nd chromatography.

Characterization: 31P-NMR (CDCl$_3$: d −23.7160 $^1$H-NMR (CDCl$_3$): d 0.05 (s, 3H, Si—CH$_3$), 0.15 (s, 3H, CH$_3$), 0.6 (m, 2H, CH$_2$—Si), 1.28 (d, $_{3H}$, J 7Hz, CH—CH$_3$), 1.5–1.9 (m, 2H, CH$_2$—CH$_2$—Cl), 1.78 (s, 6H, N(CH$_3$)$_2$), 3.4 (t, 2H, J 7Hz, CH$_2$—Cl), 3.5–4.4 (m, 8H, C$_5$H$_4$FeC$_5$CH), 7.1–7.7 (m, 10H, P(C$_6$H$_5$)$_2$.

The corresponding compound having the (S)-(R) configuration can be prepared in the same way starting from (S)-N,N-dimethyl-1-ferrocenylethylamine.

The following synthesis is carried out starting from the compound (100) having the (R)-(S) configuration and gives the corresponding (R)-(S) ligand. Starting from (100) having the (S)-(R) configuration, the (S)-(R) ligand is obtained in the same way.

Example B13

Synthesis of (R)-1-[1'-(1"-dimethylsilyl-3"-chloropropyl)-(S)-2-diphenylphosphinoferrocenyl]ethyldi-3,5-xyl-1-ylphosphine

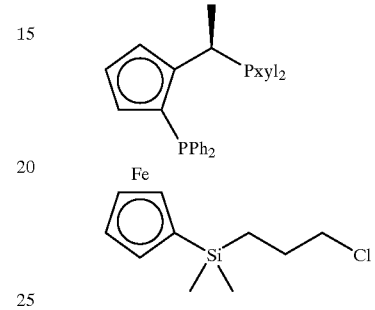

(101)

1.12 g (4.6 mmol) of bis(3,5-xylyl)phosphine in 5 ml of acetic acid are added to 2.66 g (4.6 mmol) of (100) in 10 ml of acetic acid and the mixture is stirred for 90 minutes at 95° C. on an oil bath. After cooling, the reddish brown solution is shaken with 30 ml of toluene and 100 ml of a 5% aqueous NaCl solution. The aqueous phase is then extracted 3 times with 15 ml of toluene. The organic phases are then collected, washed with 50 ml of water, dried over Na$_2$SO$_4$ and evaporated under reduced pressure on a rotary evaporator. The crude product is purified by column chromatography (eluant: hexane/diethyl ether). This gives 1.85 g of product (orange powder, yield: 52%).

Characterization: 31P-NMR (CDCl$_3$): d −25.46 (d, PPh$_2$), 6.65 (d, Pxyl$_2$), JPP 21Hz. 1H-NMR (CDCl$_3$): d 0.04 (s, 3H, Si—CH$_3$), 0.14 (s, 3H, Si—CH$_3$), 0.61 (m, 2H, CH$_2$—Si), 1.43 (d, 3H, CH—CH$_3$), 1.5–1.7 (m, 2H, CH$_2$—CH$_2$—Cl), 2.20 and 2.30 (two s, 6H, C$_6$H$_3$(CH$_3$)$_2$), 3.4 (t, 2H, J=7, CH$_2$—Cl), 3.2–4.4 (m, 8H, C$_5$H$_4$FeC$_5$H$_3$CH), 6.75–7.8 (m,16H, P(C$_6$H$_5$)$_2$), P(C$_6$H$_3$(Me)$_2$).

Example B14

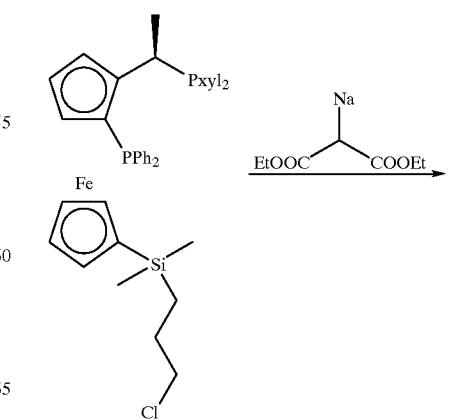

(102)

-continued

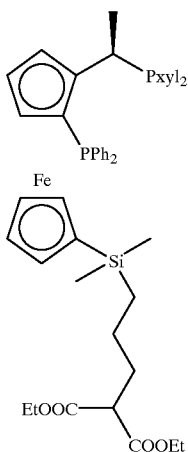

1 g (1.3 mmol) of (101) is stirred in a previously prepared solution of 38 mmol of sodium ethoxide and 76 mmol of diethyl malonate in 23 ml of ethanol for 20 hours at 80–90° C. in the presence of 100 mg of potassium iodide. The mixture is subsequently cooled, evaporated on a rotary evaporator, treated with 10 ml of 2N HCl and extracted with water/ethyl acetate. The organic phase is washed with water and saturated NaCl solution, dried over sodium sulfate and the crude product is purified by chromatography (silica gel: Merck 60; eluant: hexane/ethyl acetate 10/1). This gives 1.08 g of product (yield: 92%, orange, almost solid oil).

Analytical data: 1H-NMR (CDCl3): d 0.0 (s, 3H, Si—CH3), 0.08 (s, 3H, Si—CH3), 0.5 (m, 2H, CH2—Si), 1.2 (t, 6H, OCH2CH3) 1.48 (t, 3H, C—CH3), 1.82 (m, 2H, CH2-CH(COOEt)2) 2.15 and 2.25 (each 1 s, 12H, Ph—CH3), 3.2–4.4 (m, 9H, C5H3FeC5H4, CH—CH3, CH(COOEt)2), 4.15 (q, 4H, OCH2CH3) 6.7–7.7 (m, 16H, P(C6H5)2 and P(C6H3Me2)). 31P-NMR (CDCl3): d 6.8 (d, Pxyl2), –25.2 (d, PPh2), JPP 21 Hz. Microanalysis, calculated for C52 H62 Fe O4P2 Si: C, 69.63; H, 6.97; P, 6.91; Si, 3.13. Found: C, 69.65; H, 7.07; P, 6.87; Si, 3.23.

Example B15

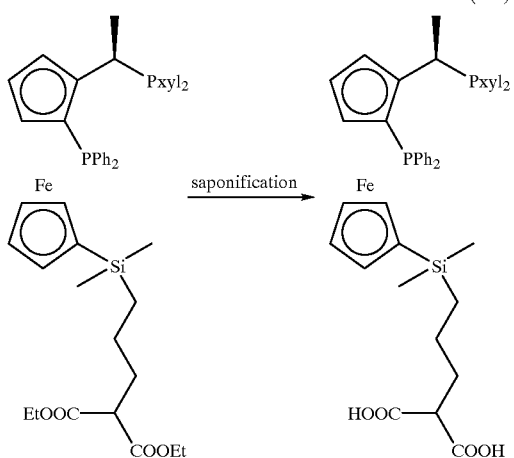

A solution of 1 g of KOH in 1.5 ml of water is added to a solution of 700 mg (0.78 mmol) of (102) in 25 ml of ethanol and the mixture is stirred for 1 hour at room temperature. It is subsequently evaporated on a rotary evaporator and the orange, solid residue is extracted in toluene, ethyl acetate/water, with the product remaining in the aqueous phase. The aqueous phase is washed once more with ethyl acetate, toluene is then added and the pH is adjusted to 2–3 using 2N HCl, with the orange product going over into the organic phase. The toluene phase is washed with water, dried over sodium sulfate, evaporated on a rotary evaporator and dried in a high vacuum. This gives 605 mg of product (orange, solid).

Analytical data: 1H-NMR (CDCl3): d 0.0 (s, 3H, Si—CH3), 0.08 (s, 3H, Si—CH3), 0.57 (m, 2H, CH2—Si), 1.55 (m, 3H, C—CH3), 1.95 (m, 2H, CH2—CH(COOH)2) 2.15 and 2.3 (each 1 s, 12H, Ph—CH3), 3.2–4.4 (m, 9H, C5H3FeC5H4, CH—CH3, CH(COOH)2), 6.7–7.7 (m, 16H, P(C6H5)2 and P(C6H3Me2)). 31P-NMR (CDCl3): d 8.4 (d, Pxyl2), –25.9 (d, PPh2), JPP 17 Hz. Microanalysis, calculated for C48 H54 Fe O4 P2 Si: C, 68.57; H, 6.47; P, 7.37. Found: C, 68.54; H, 6.68; P, 7.28.

Example B16

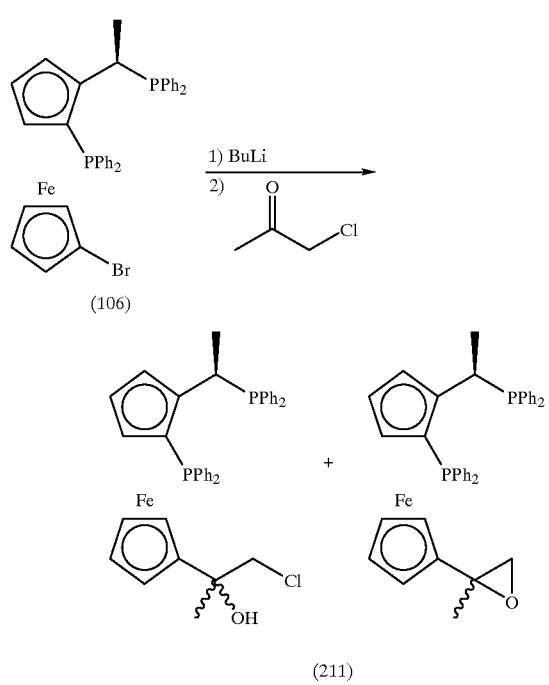

0.16 ml of a 1.6 molar BuLi/hexane solution is added dropwise at about –40° C. while stirring to a solution of 143 mg (0.216 mmol) of 106 in 2 ml of diethyl ether. After stirring for 30 minutes at this temperature, 0.026 ml (0.32 mmol) of chloroacetone is added at –70° C. and the mixture is stirred further at room temperature. It is subsequently extracted in water/ethyl acetate, the organic phase is collected, dried over sodium sulfate and evaporated on a rotary evaporator. This gives 167 mg of orange-brown crude product which, according to NMR, is mainly in the form of chloro-alcohol and epoxide.

Example B17

Preparation of (R)-1-[1'-carboxy-(S)-2-diphenylphosphinoferrocenyl]ethyldixylylphosphine

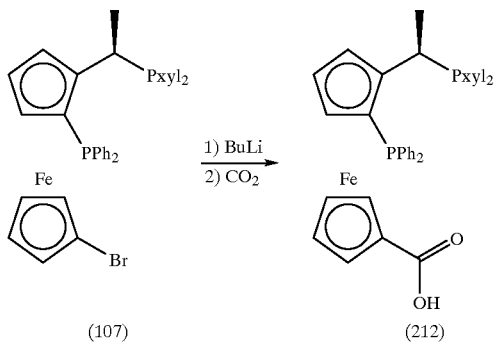

(107)                                    (212)

0.11 ml of a 1.6 molar BuLi/hexane solution is added dropwise at about −30° C. while stirring to a solution of 107 mg (0.149 mmol) of 107 in 3 ml of diethyl ether. After stirring for 30 minutes at this temperature, the mixture is cooled to −70° C. and 500 mg of dry ice are added. The mixture is subsequently stirred at room temperature, with carbon dioxide being evolved. After 4 hours, the mixture is extracted with water (0.1 M HCl)/ethyl acetate, the organic phases are collected, washed with water, dried over $Na_2SO_4$ and evaporated on a rotary evaporator. The orange crude product is purified by chromatography (silica gel: Merck 60; eluant: hexane/ethyl acetate 1/1). This gives 60 mg of product (yield: 57%, orange powder).

Analytical data: $^1$H-NMR (CDCl$_3$): δ 1.44 (t, 3H, C—CH$_3$), 2.20 and 2.26 (each 1 s, 12H, Ph—CH$_3$), 3.7 (m, 1H, CH—CH$_3$), 3.85–4.75 (m, 7H, C$_5$H$_3$FeC$_5$H$_4$), 6.75–7.7 (m, 16H, P(C$_6$H$_5$)$_2$ and P(C$_6$H$_3$Me$_2$)). $^{31}$P-NMR (CDCl$_3$): δ 9.4 (d, Pxylyl$_2$), −25.3 (d, PPh$_2$), JPP 25 Hz.

Example B18

Preparation of (R)-1-[1'-(aldehyde)-(S)-2-diphenylphosphinoferrocenyl]ethyldicyclohexylphosphine

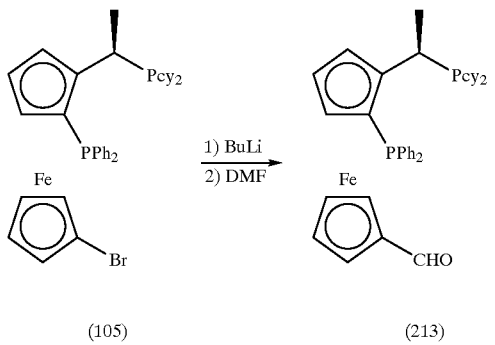

(105)                                    (213)

4.8 ml of a 1.6 molar BuLi/hexane solution are added dropwise at from −60 to −40° C. while stirring to a solution of 4 g (5.95 mmol) of 105 in 40 ml of diethyl ether. After stirring for 30 minutes at this temperature, the mixture is cooled to −70° C. and quickly treated with 9.2 ml of DMF, with care being taken to ensure that the temperature does not rise above −40° C. After stirring for a few hours without cooling, the orange-brown solution is treated with water and extracted a number of times with toluene. The organic phases are collected, washed with water, dried over $Na_2SO_4$ and evaporated on a rotary evaporator. The orange crude product is purified by chromatography (silica gel: Merck 60; eluant: hexane/ethyl acetate 4/1). This gives 3.25 g of product (yield: 88%, orange powder).

Analytical data: $^1$H-NMR (CDCl$_3$): δ 0.9–1.8 (m, 25H, P(C$_6$H$_{11}$)$_2$, C—CH$_3$), 3.18 (m, 1H, CH—CH$_3$), 4–4.65 (m, 7H, C$_5$H$_3$FeC$_5$H$_4$), 7.1–7.7 (m, 10H, P(C$_6$H$_5$)$_2$), 9.42 (s, 1H, CHO). $^{31}$P-NMR (CDCl$_3$): δ −26.3 (d, Pcy$_2$), 17.4 (d, PPh$_2$), JPP 37 Hz.

Example B19

Immobilization on lithiated polystyrene (PS)

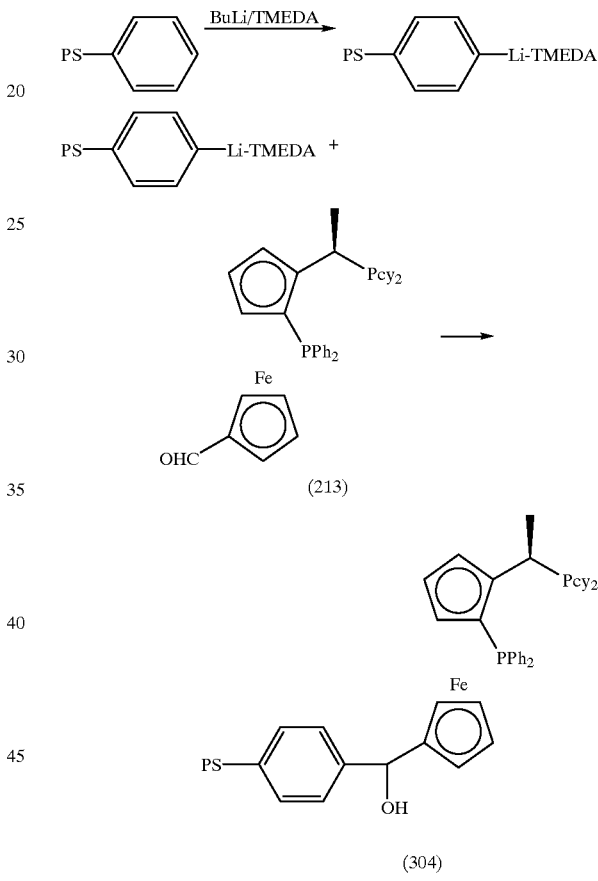

(213)

(304)

1 g of polystyrene, crosslinked with 1% of divinylbenzene, 200–400 mesh (supplier: Fluka, catalogue no. 27'820) is washed by the method of M. J. Farrall et al. (J. Org. Chem., 41 (1976) 3877–82) and lithiated with 2 mmol of BuLi/TMEDA in 8 ml of cyclohexane under reflux for 4.5 hours. The lithiated polymer is washed at room temperature 4 times with 10 ml each time of cyclohexane and then, in 7 ml of cyclohexane, treated with 100 mg of ligand 213, dissolved in 3 ml of cyclohexane, and the orange mixture is stirred for 15 hours. The polymer is then first washed with 10 ml of THF, subsequently hydrolysed with 20 ml of water, then washed a number of times with THF, MeOH and finally with cyclohexane and the yellowish brown product is dried at 70° C. in a high vacuum.

Microanalysis: 0.36% P. This corresponds to 0.058 mmol of ligand/g of product.

Example B20

Preparation of (R)-1-[1'-(N-butylaminomethyl)-(S)-2-diphenylphosphinoferrocenyl] ethyldicyclohexylphosphine

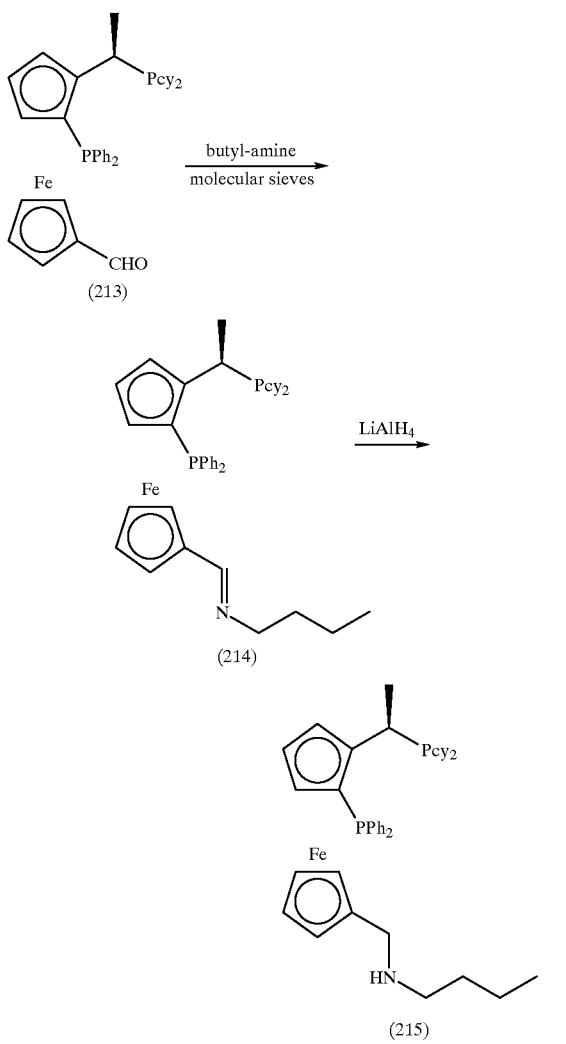

A solution of 1.3 g (2.08 mmol) of 213 and 2.1 ml of butylamine (21 mmol) in 25 ml of diethyl ether is stirred for 24 hours at room temperature in the presence of 4 g of molecular sieves (4 Å). The imine 214 can, without purification, be isolated virtually quantitatively by filtering off the molecular sieves, washing twice with 5 ml of diethyl ether and evaporating the ether solution. According to proton NMR, the desired product is obtained in quantitative yield.

Analytical data (214): $^1$H-NMR (CDCl$_3$): δ 0.93 (t, 3H, CH$_3$ of butyl), 1.0–1.8 (m, 29H, P(C$_6$H$_{11}$)$_2$, C—CH$_3$, CH$_2$—CH$_2$), 3.17 (m, 1H, CH—CH$_3$), 3.3 (m, 2H, CH$_2$—N), 3.8–4.65 (m, 7H, C$_5$H$_3$FeC$_5$H$_5$), 7.1–7.7 (m, 10H, P(C$_6$H$_5$)$_2$), 7.51 (s, 1H, CH=N). $^{31}$P-NMR (CDCl$_3$): δ −25.8 (d, Pcy$_2$), 16.8 (d, PPh$_2$), JPP 35 Hz.

Without isolating the imine 214, 215 is prepared directly by reduction with LiAlH$_4$. For this purpose, a total of 950 mg of LiAlH$_4$ are added at room temperature in small portions to the ether solution of the imine 214 obtained as described above and the mixture is stirred overnight. About 0.8 ml of water is then slowly added to the mixture, resulting in precipitation of aluminium oxide which is filtered off by means of Hyflo and washed a number of times with diethyl ether. Evaporating the ether on a rotary evaporator gives an almost solid, orange oil which is virtually pure and can be used further without purification. If required, the product can be purified by chromatography (silica gel: Merck 60; eluant: ethanol). Yield after purification: 62% (reddish brown, almost solid oil)

$^1$H-NMR (CDCl$_3$): δ 0.90 (t, 3H, CH$_3$ of butyl), 1.0–1.8 (m, 29H, P(C$_6$H$_{11}$)$_2$, C—CH$_3$, CH$_2$—CH$_2$), 2.45 (t, 2H, CH$_2$—N), 2.95–3.22 (d of d, 2H, cp—CH$_2$—N), 3.2 (m, 1H, CH—CH$_3$), 3.6–4.3 (m, 7H, C$_5$H$_3$FeC$_5$H$_4$), 7.1–7.7 (m, 10H, P(C$_6$H$_5$)$_2$) $^{31}$P-NMR (CDCl$_3$): δ −25.0 (d, Pcy$_2$), 16.8 (d, PPh$_2$), JPP 32 Hz.

Example B21

Bonding to Polyethylene

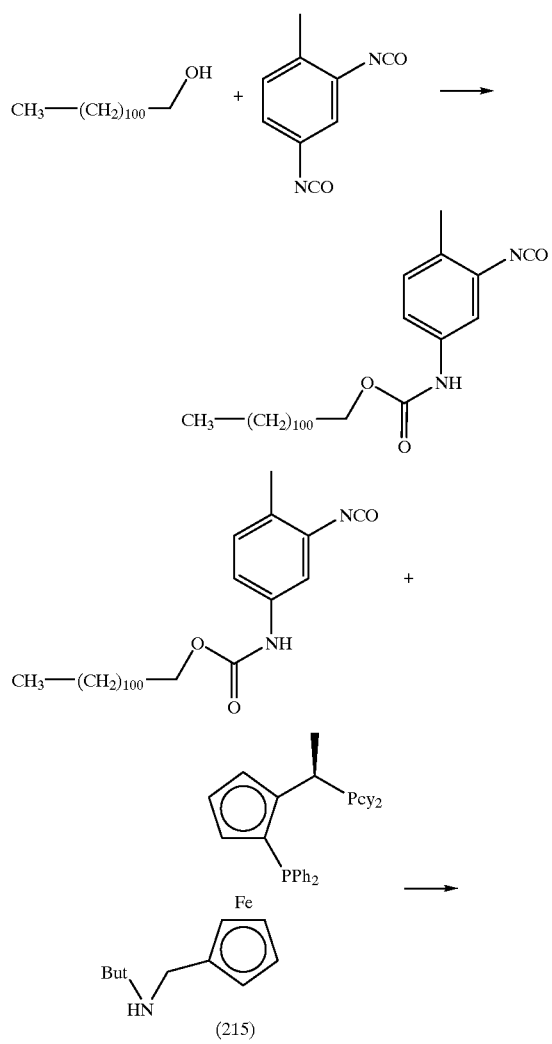

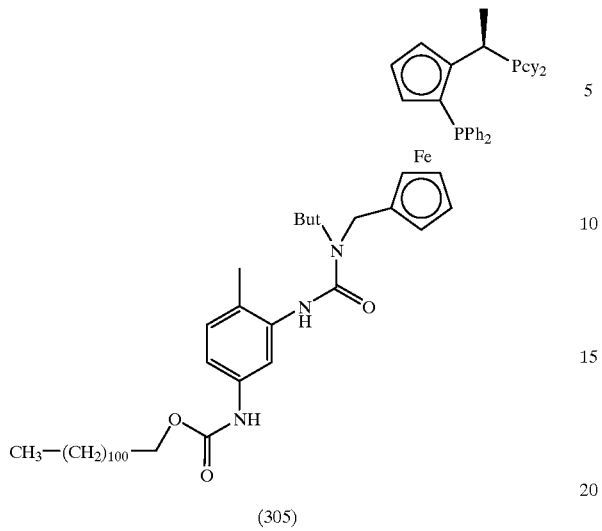

(305)

OH-terminated polybutadiene (MG 1350, Polysciences Inc., Cat. No. 04357) is hydrogenated in hexane over Pd/C under 1 atmosphere of hydrogen to give OH-terminated polyethylene. 0.16 ml (1.09 mmol) of tolylene 1,4-diisocyanate (TDI) and 5 mg of 1,4-diazabicyclo[2.2.2]octane (DABCO) are added to a solution of 1 g (1.2 mmol of OH) of the above product in 15 ml of methylene chloride and the resulting solution is refluxed for 2 hours. 400mg (0.59 mmol) of ligand 215 are then added. After a further 2 hours, 4 ml of ethanol are added and the mixture is stirred further for 12 hours under reflux. The orange solution is finally evaporated and dried in a high vacuum. If required, the product can be purified by extraction in 1N HCl/hexane. The lipophilic product remains in the hexane phase which can be dried over magnesium sulfate and evaporated on a rotary evaporator.

$^{31}$P-NMR (CDCl$_3$): δ −25.2 (d, Pcy$_2$), 16.9 (d, PPh$_2$), JPP 33 Hz.

Example B22

Bonding To Polyethylene Glycol

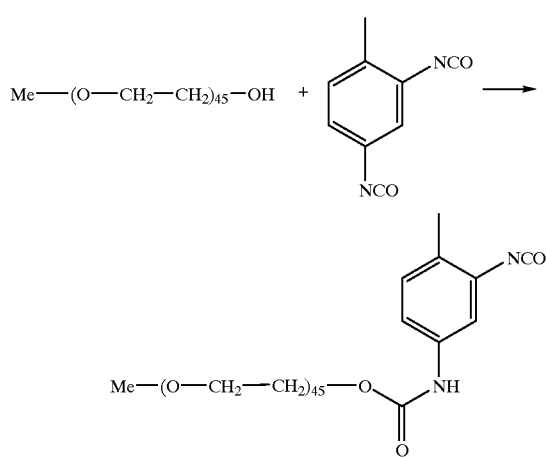

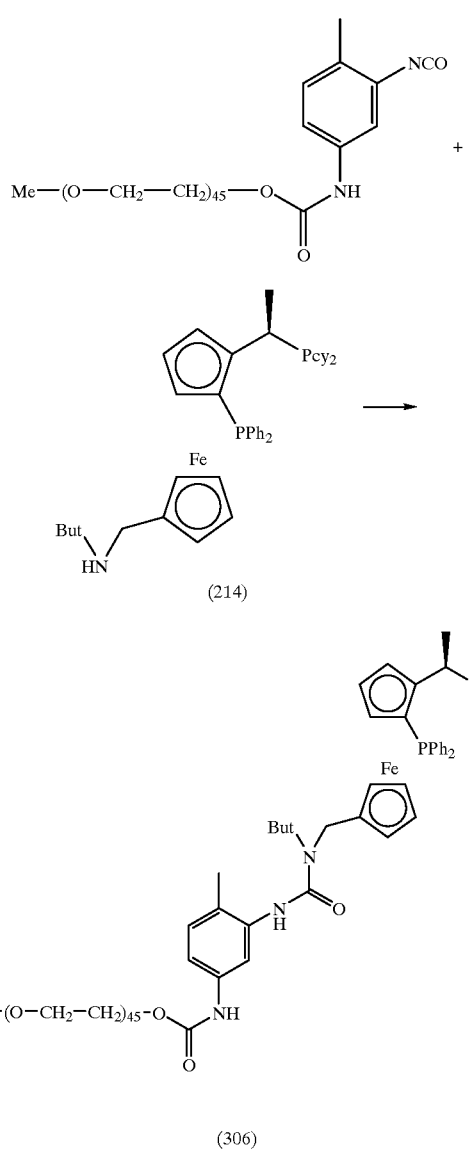

(214)

(306)

2 g of polyethylene glycol 2000 monomethyl ether are dried in 50 ml of dioxane by azetropic distillation of 40 ml of dioxane at 20 torr. 0.12 ml (0.85 mmol) of toluylene 2,4-diisocyanate and 1,4-diazabicyclo[2.2.2]octane (DABCO) are added to this solution and the resulting solution is stirred at 50° C. for 2 hours. 355 mg (0.52 mmol) of ligand 214 and 5 ml of methylene chloride are then added. After a further 2 hours, 4 ml of ethanol are added and the mixture is stirred further for 12 hours under reflux. The orange solution is finally evaporated and dried in a high vacuum at 50° C. This gives 2.3 g of orange, solid product which is water-soluble.

Microanalysis: 1.27% P. This corresponds to 0.2 mmol of ligand/g.

Example B23

Preparation of (R)-1-[1'-(aminomethyl)-(S)-2-diphenylphosphinoferrocenyl] ethyldicyclohexylphosphine

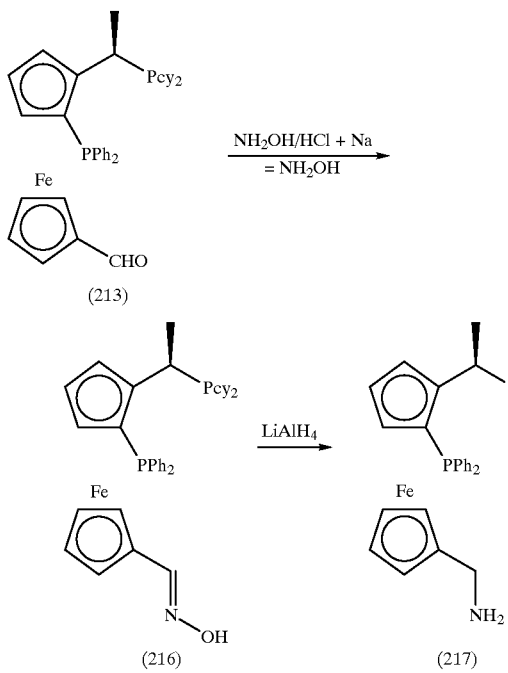

A freshly prepared solution of hydroxylamine (3.5 mmol) in 2 ml of ethanol is added dropwise at 0° C. to a suspension of 1 g (1.6 mmol) of aldehyde 213 in 20 ml of ethanol. The mixture is subsequently stirred for 2 hours at 60° C., giving a red solution. The complete batch is evaporated under reduced pressure on a rotary evaporator, the oil obtained is extracted in methylene chloride/water, the organic phase is washed with water, dried over sodium sulfate and evaporated on a rotary evaporator. This gives 1.04 g of oxime 216 (orange foam).

The crude product is, without purification, partially dissolved in 10 ml of diethyl ether and slowly treated with enough lithium aluminium hydride (about 240 mg) for all the oxime to be reacted according to TLC. The aluminium is precipitated by slow addition of water, the mixture is then taken up in ethyl acetate, dried over sodium sulfate and evaporated on a rotary evaporator. Purification by chromatography (silica gel: Merck 60, eluant: EtOH) gives 0.8 g of product (yield: 80%, orange powder).

Analytical data: $^1$H-NMR (CDCl$_3$): δ 1–1.8 (m, 25H, P(C$_6$H$_{11}$)$_2$, C—CH$_3$), 3.05–3.25 (d of d, J1=43, J2=12, 2H, CH$_2$—N), 3.2 (m, 1H, CH—CH$_3$), 3.55–4.35 (m, 7H, C$_5$H$_3$FeC$_5$H$_4$), 7.1–7.7 (m, 10H, P(C$_6$H$_5$)$_2$). $^{31}$P-NMR (CDCl$_3$): δ –25.1 (d, Pcy$_2$), 16.9 (d, PPh$_2$), JPP 32 Hz.

Example B24

Preparation of (R)-1-[1'-(acetaldehyde)-(S)-2-diphenylphosphinoferrocenyl] ethyldicyclohexylphosphine

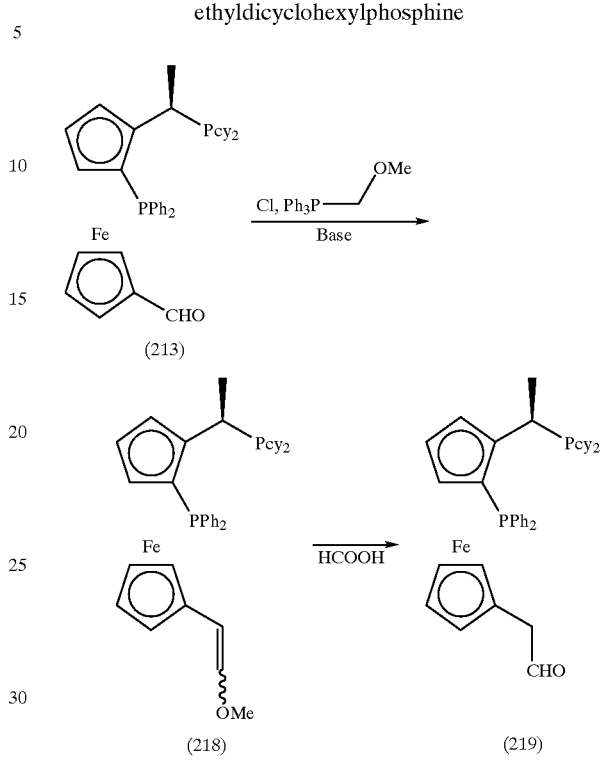

1 mmol of a 1M lithium bis(trimethylsilyl)amide solution in THF is added dropwise to a suspension of 0.33 g (0.95 mmol) of methoxymethyltriphenylphosphonium chloride in 4 ml of THF. Subsequently, at 0° C., a solution of 0.32 g (0.51 mmol) of the aldehyde 213 in 2 ml of THF is added and the red-orange suspension is stirred overnight at room temperature. Extraction in ice, saturated aqueous ammonium chloride solution an ethyl acetate, drying of the organic phase over sodium sulfate and purification by chromatography (silica gel: Merck 60, eluant: toluene) gives 0.24 g of the vinyl ether 218 (yield: 72%, almost solid, orange oil).

Analytical data: A mixture of cis and trans product in a ratio of about 1:1 is obtained. $^1$H-NMR (CDCl$_3$): δ 1–1.8 (m, 25H, P(C$_6$H$_{11}$)$_2$, C—CH$_3$), 3.19 (m, 1H, CH—CH$_3$), 3.52 and 3.65 (each 1s, 3H, cis and trans O—CH$_3$), 3.5–4.4 (m, 7H, C$_5$H$_3$FeC$_5$H$_4$), 4.66 and 5.92 (each 1 d, J=8, cis H—C=C—H), 5.08 and 6.47 (each 1d, J=trans H—C=C—H), 7.1–7.7 (m, 10H, P(C$_6$H$_5$)$_2$). $^{31}$P-NMR (CDCl$_3$): δ –24.8 and –24.9 (two d, cis and trans vinyl ethers), Pcy$_2$), 16.7 and 16.8 (two d, cis and trans vinyl ethers, PPh$_2$), JPP for both 35 Hz.

The aldehyde 219 can be set free by means of acid: the vinyl ether is stirred for 3 hours in formic acid. The orange solution is treated with ice-water, neutralized with 1N NaOH and extracted with ethyl acetate. The organic phase is dried over magnesium sulfate and evaporated on a rotary evaporator.

Analytical data: $^1$H-NMR (CDCl$_3$), the olefinic protons have disappeared completely: δ 1–1.8 (m, 25H, P(C$_6$H$_{11}$)$_2$, C—CH$_3$), 3.7–3.95 (m, CH$_2$—CHO), 3.22 (m, 1H, CH—CH$_3$), 3.6–4.35 (m, 7H, C$_5$H$_3$FeC$_5$H$_4$), 7.1–7.7 (m, 10H, P(C$_6$H$_5$)$_2$) 9.43 (t, 1H, CHO). $^{31}$P-NMR (CDCl$_3$): δ –25.4 (d, Pcy$_2$), 16.9 (d, PPh$_2$), JPP 34 Hz.

Example B25

Immobilization On Polyacrylic Acid

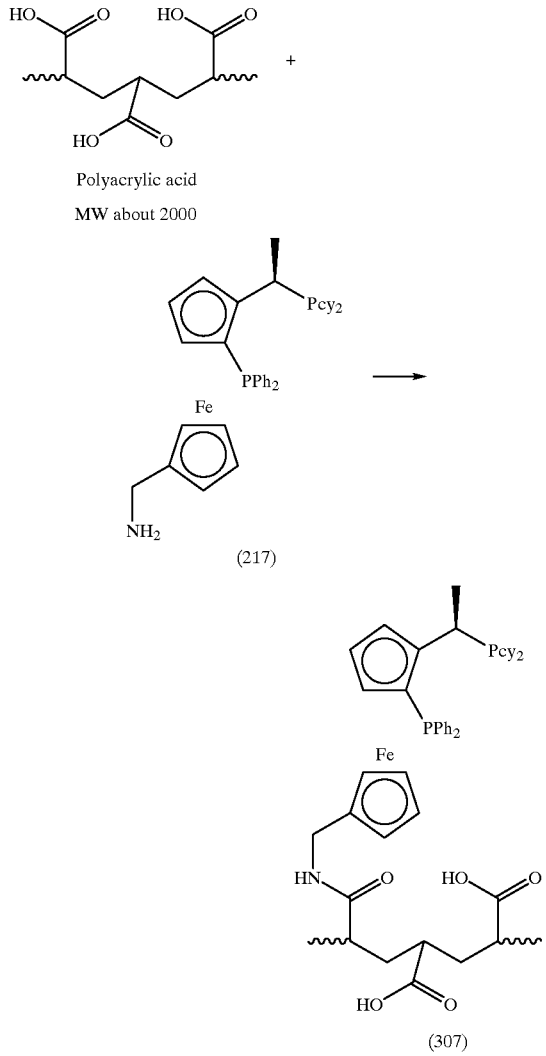

(217)

(307)

106 mg (0.17 mmol) of ligand 217 are added to 1 g of a 65% aqueous solution of polyacrylic acid having a mean molecular weight of 2000 D (Aldrich Cat. No. 19.202-3) in 2.5 ml of water and 13.5 ml of THF. 75 mg (0.36 mmol) of DCC (dicyclohexylcarbodiimide), dissolved in 2.5 ml of THF, are added dropwise over a period of 10 minutes to the above orange solution, forming a yellow-orange mixture. This is stirred overnight and then evaporated at 40° C. on a rotary evaporator. The mixture is subsequently stirred with 5 ml of water, brought to a pH of 8 by slow addition of a saturated $NaHCO_3$ solution and filtered. Finally, the solution is evaporated at 45° C. on a rotary evaporator and the orange, solid product is dried in a high vacuum. Yield: 720 mg. Microanalysis: 1.40% P. This corresponds to 0.226 mmol of ligand per g of product.

Example B26

Preparation of (R)-1-[1'-(aminomethyl)-(S)-2-diphenylphosphinoferrocenyl]ethyldixylylphosphine

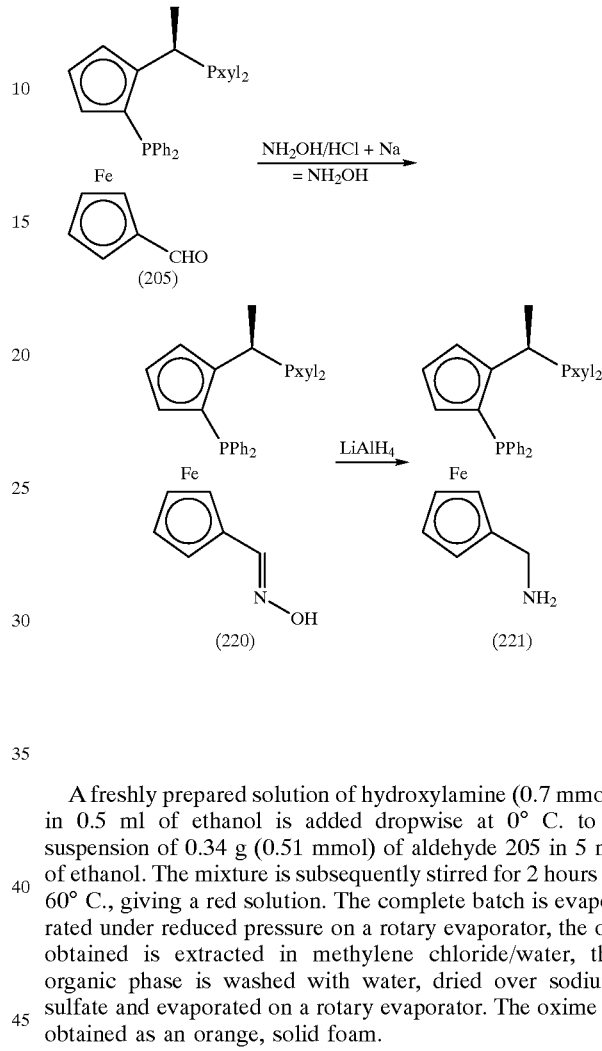

(205) (220) (221)

A freshly prepared solution of hydroxylamine (0.7 mmol) in 0.5 ml of ethanol is added dropwise at 0° C. to a suspension of 0.34 g (0.51 mmol) of aldehyde 205 in 5 ml of ethanol. The mixture is subsequently stirred for 2 hours at 60° C., giving a red solution. The complete batch is evaporated under reduced pressure on a rotary evaporator, the oil obtained is extracted in methylene chloride/water, the organic phase is washed with water, dried over sodium sulfate and evaporated on a rotary evaporator. The oxime is obtained as an orange, solid foam.

The crude product is, without purification, partially dissolved in 3 ml of diethyl ether and slowly treated with enough lithium aluminium hydride (about 130 mg) for all the oxime to be reacted according to TLC. The aluminium is precipitated by slow addition of water, the mixture is then taken up in ether/THF, dried over sodium sulfate and evaporated on a rotary evaporator. Purification by chromatography (silica gel: Merck 60, eluant: EtOH) gives 0.28 g of product (yield: 82%, orange powder).

Analytical data:

$^1$H-NMR ($CDCl_3$): δ1.44 (t, 3H, C—$CH_3$), 2.18 and 2.26 (each 1 s, 12H, Ph—C$\underline{H}_3$), 3.16 (d of d, J1=36, J2=13, 2H, $CH_2$—N), 3.57–4.2 (m, 8H, $C_5H_3FeC_5H_4$, C$\underline{H}$—$CH_3$), 6.75–7.7 (m, 16H, P($C_6H_5$)$_2$ and P($C_6\underline{H}_3Me_2$)$_2$.

$^{31}$P-NMR ($CDCl_3$): δ8.2 (d, (Pxylyl$_2$), −24.2 (d, $PPh_2$), JPP 20 Hz.

Example B27: Bonding to a sugar radical

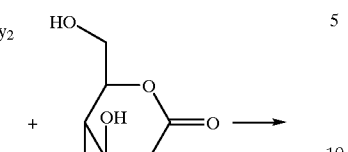

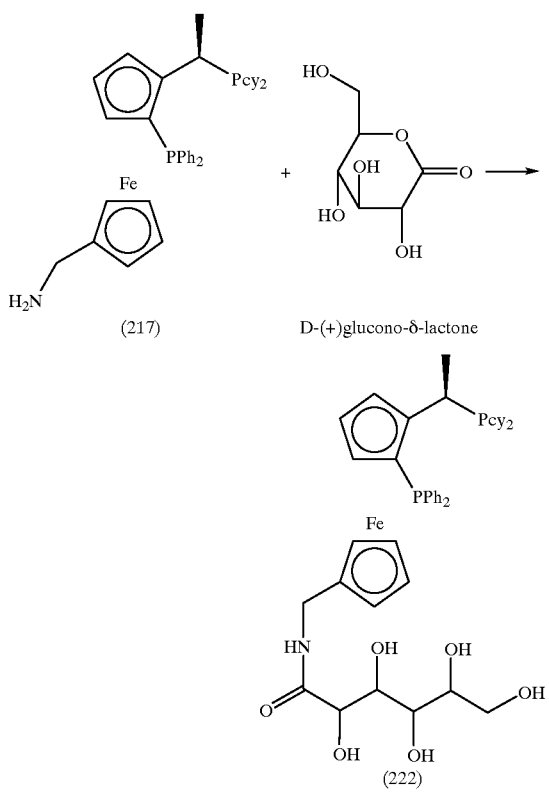

(217)   D-(+)glucono-δ-lactone (222)

36 mg (0.2 mmol) of D-(+)-glucono-lactone and 127 mg (0.2 mmol) of 217 are stirred in 1 ml of MeOH for 2 hours under reflux. The MeOH is then taken off on a rotary evaporator and the orange crude product is purified by chromatography (silica gel: Merck 60, eluant: EtOH). This gives 100 mg of product (yellow solid). Yield: 61%.

The ligand 222 is significantly more polar than the ligand 217: while 217 in MeOH/hexane is distributed in both phases, the ligand 222 goes completely into the MeOH phase.

$^{31}$P-NMR (CDCl$_3$): δ–25.5 (d, Pcy$_2$), 16.9 (d, PPh$_2$), JPP 32 Hz.

Example B28: Immobilization on Amberlite IRC 50 (macroreticular polymethacrylic acid)

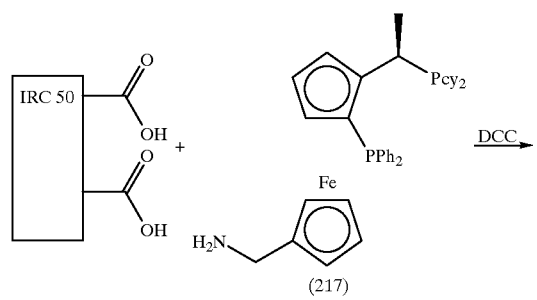

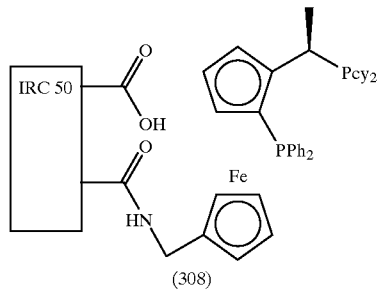

(308)

An orange solution of 54 mg (0.087 mmol) of ligand 217 dissolved in 2 ml of THF is added to 520 mg of polymer beads IRC 50 (washed with 2N, HCl, water, THF then dried at 40° C. in a high vacuum) in 2.5 ml of water and 8 ml of THF. A solution of 70 mg of DCC (N,N-dichclohexylcarboodiimide) dissolved in 2 ml of THF is added dropwise to the above mixture over a period of 30 minutes. During this addition, the yellow colour of the solution becomes much lighter and the polymer becomes yellow. After stirring for 3 hours, the solution is virtually colourless and the polymer is intense yellow. The polymer is filtered off on a G2 frit and washed once with THF, once with DMF, four times with THF (10 ml each time) and is finally dried at 50° C. in a high vacuum. Yellow beads are obtained.

Microanalysis: 0.75% P. This corresponds to 0.121 mmol of ligand/g.

Example B29: Immobilization on low molecular weight polyvinyl alcohol (PVA)

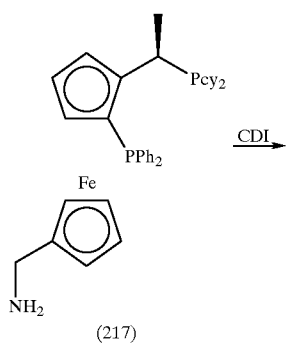

(217)

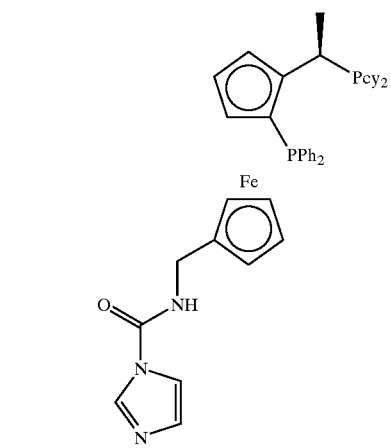

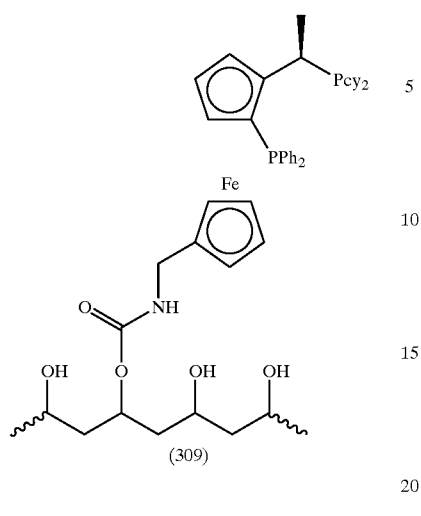

(309)

A solution of 16 mg of CDI (1,1'-carbonyldiimidazole) in 0.7 ml of methylene chloride is added dropwise at 0° C. to a solution of 60 mg (0.096 mmol) of 217 in 1.7 ml of methylene chloride, the resulting orange solution is stirred for 2 hours at room temperature and subsequently added to a mixture of 600 mg of polyvinyl alcohol (Polysciences Inc. MW 6000, Cat. No. 22225) in 5 ml of DMF. After addition of a catalytic amount of dibutyltin dilaurate (5 mg), the mixture is stirred first for 15 hours at 50° C. and subsequently for 5 hours at 100° C., with the polymer virtually dissolving. On cooling to room temperature, a greatly swollen, orange mass is obtained. 10 ml of diethyl ether are added dropwise to this mass while stirring vigorously, forming a fine suspension. After stirring for 7 hours, this suspension is filtered under argon and the residue is washed a number of times with ether, MeOH and ether again and is finally dried at 40° C. in a high vacuum. This gives a yellow-beige powder which is soluble in water.

Microanalysis: 0.49% P. This corresponds to 0.079 mmol of ligand/g.

Example B30: Immobilization on aminomethylated polystyrene using CDI

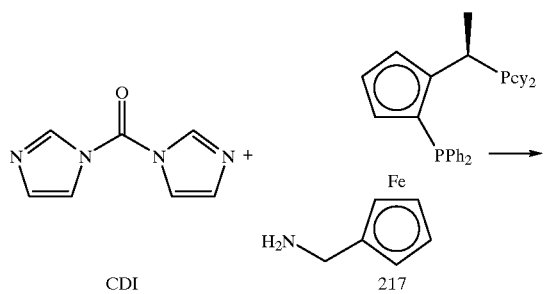

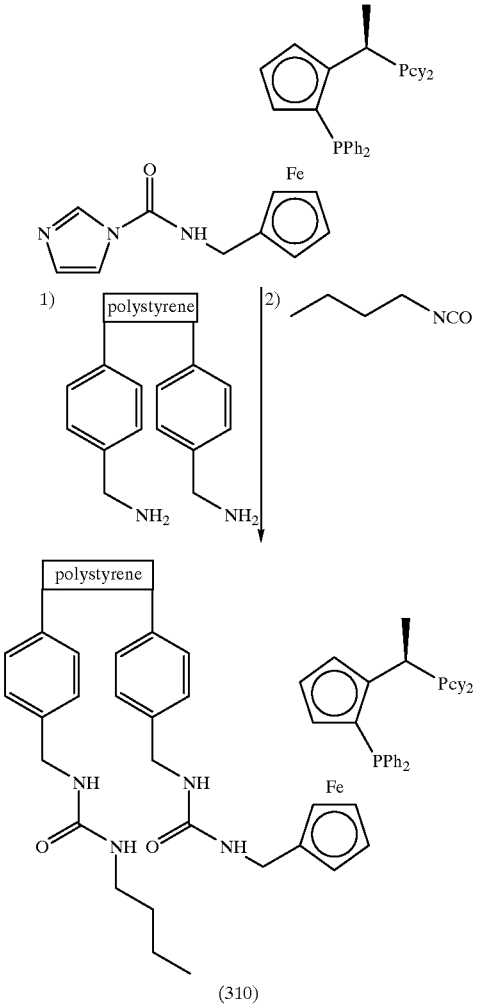

(310)

600 mg of aminomethylated polystyrene crosslinked with 1% of divinylbenzene (Novabiochem 01-64-0010, 0.56 mmol of amino groups per g) are dried at 50° C. in a high vacuum for 2 hours. 6 ml of THF are then added at room temperature and the mixture is slowly stirred, resulting in the polymer swelling. In a second vessel, a solution of 16 mg of CDI (1,1'-carbonyldiimidazole) in 0.7 ml of methylene chloride is added dropwise at 0° C. to a solution of 60 mg (0.096 mmol) of 217 in 1.7 ml of methylene chloride, the resulting orange solution is stirred for 2 hours at room temperature and subsequently added to the polystyrene suspension. This mixture is first stirred for 1.5 hours at 45° C. before 0.2 ml of butyl isocyanate is added in order to convert the remaining amino groups on the polymer. After stirring further for 30 minutes at 45° C., the now yellow polymer is filtered off, washed 4 times with 15 ml of THF and finally dried at 40° C. in a high vacuum.

Microanalysis: 0.4% P. This corresponds to 0.064 mmol of ligand/g.

Example B31: Immobilization on aminomethylated polystyrene using TD1

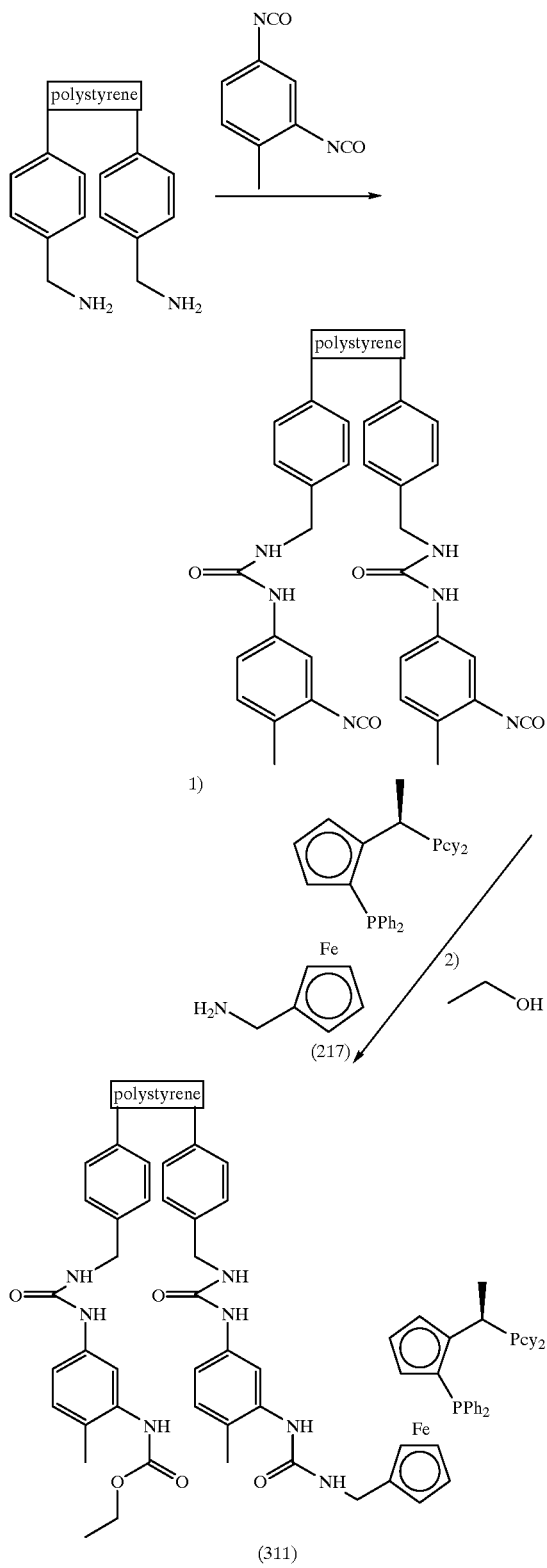

600 mg of aminomethylated polystyrene crosslinked with 1% of divinylbenzene (Novabiochem 01-64-0010, 0.56 mmol of amino groups per g) are dried at 50° C. in a high vacuum for 2 hours. After addition of 6 ml of THF, the mixture is slowly stirred, resulting in the polymer swelling, and is subsequently treated with 1.3 mmol of TD1 (tolylene 4,2-diisocyanate). After 2 hours, the excess TD1 is removed by washing 5 times with 10 ml each time of THF. The polymer is reslurried in 6 ml of THF, treated with an orange solution of 60 mg (0.096 mmol) of 217 in 2 ml of THF and stirred for 2 hours at 40° C., with the polymer becoming yellow and the solution being decolorized. Subsequently, 5 ml of ethanol and a spatula tip of DABCO are added to the mixture and it is stirred overnight at room temperature. The solution is then filtered, the yellow polymer is washed 4 times with THF and twice with ether (10 ml each time) and subsequently dried at 40° C. in a high vacuum. This gives an intensely yellow-coloured powder.

Microanalysis: 0.72% P. This corresponds to 0.116 mmol of ligand/g.

Example B32: Immobilization on Amberlite IRC 76 (polyacrylic acid, gel type, Fluka 06463).

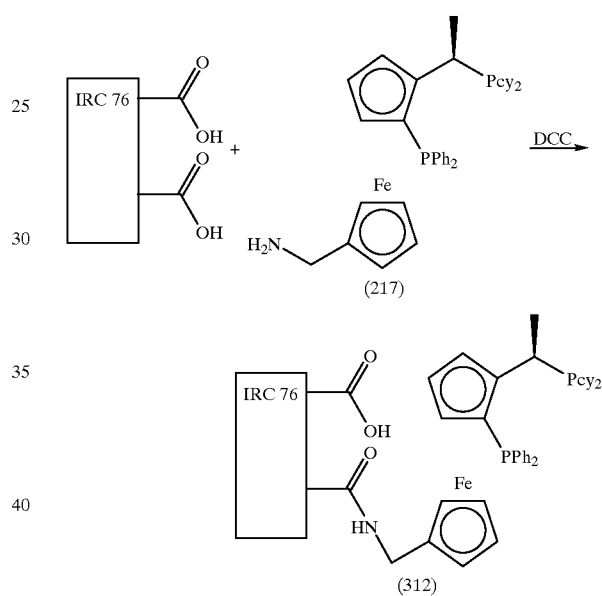

99 mg (0.158 mmol) of ligand 217 are added to 720 mg of polymer beads IRC 76 (washed with 2N HCl, water, THF then dried at 40° C. in a high vacuum) in 4 ml of DMF. A solution of 43 mg of DCC (N,N-dicyclohexylcarbodiimide) dissolved in 1 ml of DMF is added dropwise to the above mixture over a period of 30 minutes. During this addition, the yellow colour of the solution becomes much lighter and the polymer becomes yellow. After stirring for 15 hours, the solution is virtually colourless and the polymer is distinctly yellow. The polymer is filtered off on a G2 frit and is washed a number of times with DMF, ethyl acetate and THF and is finally dried at 50° C. in a high vacuum. Yellow beads are obtained.

Microanalysis: 0.74% P. This corresponds to 0.119 mmol of ligand/g.

Examples B33 to B35: Immobilization of functionalized ligands on silica gel

The ligands (202), (209) and (210) in Table 1 are immobilized on silica gel Grace 332 (particle size 35–70 μm) by the following standard method to give the compounds numbered (301), (302) and (303).

In a flask, silica gel is dried in a high vacuum for 3 hours at 140° C. over a glass frit attachment and is degased a number of times using argon. The silica gel is then cooled under argon, a degased solution of the ligand in toluene (4.5 ml/g of silica gel) is added and the mixture is subsequently slowly stirred overnight at the temperature indicated. After cooling and settling, the supernatant solution is drawn off using a syringe. The mixture is subsequently washed 6 times with MeOH (in each case 6 ml per g of support) and finally dried at 40°–50° C. in a high vacuum.

TABLE 1

Amounts and reaction conditions used and loadings obtained

| Ligand used | Amount mg (mmol) | Silica gel | Amount g | Immobilization Temp/hours | Loading mmol/g | Compound No. |
|---|---|---|---|---|---|---|
| (202) | 175 (0.185) | Grace 332 | 3.5 g | 90° /15 hours | 0.05 | (301) |
| (209) | 320 (0.35) | Grace 332 | 5 g | 88° /18 hours | 0.05 | (302) |
| (210) | 340 (0.35) | Grace 332 | 5 g | 88/18 hours | 0.049 | (303) |

Examples E1–E10: Preparation of N-(2'-methyl-6'-ethylphen-1'yl)-N-(1-methoxymethyl)ethylamine General procedures:

All manipulations are carried out under inert gas. All hydrogenations are carried out using 20 g (97 mmol) of imine. The catalyst is prepared in situ from ligand and [Ir(COD)Cl]$_2$ using a ratio of ligand/Ir of 1.2. The 50 ml steel autoclave is fitted with a magnetic stirrer (1500 rpm) and baffles. The inert gas in the autoclave is displaced by hydrogen, in each case in 4 cycles (10 bar, atmospheric pressure), before the hydrogenation. The desired hydrogen pressure is then set in the autoclave and the hydrogenation is started by switching on the stirrer. The conversion is determined in each case by means of gas chromatography and the optical yield by means of HPLC (column: Chiracel OD). For this purpose, use is made of a sample purified by flash chromatography (silica gel: Merck 60, eluant: hexane/ethyl acetate).

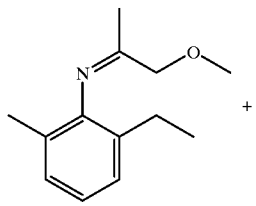

+

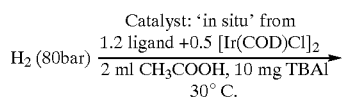

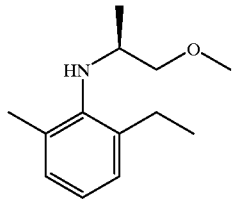

A solution of 0.32 mg of [Ir(COD)Cl]$_2$ (0.0095 mmol of Ir) in 1 ml of THF is added all at once to 22.8 mg of immobilized (R),(S) ligand of the compound (303) from Example C3 and the mixture is stirred slowly, with the yellow solution becoming decolorized. The catalyst is then allowed to settle, the supernatant THF is drawn off using a syringe and the catalyst is dried in a high vacuum. A second flask is charged with 10 mg of tetrabutylammonium iodide (TBAI), 2 ml of acetic acid and finally 20 g (97 mmol) of imine, the solution is blanketed with inert gas and is added to the catalyst. The reaction mixture is then injected into a 50 ml steel autoclave using a steel capillary under a countercurrent of inert gas and is subsequently hydrogenated at 80 bar hydrogen pressure at 25° C. The results of Examples E1–E10 are summarized in Table 2.

TABLE 2

Hydrogenation examples

| Experiment No. | Ligand | S/C | Conversion [%] | Time [min.] | ee | Remarks |
|---|---|---|---|---|---|---|
| E1 | (301) | 20,000 | 89 | 300 | 78 | |
| E2 | (301) | 20,000 | 95 | 1500 | 77 | |
| E3 | (301) | 100,000 | 78 | 960 | 79 | |
| E4 | (301) | 100,000 | 64 | 1200 | 79 | |
| E5 | (301) | 100,000 | 95 | 1000 | 79 | 2 lig/Ir* |
| E6 | (302) | 50,000 | 100 | 360 | 77 | |

TABLE 2-continued

Hydrogenation examples

| Experiment No. | Ligand | S/C | Conversion [%] | Time [min.] | ee | Remarks |
|---|---|---|---|---|---|---|
| E7  | (303) | 50,000  | 100 | 300  | 77 |           |
| E8  | (302) | 10,000  | 100 | 30   | 77 | 2.5 ppm Ir |
| E9  | (303) | 10,000  | 100 | 30   | 77 | 1.8 ppm Ir |
| E10 | (303) | 100,000 | 100 | 1000 | 77 |           |

*) 2 equivalents of ligand per Ir

For the ligands of the formulae (302) and (303), the completeness with which the iridium could be removed was examined in Experiments E8 and E9. In both cases, over 97% of the iridium used is recovered.

Examples E11–E17:

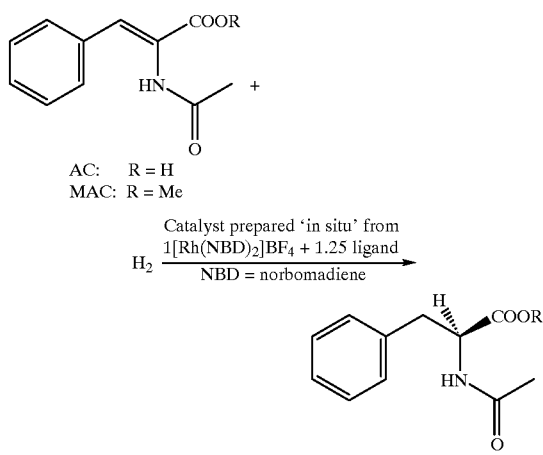

AC: R = H
MAC: R = Me

Catalyst prepared 'in situ' from
1[Rh(NBD)₂]BF₄ + 1.25 ligand
H₂ ——————————————→
NBD = norbomadiene General:

All operations are carried out under an inert atmosphere (argon or nitrogen). Hydrogenation apparatus: 50 ml round-bottom Schlenk with rubber septum and magnetic stirrer (1200 rpm). The catalysts are prepared in situ under argon in the hydrogenation vessel starting from 1 equivalent of [Rh(NBD)₂]BF₄ and 1.25 equivalents of ligand in a solvent. A solution of the substrate is subsequently added. The argon is then replaced by hydrogen by evacuating and filling with hydrogen (atmospheric pressure) 3 times. The hydrogenations are carried out at 40° C. and are started by switching on the stirrer. The course of the hydrogenation is followed by means of the drop in the hydrogen pressure in the hydrogen reservoir. Conversion and enantioselectivity are determined by means of GC (columns: conversion=OV101, enantioselectivity=Chirasil-L-val). If AC is used as substrate, starting material and product are converted into the corresponding methyl ester using Meerwein's salt ([(CH₃)₃O]BF₄) in the presence of triethylamine at 0° C. in methylene chloride prior to GC analysis.

E11: Hydrogenation using (308)

The catalyst is prepared by stirring 55 mg (0.0075 mmol) of ligand 308 and 2.3 mg (0.0062 mmol) of [Rh(NBD)₂]BF₄ in 3 ml of MeOH for 15 minutes. A colourless solution and an orange immobilized catalyst are obtained. A solution of 550 mg (2.5 mmol) of methyl acetamidocinnamate in 7 ml of MeOH and 50 µl of methanesulfonic acid are added to the above mixture and the hydrogenation is started. After the hydrogenation, the solution is colourless and the immobilized catalyst is orange. The catalyst can be separated off by filtration.

E12: Hydrogenation using (311)

The catalyst is prepared by stirring 65 mg (0.0075 mmol) of ligand (311) and 2.3 mg (0.0062 mmol) of [Rh(NBD)₂]BF₄ in 1.5 ml of MeOH and 3 ml of toluene for 15 minutes. A colourless solution and an orange immobilized catalyst are obtained. A solution of 550 mg (2.5 mmol) of methyl acetamidocinnamate in 2.5 ml of MeOH, 3 ml of toluene and 10 µl of methanesulfonic acid are added to the above mixture and the hydrogenation is started. After the hydrogenation, the solution is colourless and the immobilized catalyst is orange. The catalyst can be separated off by filtration and still has catalytic activity.

E13: Hydrogenation using (312)

The catalyst is prepared by stirring 126 mg (0.15 mmol) of ligand 312 and 4.6 mg (0.0124 mmol) of [Rh(NBD)₂]BF₄ in 1 ml of MeOH for 15 minutes. A colourless solution and an orange immobilized catalyst are obtained. A solution of 550 mg (2.5 mmol) of methyl acetamidocinnamate in 3 ml of MeOH and 20 µl of methanesulfonic acid are added to the above mixture and the hydrogenation is started. After the hydrogenation, the solution is colourless and the immobilized catalyst is orange. The catalyst can be separated off by filtration.

Results:

| Experiment No. | Ligand No. | Substrate | S/C | Solvent | Additive | Conversion | Time (h) | ee |
|---|---|---|---|---|---|---|---|---|
| E11 | 308 | MAC | 400 | MeOH     | MeSO₃H | 84%  | 17 | 85.1% |
| E12 | 311 | MAC | 400 | MeOH/Tol | MeSO₃H | 100% | 15 | 79%   |
| E13 | 312 | MAC | 200 | MeOH     | MeSO₃H | 100% | 8  | 81%   |

E14: Hydrogenation using (306) The catalyst is prepared by stirring 36 mg (0.0075 mmol) of ligand 306 and 2.3 mg (0.0062 mmol) of [Rh(NBD)$_2$]BF$_4$ in 3 ml of MeOH and for 15 minutes and the MeOH is subsequently distilled off at room temperature by means of a high vacuum. A suspension of 513 mg (2.5 mmol) of acetamidocinnamic acid in 10 ml of water is added to the resulting red mass and the hydrogenation is started.

E15: Hydrogenation using (309)

The catalyst is prepared by stirring 95 mg (0.0075 mmol) of ligand 309 and 2.3 mg (0.0062 mmol) of [Rh(NBD)$_2$]BF$_4$ in 0.5 ml of MeOH and 1 ml of water for 15 minutes. A suspension of 513 mg (2.5 mmol) of acetamidocinnamic acid in 9 ml of water is added to the resulting orange solution and the hydrogenation is started.

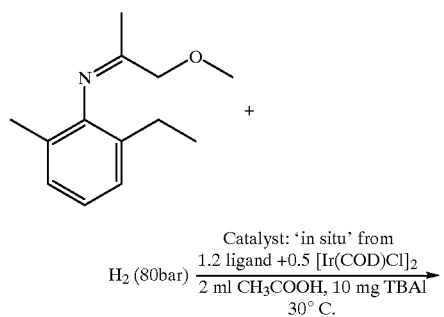

| Experiment No. | Ligand No. | Substrate | S/C | Solvent | Additive | Conversion | Time (h) | ee |
|---|---|---|---|---|---|---|---|---|
| E14 | 306 | AC | 400 | H$_2$O | — | 53 | 4 | 83 |
| E15 | 309 | AC | 400 | H$_2$O | — | 72 | 16 | 67 |

E16 and E17: Hydrogenation using (307)

The catalyst is prepared by stirring 35 mg (0.0075 mmol) of ligand 307 and 2.3 mg (0.0062 mmol) of [Rh(NBD)$_2$]BF$_4$ in 2 ml of MeOH and 20 μl of methanesulfonic acid for 15 minutes. A solution of 550 mg (2.5 mmol) of methyl acetacetamidocinnamate in 8 ml of MeOH is added to the resulting orange solution and the hydrogenation is started.

E16: Removal of the catalyst by adsorption: 0.4 g of ion exchanger (Amberlite IRA68) is added to the orange reaction solution after the hydrogenation and the mixture is stirred overnight. The ion exchanger is filtered off and the now largely decolorized solution is evaporated on a rotary evaporator. Microanalytical examination of the hydrogenation product indicates that 80% of both ligand and Rh have been removed.

E17: Removal of the catalyst by extraction: The orange reaction solution is evaporated to dryness on a rotary evaporator. The mixture is then stirred in 5 ml of water, 0.5 ml of a 0.07 molaren phosphate buffer (pH 7) and 5 ml of ethyl acetate and the pH is brought to 8 by addition of 1N NaOH. During this procedure, the orange colour of the catalyst passes completely into the aqueous phase. The organic phase is collected, dried over sodium sulfate and evaporated on a rotary evaporator. A white hydrogenation product is obtained. Microanalysis (P and Rh) of the product indicates that over 95% of the catalyst has been removed.

-continued

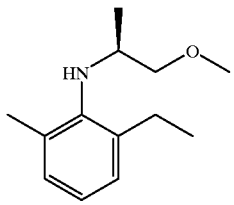

General: All manipulations are carried out under inert gas. All hydrogenations are carried out using 20 g (97 mmol) of imine. The catalyst is prepared in situ from ligand and [Ir(COD)Cl]$_2$, using a ratio of ligand/Ir of 1.2. The 50 ml steel autoclave is fitted with a magnetic stirrer (1500 rpm) and baffles. The inert gas in the autoclave is displaced by hydrogen, in each case in 4 cycles (10 bar, atmospheric pressure), before the hydrogenation. The desired hydrogen pressure is then set in the autoclave and the hydrogenation is started by switching on the stirrer. The conversion is in each case determined by means of gas chromatography and the optical yield is determined by means of HPLC (column: Chiracel OD). For this purpose, a sample purified by flash chromatography (silica gel: Merck 60, eluant: hexane/ethyl acetate) is used.

The procedure is illustrated by means of the following experiments.

| Experiment No. | Ligand No. | Substrate | S/C | Solvent | Additive | Conversion | Time (h) | ee |
|---|---|---|---|---|---|---|---|---|
| E16 | 307 | MAC | 400 | MeOH | MeSO$_3$H | 100 | 0.5 | 91 |
| E17 | 307 | MAC | 400 | MeOH | MeSO$_3$H | 100 | 0.5 | 91 |

Example E18–21:

Preparation of N-(2'-methyl-6'-ethylphen-1'yl)-N-(1-methoxymethyl)ethylamine

Hydrogenation. A solution of 3.2 mg of [Ir(COD)Cl]$_2$ (0.095 mmol of Ir) in 1 ml of THF is added to 10.2 mg (0.012 mmol) of ligand (R),(S)-(103) in a Schlenk vessel and the mixture is stirred for 5 minutes. The THF is then taken off by applying a vacuum and the catalyst precursor is dried briefly in a high vacuum. A second flask is charged with 10 mg of tetrabutylammonium iodide, 2 ml of acetic acid and finally 20 g (97 mmol) of imine, the solution is blanketed with inert gas and added to the catalyst. The reaction mixture is then injected into a 50 ml steel autoclave using a steel capillary under a countercurrent of inert gas and subsequently hydrogenated at 80 bar of hydrogen pressure at 25° C. After 30 minutes, hydrogen absorption has ended.

Removal of the catalyst by extraction: The autoclave is discharged, the hydrogenation solution is treated with 11 ml of hexane and washed twice with 10 ml of water, it is subsequently extracted with 20 ml of 1N NaOH. Small amounts of a foam-like material are formed at the interface between the organic and aqueous phases during the extraction. The organic phase is separated off and evaporated on a rotary evaporator. Its content of P and Ir is below the detection limit of the analytical method used (P: 4 ppm; Ir: 5 ppm). This means that more than 88% of the ligand and more than 93% of the Ir have been removed.

Hydrogenations using ligand (103)

| Experiment No. | S/C* | Temp. [° C.] | Conversion [%] | Time [min.] | ee |
|---|---|---|---|---|---|
| E18 | 20,000 | 25 | 100 | 30 | 79.9 |
| E19b | 10,000 | 25 | 100 | 30 | n.d.* |
| E20 | 120,000 | 25 | 100 | 240 | 80 |
| E21 | 120,000 | 50 | 100 | 90 | 76 |

S/C*: Substrate to catalyst in mol; n.d.*: not determined

What is claimed is:

1. A compound of the formula VI

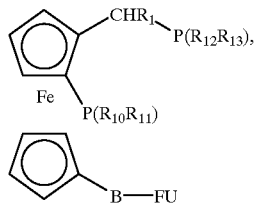

(VI)

$R_1$ is $C_1$–$C_8$alkyl, phenyl or phenyl substituted by from 1 to 3 $C_1$–$C_4$alkyl or $C_1$–$C_4$alkoxy;

$R_{10}$, $R_{11}$, $R_{12}$ and $R_{13}$ are, independently of one another, $C_1$–$C_{12}$alkyl, $C_5$–$C_{12}$cycloalkyl, phenyl, $C_1$–$C_4$alkyl- or $C_1$–$C_4$alkoxy-substituted $C_5$–$C_{12}$cycloalkyl or phenyl substituted by from one to three $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —[$^+NR_7R_8R_9$]$X^-$ or $C_1$–$C_5$fluoroalkyl; or the groups —$PR_{10}R_{11}$ and —$PR_{12}R_{13}$ are each, independently of one another, a radical of the formula IV, IVa, IVb or IVc

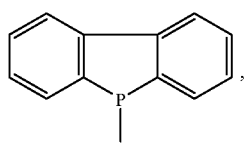

(IV)

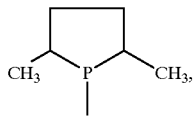

(IVa)

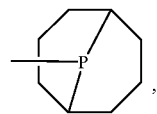

(IVb)

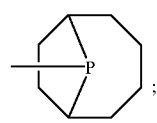

(IVc)

$R_4$, $R_5$ and $R_6$ are, independently of one another, $C_1$–$C_{12}$alkyl or phenyl;

$R_7$ and $R^8$ are, independently of one another, H, $C_1$–$C_{12}$alkyl or phenyl or $R_7$ and $R_8$ together are tetramethylene, pentamethylene or 3-oxa-1,5-pentylene;

$R_9$ is H or $C_1$–$C_4$alkyl;

M is H or an alkali metal;

$X^-$ is the anion of a monobasic acid;

halogen is fluorine, chlorine, bromine or iodine; and a) B is a direct bond and FU is a functional group bound via a carbon atom to the cyclopentadienyl; or b) B is a bridging group bound via a carbon atom or a silicon atom to the cyclopentadienyl and FU is a functional group;

with the exception of the compound of the formula (VI), in which $R_1$ is methyl, $R_{10}$ and $R_{11}$ are phenyl, $R_{12}$ and $R_{13}$ are cyclohexyl, B is 1,3-propylene and FU is $NH_2$; and with the exception of compounds of the formula (VI) in which B is $Si(R_{12'})_2$"$R_{13'}$, and FU is Z, where $R_{12'}$ are each, independently of one another, $C_1$–$C_{12}$alkyl, $C_3$–$C_7$-cycloalkyl, benzyl or phenyl or the two radicals $R_{12'}$ together are $C_5$–$C_{12}$alkylene;

$R_{13'}$ is $C_1$–$C_{12}$alkylene or phenylene;

Z is Cl, $NH_2$, NH—$C_1$–$C_{12}$alkyl, or a group —A—CO—NH—$R_{14}$-$Si(R_a)_n$ $(OR_{15})_{3-n}$;

A is NH or $N(C_1$–$C_{12}$alkyl);

$R_{14}$ is $C_1$–$C_{12}$alkylene;

$R_{15}$ is $C_1$–$C_{12}$alkyl;

$R_a$ is $C_1$–$C_4$alkyl or $OR_{15}$; and n is 0, 1 or 2.

2. A compound of the formula VI according to claim 1, wherein the directly C-bonded functional group FU is a carboxyl, carboxylate, carboxylic ester, carboxamide, cyano, imino, aldehyde or ketone group.

3. A compound of the formula VI according to claim 2, wherein the functional group FU is an aldehyde or ketone.

4. A compound of the formula VI according to claim 1, wherein the functional group bound via a carbon atom of a bridging group B is a carboxyl, carboxylate, carboxylic ester, carboxamide, cyano, imino, aldehyde, ketone, amine, alcohol, isocyanate, halogen or glycidyl group or a polymerizable group.

5. A compound of the formula VI according to claim 4, wherein the polymerizable group is a vinyl group which is unsubstituted or substituted by $C_1$–$C_4$alkyl.

6. A compound of the formula VI according to claim 4, wherein the functional group bound via a carbon atom of a bridging group B is an amine or alcohol group or a polymerizable group.

7. A compound of the formula VI according to claim 1, wherein the bridging group B contains from 1 to 30 atoms, selected from the group consisting of C, O, S and N in the chain.

8. A compound of the formula VI according to claim 1, wherein B is unsubstituted linear or branched $C_1$–$C_{12}$alkylene, $C_2$–$C_{12}$alkenylene, $C_2$–$C_{12}$alkynylene, $C_5$–$C_{12}$cycloalkylene, $C_5$–$C_{12}$cycloalkenylene, phenylene or phenylene-($C_1$–$C_{12}$)alkylene or $C_1$–$C_4$alkyl-, $C_1$–$C_4$alkoxy-, halogen- or hydroxy-substituted linear or branched $C_1$–$C_{12}$alkylene, $C_2$–$C_{12}$alkenylene, $C_2$–$C_{12}$alkynylene, $C_5$–$C_{12}$cycloalkylene, $C_5$–$C_{12}$cycloalkenylene, phenylene or phenylene-($C_1$–$C_{12}$)alkylene and FU is halogen, OH, $NH_2$, $NH(C_1$–$C_{12})$alkyl, (O)C—H, (O)C—($C_1$–$C_{12}$)alkyl, COOH, COCl, COO($C_1$–$C_6$)alkyl or a group OC(O)—$CR_c$=$CR_dR_e$ or OC($NR_f$)—$CR_c$=$CR_dR_e$, in which $R_c$, $R_d$, $R_3$ and $R_f$ are, independently of one another, hydrogen, $C_1$–$C_{C6}$alkyl or phenyl.

9. A compound of the formula VI according to claim 1, wherein B is unsubstituted or halogen- or OH-substituted $C_1$–$C_{12}$alkylene.

10. A compound of the formula VI according to claim 1, wherein FU is preferably OH, $NH_2$, $NH(C_1$–$C_{12})$alkyl or HC(O).

11. A compound of the formula VI according to claim 1, wherein B is a direct bond and FU is (O)C—H, (O)C—($C_1$–$C_{12}$)alkyl, COOH, COCl, CN or COO($C_1$–$C_{12}$)alkyl.

12. A compound of the formula VI according to claim 1, wherein B is a direct bond and FU is (O)CH or (O)C—($C_1$–$C_{12}$)alkyl.

13. A compound of the formula VI according to claim 1, wherein $R_1$ is methyl, ethyl, propyl or butyl.

14. A compound of the formula VI according to claim 1, wherein $R_{10}$, $R_{11}$, $R_{12}$ or $R_{13}$ as substituted phenyl is 2-methyl-, 3-methyl-, 4-methyl-, 2- or 4-ethyl-, 2- or 4-i-propyl-, 2- or 4-t-butyl-, 2-methoxy-, 3-methoxy-, 4-methoxy-, 2- or 4-ethoxy-, 4-trimethylsilyl-, 2- or 4-fluoro-, 2,4-difluoro-, 2- or 4-chloro-, 2,4-dichloro-, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(dimethylamino)-, 2- or 4-$SO_3H$-, 2- or 4-$SO_3Na$—, 2- or 4-[$^+NH_3Cl$]-, 3,4,5-trimethyl-, 2,4,6-trimethyl-, 4-trifluoromethyl- or 3,5-di(trifluoromethyl)phen-1-yl.

15. A compound of the formula VI according to claim 1, wherein $R_{10}$ and $R_{11}$ are each cyclohexyl, t-butyl, phenyl, 2- or, 4-methylphen-1-yl, 2- or 4-methoxyphen-1-yl, 2- or 4-(dimethylamino)phen-1-yl, 3,5-dimethyl-4-(dimethylamino)phen-1-yl or 3,5-dimethyl-4-methoxyphen-1-yl.

16. A compound of the formula VI according to claim 1, wherein $R_{12}$ and $R_{13}$ are each $C_1$–$C_8$alkyl, $C_5$–$C_8$cycloalkyl or phenyl which may be unsubstituted or substituted by 1 or 2 substituents.

17. A compound of the formula VI according to claim 1, wherein $R_{12}$ and $R_{13}$ are identical and are t-butyl, phenyl, cyclohexyl, 2- or 4-methylphen-1-yl, 2- or 4-methoxyphen-1-yl, 2- or 4-(dimethylamino)phen-1-yl, 3,5-dimethylphen-1-yl and 3,5-dimethyl-4-methoxyphen-1-yl.

18. A compound of the formula VI according to claim 1, wherein $R_1$ is methyl, $R_{12}$ are $R_{13}$ are each t-butyl, cyclohexyl, phenyl or 3,5-dimethylphen-1-yl and $R_{10}$ and $R_{11}$ are phenyl, cyclohexyl or t-butyl.

19. A compound of the formula (Ia), (Ib) or (Ic)

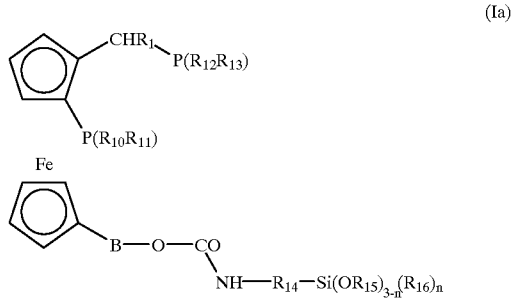

(Ia)

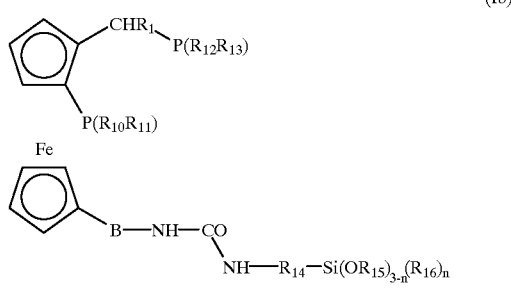

(Ib)

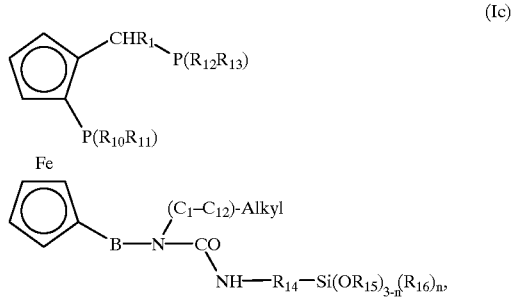

(Ic)

$R_1$, $R_{10}$, $R_{11}$, $R_{12}$ and B are as defined in claim 1; and
$R_{14}$ is $C_1$–$C_{12}$alkylene;
$R_{15}$ is $C_1$–$C_{12}$alkyl;
$R_{16}$ is $C_1$–$C_4$alkyl or $OR_{15}$;
and n is 0, 1 and 2.

20. A compound of the formula VIIIa or VIIIb

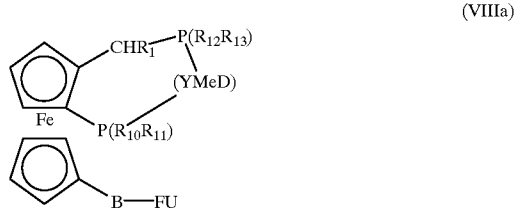

(VIIIa)

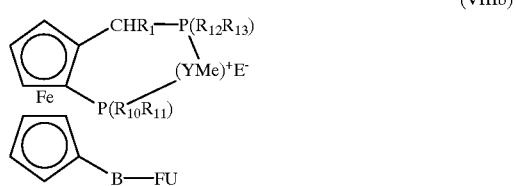

(VIIIb)

where $R_1$, $R_{10}$, $R_{11}$, $R_{12}$, $R_{13}$, B and FU are as defined in claim 1;

Y is two monoolefin ligands or one diene ligand;

Me is a d-8 metal;

D is —Cl, —Br, —I;

E⁻ is the anion of an oxyacid or complex acid.

21. Inorganic or organic polymeric support material to which a bound a terrocenyldiphosphine of the formula VI

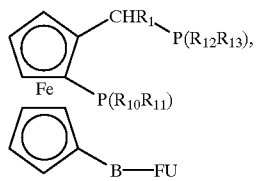
(VI)

wherein the ferrocenyldiphosphine is bound via the functional group FU to the inorganic or polymeric organic support material, where the radicals B, FU, $R_1$, $R_{10}$, $R_{11}$, $R_{12}$ and $R_{13}$ are as defined in claim 1.

22. Polymeric organic material comprising structural repeating units of the formula XIa or XIb

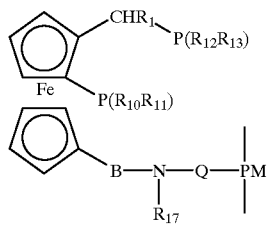
(XIa)

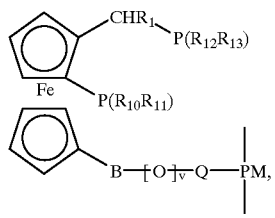
(XIb)

B, $R_1$, $R_{10}$, $R_{11}$, $R_{12}$ and $R_{13}$ are as defined in claim 1;

$R_{17}$ is H or $C_1$–$C_{12}$alkyl;

v is 0 or 1;

Q is a bridging group formed from a monoisocyanate or diisocyanate; and

PM is the radical of a polymer-forming monomer which contains, directly or in a side chain, a bonded hydroxyl group or a bonded primary or secondary amino group as functional group which is bound to the diphosphine via a bridging group Q formed from a mono- or diisocyanate.

23. A d-8 metal complex of an inorganic or organic polymeric support material to which a ferrocenyldiphosphine of the formula VI

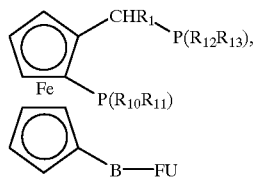
(VI)

is bound via the functional group FU, where the radicals B, FU, $R_1$, $R_{10}$, $R_{11}$, $R_{12}$ and $R_{13}$ are as defined in claim 1.

24. A compound of the formula

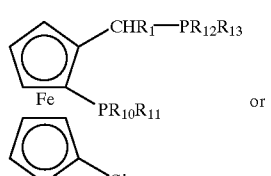
(VIa)

or

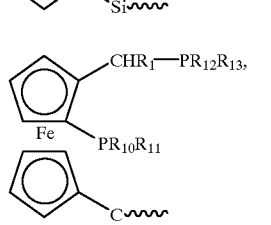
(VIb)

in which $R_1$, $R_{10}$, $R_{11}$, $R_{12}$ and $R_{13}$ are as defined in claim 1;

Si⌇⌇ is a radical which is bound via a silicon atom and makes the compound (VIa) extractable or absorbable; and

C⌇⌇ is a radical which is bound via a carbon atom and makes the compound (VIb) extractable or absorbable.

25. A ruthenium complex containing a ferrocenyl ligand of the formula (VI), (VIa) or (VIb)

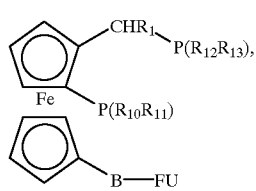
(VI)

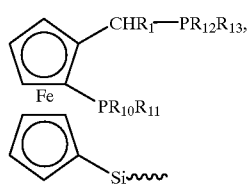
(VIa)

-continued

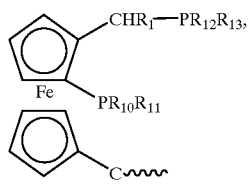

(VIb)

where $R_1$, $R_{10}$, $R_{11}$, $R_{12}$, $R_{13}$, B, and FU are as defined in claim 1.

Si is a radical which is bound via a silicon atom and makes the compound (VIa) extractable or absorbable; and C is a radical which is bound via a carbon atom and makes the compound (VIb) extractable or absorbable;

and additionally the ferrocenyl ligand of formula (VI) may be bound via the functional group FU to an inorganic or polymeric organic support material.

26. A heterogeneous or homogeneous catalyst for the hydrogenation or organic double and triple bonds wherein the catalyst comprises a complex as defined in claim 25.

* * * * *